United States Patent [19]

Yanagisawa et al.

[11] Patent Number: 4,699,905

[45] Date of Patent: Oct. 13, 1987

[54] PERHYDROTHIAZEPINE DERIVATIVES, THEIR PREPARATION AND THEIR THERAPEUTIC USE

[75] Inventors: Hiroaki Yanagisawa; Sadao Ishihara; Akiko Ando; Takuro Kanazaki; Hiroyuki Koike; Yoshio Tsujita, all of Hiromachi, Japan

[73] Assignee: Sankyo Company, Limited, Tokyo, Japan

[21] Appl. No.: 721,303

[22] Filed: Apr. 9, 1985

[30] Foreign Application Priority Data

Apr. 10, 1984 [JP] Japan .................................... 59-71353
Dec. 26, 1984 [JP] Japan ................................. 59-273451

[51] Int. Cl.$^4$ .................... C07D 281/06; A61K 31/55
[52] U.S. Cl. ...................................... 514/211; 540/488
[58] Field of Search ................. 260/239.3 R; 514/211; 540/488

[56] References Cited

U.S. PATENT DOCUMENTS 4,587,050  5/1986  Harris et al. ......................... 540/463

FOREIGN PATENT DOCUMENTS 68173   1/1983  European Pat. Off. ..... 260/239.3 R
120728  10/1984 European Pat. Off. ............ 540/488

Primary Examiner—Robert T. Bond
Attorney, Agent, or Firm—Frishauf, Holtz, Goodman & Woodward

[57] ABSTRACT

Compounds of formula (I):

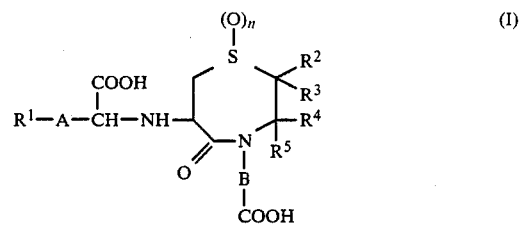

(wherein: $R^1$ represents an optionally substituted alkyl, cycloalkyl, aryl, partially hydrogenated aryl or heterocyclic group; $R^2$, $R^3$, $R^4$ and $R^5$ represent hydrogen or an optionally substituted alkyl, cycloalkyl, aralkyl, aryl, heterocyclic or heterocyclic-alkyl group or any adjacent pair thereof form a cyclic structure, at least one not being hydrogen; A represents a bond, or a methylene, ethylene, oxymethyl or thiomethyl group; B represents an alkylene, alkylidene, cycloalkylene or cycloalkylidene group; and n is 0, 1 or 2) and salts and esters thereof are hypotensive agents.

62 Claims, No Drawings

PERHYDROTHIAZEPINE DERIVATIVES, THEIR PREPARATION AND THEIR THERAPEUTIC USE

BACKGROUND TO THE INVENTION

The present invention relates to a series of perhydrothiazepine derivatives which have the valuable ability to lower blood pressure and hence which are of potential use in the treatment of humans and other animals suffering from elevated blood pressure.

There is considerable evidence that reduction of elevated blood pressure reduces the risk of morbidity and mortality. Elevated blood pressure (hypertension) can be caused by a variety of factors and a large number of drugs is available for the treatment of hypertension, the drug of choice being dictated in large measure by the cause of the hypertension, as well as the degree of hypertension and the acceptance of the treatment by the patient. One of the known causes of hypertension is the presence in blood plasma of the polypeptide known as angiotensin II, and a reduction in the blood plasma levels of angiotensin II has been shown to reduce hypertension. The first step in the production of angiotensin II in the mammalian body is the conversion of a blood protein, by the enzyme renin to a polypeptide known as "angiotensin I". This angiotensin I is then converted by angiotensin converting enzyme (hereinafter referred to, as is conventional, as "ACE") to angiotensin II. Clearly, this preparative route provides several opportunities for reducing the plasma levels of angiotensin II, for example by inhibiting the activity of renin or of ACE. Certain polypeptides have been found to inhibit the activity of renin and have been proposed for use as hypotensive agents. Recently, it has also been discovered that certain perhydrothiazepine compounds are capable of inhibiting the activity of ACE and similarly have been proposed for use as hypotensive agents.

An advantage of inhibiting the activity of ACE, as compared with inhibiting the activity of renin, is that ACE not only participates in the formation of angiotensin II, but also participates in the metabolism of bradykinin, converting it to an inert substance. Bradykinin is a natural vasodilator and its elimination would thus be a further positive factor in elevated blood pressure.

For example, certain perhydro-1,4-thiazepin-5-one derivatives (as well as their corresponding thiazocine analogs) are disclosed in European Patent Publication No. 68,173; these thiazepine derivatives differ from those of the present invention principally in being unsubstituted at the 2- and 3-positions. There is also a mention of certain 1,4-thiazepine derivatives similar to those of the present invention in European Patent Publication No. 120,728 (published after the priority dates of the present application), but the 1,4-thiazepine derivatives disclosed therein differ from those of the present invention primarily in the nature of the substituent at the 6-position; additionally, those derivatives actually disclosed are unsubstituted at both the 2- and 3-positions.

The compounds of the present invention have the advantage over the prior art compounds of higher activity and a longer duration of activity, in general, than the prior art compounds, especially those of European Patent Publication No. 68,173. The compounds of the invention differ from the prior art compounds in that they possess at the 2- and/or 3-positions a group selected from certain specific groups which have an essentially hydrophobic (or lyophilic) nature. It is believed that the hydrophobic nature of such groups leads to enhanced binding of the compound to ACE (hence inhibiting the activity of ACE to a greater degree) and an increase in fat-solubility (which leads to enhanced retention in the tissues of the mammalian body and delayed excretion). These factors together lead to the expectation that the compounds of the invention will demonstrate a greater ability to lower blood pressure, coupled with a greater duration of activity.

The compounds of the invention are named herein as perhydro-1,4-thiazepine derivatives; an alternative nomenclature sometimes employed is as 1-thia-4-azacycloheptane derivatives.

BRIEF SUMMARY OF INVENTION

The compounds of the present invention are those compounds of formula (I):

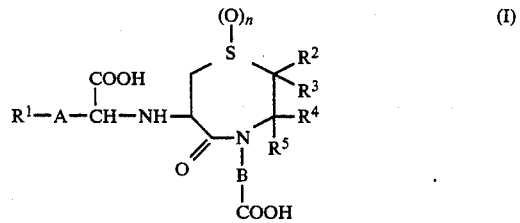

wherein:

$R^1$ represents a $C_1-C_{10}$ alkyl group, a $C_3-C_8$ cycloalkyl group, a carbocyclic aryl group having from 6 to 14 ring carbon atoms, a partially hydrogenated carbocyclic aryl group having from 6 to 14 ring carbon atoms or a heterocyclic group having from 5 to 14 ring atoms, of which from 1 to 5 are hetero-atoms selected from the group consisting of nitrogen, sulfur and oxygen atoms, said groups represented by $R^1$ being unsubstituted or having at least one substituent selected from the group consisting of:

(a) oxo groups, $C_1-C_6$ alkyl groups, $C_6-C_{10}$ carbocyclic aryl groups, aralkyl groups wherein the alkyl part is $C_1-C_6$ alkyl and the aryl part is $C_6-C_{10}$ carbocyclic aryl, hydroxy groups, $C_1-C_6$ alkoxy groups, alkoxyalkoxy groups where each alkoxy part is $C_1-C_6$, aralkyloxy groups, wherein the alkoxy part is $C_1-C_6$ alkoxy and the aryl part is $C_6-C_{10}$ carbocyclic aryl, aryloxy groups, wherein the aryl part is $C_6-C_{10}$ carbocyclic aryl, halogen atoms, nitro groups, cyano groups, carboxy groups, alkoxycarbonyl groups wherein the alkoxy part is $C_1-C_6$ alkoxy, amino groups, $C_1-C_6$ alkylamino groups, dialkylamino groups wherein each alkyl part is $C_1-C_6$ alkyl, aliphatic or carbocyclic aromatic carboxylic acylamino groups, carbamoyl groups, alkylcarbamoyl groups where the alkyl part is $C_1-C_6$ alkyl, dialkylcarbamoyl groups where each alkyl part is $C_1-C_6$ alkyl, $C_1-C_6$ alkylthio groups, $C_6-C_{10}$ carbocyclic arylthio groups, $C_1-C_6$ alkylsulfonyl groups and $C_6-C_{10}$ carbocyclic arylsulfonyl groups wherein the aryl part is unsubstituted for has from 1 to 3 $C_1-C_6$ alkyl substituents;

$R^2$, $R^3$, $R^4$ and $R^5$ are independently selected from the group consisting of hydrogen atoms, $C_1-C_{10}$ alkyl groups, $C_3-C_8$ cycloalkyl groups, aralkyl groups wherein the alkyl part is $C_1-C_6$ alkyl and the aryl part is $C_6-C_{10}$ carbocyclic aryl, $C_6-C_{14}$ carbocyclic aryl groups, $C_1-C_6$ alkyl groups having a heterocyclic substituent wherein the heterocyclic part has from 5 to 10 ring atoms of which from 1 to 5 are hetero-atoms selected from the group consisting of nitrogen, sulfur and oxygen atoms, and heterocyclic groups having from 5 to 14 ring atoms of which from 1 to 5 are hetero-atoms selected from the group consisting of nitrogen, sulfur and oxygen atoms, provided that $R^2$, $R^3$, $R^4$ and $R^5$ do not all represent hydrogen atoms, said groups representing by $R^2$, $R^3$, $R^4$ and $R^5$ being unsubstituted or having at least one substituent selected from the group consisting of the substituents defined in (a) above, or $R^2$ and $R^3$, $R^4$ and $R^5$ or $R^2$ and $R^4$ together form a saturated carbocyclic or heterocyclic ring having from 3 to 6 ring atoms, of which, in said heterocyclic ring, from 1 to 3 are hetero-atoms selected from the group consisting of nitrogen, sulfur and oxygen atoms, or $R^2$ and $R^3$, $R^4$ and $R^5$ or $R^2$ and $R^4$ together form a saturated carbocyclic ring having 5 or 6 ring atoms, which ring is fused with a $C_6$–$C_{10}$ carbocyclic aryl system;

A represents a direct carbon-carbon bond, a methylene group, an ethylene group, an oxymethyl group or a thiomethyl group;

B represents a $C_1$–$C_4$ alkylene or alkylidene group or a $C_3$–$C_6$ cycloalkylene or cycloalkylidene group n is 0, 1 or 2;

and pharmaceutically acceptable salts and esters thereof.

The invention also provides a pharmaceutical composition for the treatment of angiotensin-induced hypertension, which composition comprises a hypotensive agent in admixture with a pharmaceutically acceptable carrier or diluent, wherein said hypotensive agent is selected from the group consisting of compounds of formula (I) and pharmaceutically acceptable salts and esters thereof.

The invention still further provides a method of treating angiotensin-induced hypertension in a mammal, which may be human or non-human, by administering to said mammal an effective amount of a hypotensive agent, wherein said hypotensive agent is selected from the group consisting of compounds of formula (I) and pharmaceutically acceptable salts and esters thereof.

The invention also provides processes for preparing the compounds of the invention, which are described in more detail hereafter.

DETAILED DESCRIPTION OF INVENTION

In the compounds of the invention, $R^1$ may represent an alkyl group, a cycloalkyl group, an aryl group or a heterocyclic group.

Where $R^1$ represents an alkyl group, this may be a straight or branched chain alkyl group which has from 1 to 10, more preferably from 1 to 8, carbon atoms. Examples of such groups include the methyl, ethyl, propyl, isopropyl, butyl, isobutyl, t-butyl, pentyl, neopentyl, hexyl and octyl groups.

Where $R^1$ represents a cycloalkyl group, this has from 3 to 8, more preferably from 5 to 7, ring carbon atoms and examples of such groups include the cyclopentyl, cyclohexyl and cycloheptyl groups.

Where $R^1$ represents an aryl group, this is preferably a carbocyclic aryl group which has from 6 to 10 ring carbon atoms and may comprise a single or multiple (fused) ring system. Preferred examples of such aryl groups include the phenyl, 1-naphthyl and 2-naphthyl groups.

Where $R^1$ represents a partially hydrogenated carbocyclic aryl group, this is preferably a polycyclic (more preferably bicyclic) system having from 8 to 14, more preferably 9 to 14 and most preferably 9 or 10 ring carbon atoms. In particular, we prefer that it should consist of a fully aromatic ring fused to another ring, of which all carbon atoms other than those at the points of fusion are fully saturated. Accordingly, the most preferred such groups are the indanyl and 1,2,3,4-tetrahydronaphthyl groups. We prefer that the group should be attached to the bond or group represented by A via one of the saturated carbon atoms. Accordingly, preferred groups are the 2-indanyl, 1-(1,2,3,4-tetrahydronaphthyl) and 2-(1,2,3,4-tetrahydronaphthyl) groups.

Where $R^1$ represents a heterocyclic group, this may be a saturated or unsaturated heterocyclic group and may be monocyclic or polycyclic (preferably bicyclic); it preferably has from 5 to 10 ring atoms, of which from 1 to 5, more preferably from 1 to 3, are hetero-atoms selected from the group consisting of nitrogen, oxygen and sulfur atoms. Examples of such heterocyclic groups include the tetrahydrofuranyl, tetrahydrothienyl, tetrahydropyranyl, morpholinyl, furyl, thienyl, imidazolyl, thiazolyl, oxazolyl, isoxazolyl, pyridyl, quinolyl, isoquinolyl and indolyl groups.

These groups represented by $R^1$ may be unsubstituted or may have at least one substituent selected from the following groups:

except where the group represented by $R^1$ is itself an alkyl group, $C_1$–$C_6$, preferably $C_1$–$C_4$, alkyl groups, for example the methyl, ethyl, propyl, isopropyl, butyl, isobutyl and t-butyl groups;

$C_6$–$C_{10}$ carbocyclic aryl groups, which may be monocyclic or fused polycyclic (preferably bicyclic) groups and which may themselves be substituted as here defined, particularly the phenyl, 1-naphthyl or 2-naphthyl groups;

aralkyl groups in which the alkyl part is $C_1$–$C_6$ alkyl and the aryl part is $C_6$–$C_{10}$ carbocyclic aryl, for example the benzyl, phenethyl, 1-naphthylmethyl, 2-naphthylmethyl and 3-phenylpropyl groups;

the hydroxy group;

$C_1$–$C_6$, preferably $C_1$–$C_4$, alkoxy groups, for example the methoxy, ethoxy, propoxy, isopropoxy, butoxy or isobutoxy groups;

aralkyloxy groups, in which the aryl part is $C_6$–$C_{10}$ carbocyclic aryl, more preferably phenyl, and the alkyl part is $C_1$–$C_6$ alkyl, more preferably $C_1$–$C_2$ alkyl and most preferably methyl, for example the benzyloxy group;

aryloxy groups, in which the aryl part is $C_6$–$C_{10}$ carbocyclic aryl, more preferably phenyl, for example the phenoxy group;

halogen atoms, for example the fluorine, chlorine and bromine atoms;

the nitro, cyano and carboxy groups;

alkoxycarbonyl groups, in which the alkoxy part is $C_1$–$C_6$, more preferably $C_1$–$C_3$, alkoxy, for example the methoxycarbonyl and ethoxycarbonyl groups;

the amino group;

alkylamino groups in which the alkyl part is $C_1$–$C_6$, more preferably $C_1$–$C_4$, alkyl, for example the methylamino and ethylamino groups;

dialkylamino groups, in which each alkyl part is $C_1$–$C_6$, preferably $C_1$–$C_4$, more preferably $C_1$–$C_3$, alkyl, for example the dimethylamino or diethylamino groups;

acylamino groups, which can be aliphatic acylamino groups, preferably having from 1 to 7, more preferably from 1 to 4, carbon atoms or carbocyclic aromatic carboxylic acylamino groups in which the aromatic part is $C_6$–$C_{10}$ carbocyclic aryl and is more preferably a phenyl group, for example the acetamido and benzamido groups;

the carbamoyl group;

the alkylcarbamoyl and dialkylcarbamoyl groups, in which the or each alkyl part is $C_1-C_6$, more preferably $C_1-C_4$ and most preferably $C_1-C_3$, alkyl, for example the N-methylcarbamoyl, N-ethylcarbamoyl, dimethylcarbamoyl or diethylcarbamoyl groups;

$C_1-C_6$, more preferably $C_1-C_4$, alkylthio groups, for example the methylthio or ethylthio groups;

arylthio groups in which the aryl part is $C_6-C_{10}$ carbocyclic aryl, more preferably phenyl, for example the phenylthio groups;

$C_1-C_6$, more preferably $C_1-C_4$ alkylsulfonyl groups, for example the methanesulfonyl or ethanesulfonyl groups;

arylsulfonyl groups in which the aryl part is $C_6-C_{10}$ carbocyclic aryl, more preferably phenyl, for example the benzenesulfonyl group.

Where the group represented by $R^1$ is substituted, the maximum number of substituents will, of course, depend upon the size of the group to be substituted and the steric effects exerted by the substituents; if the group represented by $R^1$ is small, for example a lower alkyl group, and the substituent bulky, then steric hindrance may limit the number of potential substituents; at the other extreme, if the substituent is small, the number of substituents may only be limited by the number of available valencies of the atoms in the group represented by $R^1$. For example, where the substituent is a fluorine or chlorine atom, $R^1$ could represent a perfluoroalkyl or perchloroalkyl group. However, in general, from 1 to 3 substituents are preferred, although it should be appreciated that more may be appropriate in specific cases, as is well recognized by those skilled in the chemical arts.

Where $R^2$, $R^3$, $R^4$ or $R^5$ represents an alkyl group, this is a $C_1-C_{10}$ alkyl group, which may be a straight or branched chain group, more preferably having from 1 to 8 carbon atoms. Examples of such groups include the methyl, ethyl, propyl, isopropyl, butyl, isobutyl, sec-butyl, t-butyl, pentyl, isopentyl, neopentyl, hexyl, heptyl and octyl groups.

Where $R^2$, $R^3$, $R^4$ or $R^5$ represents a cycloalkyl group, this has from 3 to 8, more preferably from 5 to 7, ring carbon atoms and preferred such groups include the cyclopentyl, cyclohexyl and cycloheptyl groups.

Where $R^2$, $R^3$, $R^4$ or $R^5$ represents an aralkyl group, the alkyl part is a $C_1-C_6$ alkyl group (examples being those $C_1-C_6$ alkyl groups included amongst the examples of alkyl groups which may be represented by $R^1$) and the aryl part is a $C_6-C_{10}$ carbocyclic aryl group (examples of which are those groups given as examples of aryl groups which may be represented by $R^1$). Preferred aralkyl groups are the benzyl, phenethyl and 3-phenylpropyl groups.

Where $R^2$, $R^3$, $R^4$ or $R^5$ represents a carbocyclic aryl group, this preferably has from 6 to 10 ring carbon atoms and may be a monocyclic or fused polycyclic (normally bicyclic) group. Preferred examples include the phenyl, 1-naphthyl and 2-naphthyl groups.

Where $R^2$, $R^3$, $R^4$ or $R^5$ represents a heterocyclic group or an alkyl group having a heterocyclic substituent, the heterocyclic group has from 5 to 10, more preferably from 5 to 8, ring atoms, of which from 1 to 5, more preferably from 1 to 3, are hetero-atoms selected from the group consisting of nitrogen, sulfur and oxygen atoms. The heterocyclic group may be saturated, unsaturated or partially saturated, preferably saturated or unsaturated, and may be monocyclic or fused polycyclic (preferably bicyclic). Examples of such groups include the tetrahydrofuranyl, tetrahydrothienyl, tetrahydropyranyl, morpholinyl, furyl, thienyl, imidazolyl, thiazolyl, oxazolyl, isoxazolyl, 1,3,4-oxadiazolyl, 1,3,4-thiadiazolyl, pyridyl, quinolyl, isoquinolyl and indolyl groups. Where $R^2$, $R^3$, $R^4$ or $R^5$ represents an alkyl group having such a heterocyclic substituent, the alkyl group itself is a $C_1-C_6$ alkyl group (which may be a straight or branched chain group) and examples of such groups are the $C_1-C_6$ groups amongst those given as examples of alkyl groups which may be represented by $R^1$.

Instead of the groups described above, $R^2$, $R^3$, $R^4$ or $R^5$ can represent a hydrogen atom, however, no more than 3 of these symbols may represent hydrogen atoms, in other words there must be at least 1 group other than hydrogen at the 2- or 3-, preferably the 2-, positions. Those compounds are particularly preferred where $R^3$ and $R^5$ both represent hydrogen atoms, whilst one of $R^2$ and $R^4$, preferably $R^4$, also represents a hydrogen atom and the other of $R^2$ and $R^4$ represents one of the aforementioned groups.

The groups defined above for $R^2$, $R^3$, $R^4$ and $R^5$ may be unsubstituted or may have at least one substituent selected from those substituents defined in (a) above as substituents on the groups represented by $R^1$. As with $R^1$, where any group represented by $R^2$, $R^3$, $R^4$ or $R^5$ is substituted, the number of substituents is only limited by steric considerations, which, of course, vary depending upon the nature of the substituent and the substituted groups and so cannot be defined in general terms. Normally, however, it is convenient, where such groups are substituted, to have from 1 to 3 substituents, but it should be appreciated that this does not, in any sense, represent a practical limit.

As an alternative, $R^2$ and $R^3$ and/or $R^4$ and $R^5$ or $R^2$ and $R^4$ may together form a saturated carbocyclic or heterocyclic ring having from 3 to 6 ring atoms or they may together form a saturated carbocyclic ring having 5 or 6 ring atoms, the saturated carbocyclic ring being fused with a $C_6-C_{10}$ carbocyclic aryl system. Examples of such groups include the cyclopropane, cyclopentane, cyclohexane, tetrahydrofuran, tetrahydropyran, tetrahydrothiophene, pyrrolidine, piperidine, indane and 1,2,3,4-tetrahydronaphthalene groups.

The symbol A can represent a direct single bond between the group represented by $R^1$ and the carbon atom of the group CH—NH— at the 6-position of the thiazepine ring; alternatively, it can represent a methylene group, an ethylene group, an oxymethyl (—OCH$_2$—) group or a thiomethyl (—SCH$_2$—) group. We prefer that A should represent an ethylene group and more particularly prefer that the group represented by $R^1$—A should be:

a straight or branched chain alkyl group having from 4 to 9 carbon atoms, for example a butyl, isobutyl, pentyl, isopentyl, neopentyl, hexyl, octyl, isooctyl or nonyl group;

a 2-cycloalkylethyl group, in which the cycloalkyl part has 5 or 6 ring carbon atoms, for example a 2-cyclopentylethyl or 2-cyclohexylethyl group;

an aralkyl group having a total of from 7 to 12 carbon atoms, for example a benzyl, phenethyl, 1-naphthylmethyl, 2-naphthylmethyl, 2-(1-naphthyl)ethyl or 2-(2-naphthyl)ethyl group;

a phenoxymethyl or phenylthiomethyl group; or a heterocyclic-substituted ethyl group, for example a 2-(2-thienyl)ethyl, 2-(2-imidazolyl)ethyl or 2-(2-thiazolyl)ethyl group.

n may be 0, 1 or 2, but is most preferably 0.

B may represent a $C_1$–$C_4$ alkylene or alkylidene group or a $C_3$–$C_6$ cycloalkylene or cycloalkylidene group. Examples of such alkylene groups which may be represented by B are the methylene, ethylene, trimethylene and tetramethylene groups. Where B represents an alkylidene group, this may be an ethylidene, propylidene or butylidene group, preferably an ethylidene group. Where B represents a $C_3$–$C_6$ cycloalkylene or cycloalkylidene group, these may be the cyclopropylene, cyclopropylidene, cyclobutylene, cyclobutylidene, cyclopentylene, cyclopentylidene, cyclohexylene or cyclohexylidene groups, preferably the cyclopropylidene group.

The compounds of formula (I) have two free carboxy groups and can thus form mono- or di-esters with appropriate ester-forming groups. There is no practical limitation upon the nature of the ester-forming groups employed in this invention, beyond the practical consideration that, if the resulting compounds are in themselves to be used for the treatment of human beings or other animals, the resulting esters must be "pharmaceutically acceptable"; this, to the skilled man, means that the ester-forming groups must not, or must not to an unacceptable extent, reduce the activity or increase the toxicity of the compounds. Where the resulting compounds are not in themselves to be used as medicines but, instead, are to be used as intermediates in the preparation of other compounds, even this practical restriction does not apply and any ester appropriate to the intended preparative route may be formed.

The resulting compounds of the invention may be represented by the formula (Ia):

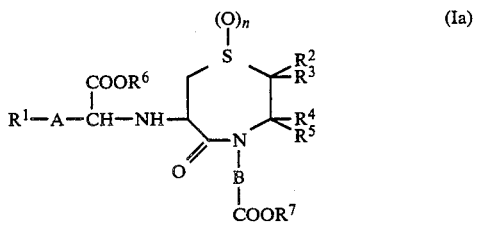

(wherein $R^1$–$R^5$, A, B and n are as defined above and $R^6$ and $R^7$, which are the same or different, each represents a hydrogen atom or a carboxy-protecting, preferably ester-forming, group). Preferably, $R^6$ and $R^7$ are the same or different and each represents a $C_1$–$C_{10}$ alkyl group, an aralkyl group in which the aryl part is a $C_6$–$C_{10}$ carbocyclic aryl group which is unsubstituted or substituted as defined in (b) below and the alkyl part is $C_1$–$C_6$ alkyl, a $C_6$–$C_{14}$ carbocyclic aryl group, a partially hydrogenated $C_6$–$C_{14}$ carbocyclic aryl group, a phthalidyl group or a trialkylsilyl group where each alkyl part is $C_1$–$C_6$ alkyl, said groups represented by $R^6$ and $R^7$ being unsubstituted or having at least one substituent selected from the group consisting of:

(b) halogen atoms, hydroxy groups, $C_1$–$C_6$ alkoxy groups, ($C_1$–$C_6$ alkoxy)-($C_1$–$C_3$ alkoxy) groups, aliphatic and carbocyclic aromatic carboxylic acyloxy groups, oxo groups, carboxy groups, alkoxycarbonyl groups where the alkoxy part is $C_1$–$C_6$ alkoxy, alkoxycarbonyloxy groups where the alkoxy part is $C_1$–$C_6$ alkoxy, aliphatic and carbocyclic aromatic carboxylic acylamino groups, nitro groups, cyano groups, amino groups, $C_1$–$C_6$ alkylamino groups, dialkylamino groups where each alkyl part is $C_1$–$C_6$ alkyl, $C_6$–$C_{10}$ carbocyclic arylamino groups, $C_1$–$C_6$ alkylthio groups, $C_6$–$C_{10}$ carbocyclic arylthio groups, $C_1$–$C_6$ alkylsulfonyl groups, $C_6$–$C_{10}$ carbocyclic arylsulfonyl groups and heterocyclic groups having from 5 to 14 ring atoms, of which from 1 to 5 are hetero-atoms selected from the group consisting of nitrogen, sulfur and oxygen atoms, said heterocyclic groups being unsubstituted or having at least one substituent selected from the group consisting of the substituents defined in (a) above.

Examples of such groups which may be represented by $R^6$ and $R^7$ include:

$C_1$–$C_6$ alkyl groups, such as the methyl, ethyl, propyl, isopropyl, butyl, isobutyl, t-butyl, pentyl and hexyl groups;

aralkyl and diarylalkyl groups, such as the benzyl and benzhydryl(diphenylmethyl) groups;

partially hydrogenated $C_6$–$C_{10}$ carbocyclic aryl groups, such as the 1-indanyl, 2-indanyl, 1-(1,2,3,4-tetrahydronaphthyl) and 2-(1,2,3,4-tetrahydronaphthyl) groups;

the phthalidyl group;

$C_6$–$C_{10}$ carbocyclic aryl groups, particularly the phenyl group;

trialkylsilyl groups, particularly the trimethylsilyl and t-butyldimethylsilyl groups; and such groups listed above having one or more substituents selected from the group consisting of alkyl, halogen, hydroxy, alkoxy, alkoxyalkoxy, acyloxy, oxo, carboxy, alkoxycarbonyl, alkoxycarbonyloxy, acylamino, nitro, cyano, amino, alkylamino, dialkylamino, arylamino, alkylthio, arylthio, alkylsulfonyl, arylsulfonyl and 2-oxo-1,3-dioxolen-4-yl (which may itself be substituted) substituents.

Where substituents are present, their number is only limited by steric considerations, which depend upon the size of the substituent and of the substituted group; however, in general, from 1 to 3 substituents would be present.

Examples of such substituted groups include the 2,2,2-trichloroethyl, 2-iodoethyl, 2-hydroxyethyl, 2,3-dihydroxypropyl, methoxymethyl, 2-methoxyethoxymethyl, p-methoxybenzyl, acetoxymethyl, 1-acetoxyethyl, pivaloyloxymethyl, phenacyl, methoxycarbonylmethyl, ethoxycarbonylmethyl, 1-(ethoxycarbonyloxy)ethyl, p-nitrobenzyl, 2-cyanoethyl, methylthiomethyl, ethylthiomethyl, phenylthiomethyl, 2-methanesulfonylethyl, 2-benzenesulfonylethyl, (5-methyl-2-oxo-1,3-dioxolen-4-yl)methyl and (5-phenyl-2-oxo-1,3-dioxolen-4-yl)methyl groups.

Preferred classes of compounds of the present invention are those compounds of formula I(a) in which the substituents are defined as follows:

(A) Compounds in which:

$R^1$ represents a phenyl group or a $C_2$–$C_7$ alkyl group;

$R^2$ and $R^4$ are the same or different and each represents a hydrogen atom, a $C_1$–$C_{10}$ alkyl group, a phenyl group, a naphthyl group, a $C_3$–$C_8$ cycloalkyl group or a heterocyclic group having from 5 to 10 ring atoms, of which from 1 to 3 are hetero-atoms selected from the group consisting of nitrogen, oxygen and sulfur atoms;

$R^3$ and $R^5$ both represent hydrogen atoms;

A represents an ethylene group;

B represents a methylene group; and n is 0;

(A') $R^2$ and $R^4$ are the same or different and each represents a hydrogen atom, a $C_1$–$C_{10}$ alkyl group, a phenyl group, a naphthyl group, a $C_3$–$C_8$ cycloalkyl group or a heterocyclic group having 5 or 6 ring atoms, of which from 1 to 3 are hetero-atoms selected from the group consisting of nitrogen, oxygen and sulfur atoms; and $R^1$, $R^3$, $R^5$, A, B and n are as defined in (A) above;

(B) Compounds as defined in (A) above in which $R^6$ represents a hydrogen atom, a $C_1$–$C_{10}$ alkyl group or an aralkyl group in which the aryl part is a $C_6$–$C_{10}$ carbocyclic aryl group and the alkyl part is a $C_1$–$C_6$ alkyl group;

(C) Compounds in which:
$R^1$ represents a phenyl group or a $C_2$–$C_7$ alkyl group;
$R^2$ represents a $C_1$–$C_{10}$ alkyl group, a phenyl group, a naphthyl group, a $C_3$–$C_8$ cycloalkyl group or a heterocyclic group having 5 or 6 ring atoms of which from 1 to 3 are hetero-atoms selected from the group consisting of nitrogen, oxygen and sulfur atoms;
$R^3$, $R^4$ and $R^5$ all represent hydrogen atoms;
$R^6$ represents a hydrogen atom, a $C_1$–$C_{10}$ alkyl group or an aralkyl group of which the aryl part is a $C_6$–$C_{10}$ carbocyclic aryl group and the alkyl part is a $C_1$–$C_6$ alkyl group;
$R^7$ represents a hydrogen atom, a ($C_1$–$C_4$ alkoxy)carbonyloxy($C_1$–$C_4$ alkyl) group, a ($C_2$–$C_5$ alkanoyl)oxy($C_1$–$C_4$ alkyl) group, a (5-alkyl-2-oxo-1,3-dioxolen-4-yl)alkyl group in which each alkyl group has from 1 to 4 carbon atoms, a (5-phenyl-2-oxo-1,3-dioxolen-4-yl)alkyl group in which the alkyl part has from 1 to 4 carbon atoms, or a phthalidyl group;
A represents an ethylene group;
B represents a methylene group; and
n is 0;

(D) Compounds in which:
$R^1$ represents a phenyl group or a $C_2$–$C_7$ alkyl groups;
$R^2$ represents a heterocyclic group having 5 or 6 ring atoms of which from 1 to 3 are hetero-atoms selected from the group consisting of nitrogen, oxygen and sulfur atoms;
$R^3$, $R^4$ and $R^5$ all represent hydrogen atoms;
$R^6$ represents a hydrogen atom, a $C_1$–$C_6$ alkyl group or an aralkyl group of which the aryl part is a $C_6$–$C_{10}$ carbocyclic aryl group and the alkyl part is a $C_1$–$C_4$ alkyl group;
$R^7$ represents a hydrogen atom, a ($C_1$–$C_4$ alkoxy)carbonyloxy($C_1$–$C_4$ alkyl) group, a ($C_2$–$C_5$ alkanoyl)oxy($C_1$–$C_4$ alkyl) group, a (5-alkyl-2-oxo-1,3-dioxolen-4-yl)alkyl group in which each alkyl part has from 1 to 4 carbon atoms, a (5-phenyl-2-oxo-1,3-dioxolen-4-yl)alkyl group in which the alkyl part has from 1 to 4 carbon atoms or a phthalidyl group;
A represents an ethylene group;
B represents a methylene group; and
n is 0;

(E) Compounds in which:
$R^1$ represents a phenyl group or a $C_2$–$C_7$ alkyl group;
$R^2$ represents a heterocyclic group having 5 ring atoms, of which from 1 to 3 are hetero-atoms selected from the group consisting of nitrogen, oxygen and sulfur atoms;
$R^3$, $R^4$ and $R^5$ all represent hydrogen atoms;
$R^6$ represents a hydrogen atom, a $C_1$–$C_6$ alkyl group or an aralkyl group of which the aryl part is a $C_6$–$C_{10}$ carbocyclic aryl group and the alkyl part is a $C_1$–$C_4$ alkyl group;
$R^7$ represents a hydrogen atom, a ($C_1$–$C_4$ alkoxy)carbonyloxy($C_1$–$C_4$ alkyl) group, a ($C_2$–$C_5$ alkanoyl)oxy($C_1$–$C_4$ alkyl) group, a (5-alkyl-2-oxo-1,3-dioxolen-4-yl)alkyl group in which each alkyl part has from 1 to 4 carbon atoms, a (5-phenyl-2-oxo-1,3-dioxolen-4-yl)alkyl group in which the alkyl part has from 1 to 4 carbon atoms or a phthalidyl group;
A represents an ethylene group;
B represents a methylene group; and
n is 0;

(F) Compounds in which:
$R^1$ represents a phenyl group or a $C_2$–$C_7$ alkyl group;
$R^2$ represents a thienyl group or furyl group;
$R^3$, $R^4$ and $R^5$ all represent hydrogen atoms;
$R^6$ represents a hydrogen atom, a $C_1$–$C_4$ alkyl group, a benzyl group or phenylethyl group;
$R^7$ represents a hydrogen atom, a ($C_2$–$C_5$ alkanoyl)oxy($C_1$–$C_3$ alkyl) group, a ($C_1$–$C_4$ alkoxy)carbonyloxy($C_1$–$C_3$ alkyl) group, a (2-oxo-1,3-dioxolen-4-yl)alkyl group in which the alkyl is $C_1$–$C_3$ alkyl and which has a $C_1$–$C_4$ alkyl or phenyl substituent at the 5-position, or a phthalidyl group;
A represents an ethylene group;
B represents a methylene group; and
n is 0;

(G) Compounds in which:
$R^1$ represents a phenyl group or a $C_2$–$C_7$ alkyl group;
$R^2$ represents a 2-thienyl group, a 3-thienyl group or a 2-furyl group;
$R^3$, $R^4$ and $R^5$ all represent hydrogen atoms;
$R^6$ represents a hydrogen atom, a $C_1$–$C_4$ alkyl group or a benzyl group;
$R^7$ represents a hydrogen atom, a ($C_2$–$C_5$ alkanoyl)oxy($C_1$–$C_3$ alkyl) group, a ($C_1$–$C_4$ alkoxy)carbonyloxy($C_1$–$C_2$ alkyl) group, a (5-methyl-2-oxo-1,3-dioxolen-4-yl)methyl group or a (5-phenyl-2-oxo-1,3-dioxolen-4-yl)methyl group;
A represents an ethylene group;
B represents a methylene group; and
n is 0;

(H) Compounds in which:
$R^1$ represents a phenyl group or a $C_2$–$C_7$ alkyl group;
$R^2$ represents a phenyl group, a naphthyl group, a $C_1$–$C_6$ alkyl group or a $C_3$–$C_8$ cycloalkyl group;
$R^3$, $R^4$ and $R^5$ all represent hydrogen atoms;
$R^6$ represents a hydrogen atom, a $C_1$–$C_6$ alkyl group or an aralkyl group of which the aryl part is a $C_6$–$C_{10}$ carbocyclic aryl group and the alkyl part is a $C_1$–$C_4$ alkyl group;
$R^7$ represents a hydrogen atom, an acyloxyalkyl group, an alkoxycarbonyloxyalkyl group, a (2-oxo-1,3-dioxolen-4-yl)alkyl group where the alkyl group is $C_1$–$C_4$ and which has a $C_1$–$C_4$ alkyl or phenyl substituent at the 5-position, or a phthalidyl group;
A represents an ethylene group;
B represents a methylene group; and
n is 0;

(I) Compounds in which:
$R^1$ represents a phenyl group or a $C_2$–$C_7$ alkyl group;
$R^2$ represents a naphthyl group;
$R^3$, $R^4$ and $R^5$ all represent hydrogen atoms;
$R^6$ represents a hydrogen atom, a $C_1$–$C_6$ alkyl group or an aralkyl group of which the aryl part is a $C_6$–$C_{10}$ carbocyclic aryl group and the alkyl part is a $C_1$–$C_4$ alkyl group;
$R^7$ represents a hydrogen atom, an acyloxyalkyl group, an alkoxycarbonyloxyalkyl group, a (2-oxo-1,3-dioxolen-4-yl)alkyl group where the alkyl group is $C_1$–$C_4$ and which has a $C_1$–$C_4$ alkyl or phenyl substituent at the 5-position, or a phthalidyl group;

A represents an ethylene group;
B represents a methylene group; and
n is 0;

(J) Compounds in which:
$R^1$ represents a phenyl group or a $C_2$–$C_7$ alkyl group;
$R^2$, $R^3$ and $R^5$ all represent hydrogen atoms;
$R^4$ represents a heterocyclic group having 5 or 6 ring atoms, of which from 1 to 3 are hetero-atoms selected from the group consisting of nitrogen, oxygen and sulfur atoms;
$R^6$ represents a hydrogen atom, a $C_1$–$C_4$ alkyl group, a benzyl group or a phenylethyl group;
$R^7$ represents a hydrogen atom, an acyloxyalkyl group, an alkoxycarbonyloxyalkyl group, a (5-alkyl-2-oxo-1,3-dioxolen-4-yl)alkyl group in which each alkyl group is $C_1$–$C_4$, a (5-phenyl-2-oxo-1,3-dioxolen-4-yl)alkyl group in which the alkyl part is $C_1$–$C_4$ or a phthalidyl group;
A represents an ethylene group;
B represents a methylene group; and
n is 0;

(K) Compounds in which:
$R^1$ represents a phenyl group or a $C_2$–$C_7$ alkyl group;
$R^2$, $R^3$ and $R^5$ all represent hydrogen atoms;
$R^4$ represents a $C_1$–$C_6$ alkyl group, a phenyl group, a naphthyl group or a $C_3$–$C_8$ cycloalkyl group;
$R^6$ represents a hydrogen atom, a $C_1$–$C_4$ alkyl group, a benzyl group or a phenylethyl group;
$R^7$ represents a hydrogen atom, a ($C_2$–$C_5$ alkanoyl)oxy($C_1$–$C_3$ alkyl) group, a ($C_1$–$C_4$ alkoxy)carbonyloxy($C_1$–$C_3$ alkyl) group, a (5-alkyl-2-oxo-1,3-dioxolen-4-yl)alkyl group in which each alkyl part is $C_1$–$C_3$, a (5-phenyl-2-oxo-1,3-dioxolen-4-yl)alkyl group in which the alkyl part is $C_1$–$C_3$ or a phthalidyl group;
A represents an ethylene group;
B represents a methylene group; and
n is 0.

Where $R^6$ or $R^7$ represents an ester-forming group, these are preferably either carboxy-protecting groups which are commonly used in organic chemical synthesis, such as the t-butyl, methoxymethyl, 2,2,2-trichloroethyl, benzyl, p-methoxybenzyl or benzhydryl groups, or a protecting group which is easily convertible to a free carboxy group in vivo, such as the acetoxymethyl, pivaloylmethyl, 1-(ethoxycarbonyloxy)-ethyl, phthalidyl or (5-methyl-2-oxo-1,3-dioxolen-4-yl)-methyl groups.

Where the compounds of the invention contain one or two free carboxy groups, these compounds may also form salts with bases; the nature of the cation of the resulting salt is not critical to the present invention and, where the resulting compounds are for use as medicines, is only limited to the extent that the resulting cation must be pharmaceutically acceptable; where the compound is subsequently to be used as an intermediate for the production of another compound, even this restriction is not applicable. Of course, there are practical constraints, such as cost and availability of the bases used to form the salts, but these constraints vary from time to time and are irrelevant to the essence of the present invention. Examples of suitable salts include: alkali metal salts, for example sodium or potassium salts; alkaline earth metal salts, for example calcium or magnesium salts; ammonium salts; salts with organic bases, for example triethylamine, dicyclohexylamine, cinchonine, guanidine or quinine salts; and salts with basic amino acids, for example lysine or arginine salts.

The compounds of the invention also contain a nitrogen atom which can potentially exert a basic effect and the compounds can thus also form acid addition salts. Where the compounds are to be used as medicines, the nature of such salts is only limited to the extent that the resulting compound should be pharmaceutically acceptable; where the compound is to be used as an intermediate, this criterion does not apply and any acid may be employed. Examples of suitable acids include inorganic acids, such as hydrogen halides, (for example hydrochloric acid or hydrobromic acid), sulfuric acid, phosphoric acid or nitric acid; organic carboxylic acids, for example oxalic acid, maleic acid, fumaric acid, tartaric acid or citric acid; and organic sulfonic acids, such as methanesulfonic acid or benzenesulfonic acid.

Examples of certain compounds of the present invention are given in the following list:
1. α-[6-(1-ethoxycarbonylnonylamino)-5-oxo-3-phenylperhydro-1,4-thiazepin-4-yl]acetic acid
2. α-[6-(1-carboxynonylamino)-5-oxo-3-phenylperhydro-1,4-thiazepin-4-yl]acetic acid
3. α-[6-(3-cyclohexyl-1-ethoxycarbonylpropylamino)-5-oxo-3-phenylperhydro-1,4-thiazepin-4-yl]acetic acid
4. α-[6-(1-carboxy-3-cyclohexylpropylamino)-5-oxo-3-phenylperhydro-1,4-thiazepin-4-yl]acetic acid
5. 2-[6-(1-ethoxycarbonylnonylamino)-5-oxo-3-phenylperhydro-1,4-thiazepin-4-yl]propionic acid
6. 2-[6-(1-carboxynonylamino)-5-oxo-3-phenylperhydro-1,4-thiazepin-4-yl]propionic acid
7. 2-[6-(1-ethoxycarbonyl-3-phenylpropylamino)-3-isopropyl-5-oxoperhydro-1,4-thiazepin-4-yl]propionic acid
8. 2-[6-(1-carboxy-3-phenylpropylamino)-3-isopropyl-5-oxoperhydro-1,4-thiazepin-4-yl]propionic acid
9. 2-[3-sec-butyl-6-(1-ethoxycarbonyl-3-phenylpropylamino)-5-oxoperhydro-1,4-thiazepin-4-yl]propionic acid
10. 2-[3-sec-butyl-6-(1-carboxy-3-phenylpropylamino)-5-oxoperhydro-1,4-thiazepin-4-yl]propionic acid
11. α-[6-(1-ethoxycarbonyl-3-phenylpropylamino)-3-isobutyl-5-oxoperhydro-1,4-thiazepin-4-yl]acetic acid
12. α-[6-(1-carboxy-3-phenylpropylamino)-3-isobutyl-5-oxoperhydro-1,4-thiazepin-4-yl]acetic acid
13. α-[6-(1-ethoxycarbonyl-3-phenylpropylamino)-3-(2-methylthioethyl)-5-oxoperhydro-1,4-thiazepin-4-yl]acetic acid
14. α-[6-(1-carboxy-3-phenylpropylamino)-3-(2-methylthioethyl)-5-oxoperhydro-1,4-thiazepin-4-yl]acetic acid
15. α-[3-cyclohexyl-6-(1-ethoxycarbonyl-3-phenylpropylamino)-5-oxoperhydro-1,4-thiazepin-4-yl]acetic acid
16. α-[3-cyclohexyl-6-(1-carboxy-3-phenylpropylamino)-5-oxoperhydro-1,4-thiazepin-4-yl]acetic acid
17. α-[3-benzyl-6-(1-ethoxycarbonyl-3-phenylpropylamino)-5-oxoperhydro-1,4-thiazepin-4-yl]acetic acid
18. α-[3-benzyl-6-(1-carboxy-3-phenylpropylamino)-5-oxoperhydro-1,4-thiazepin-4-yl]acetic acid
19. α-[3-benzyl-6-(1-ethoxycarbonyl-3-phenylpropylamino)-1,5-dioxoperhydro-1,4-thiazepin-4-yl]acetic acid
20. α-[3-benzyl-6-(1-ethoxycarbonyl-3-phenylpropylamino)-1,1,5-trioxoperhydro-1,4-thiazepin-4-yl]acetic acid 21. α-[3-benzyl-6-(1-butoxycarbonyl-3-phenylpropylamino)-5-oxoperhydro-1,4-thiazepin-4-yl]acetic acid
22. 2-[3-benzyl-6-(1-ethoxycarbonyl-3-phenylpropylamino)-5-oxoperhydro-1,4-thiazepin-4-yl]propionic acid
23. α-[2-benzyl-6-(1-ethoxycarbonyl-3-phenylpropylamino)-5-oxoperhydro-1,4-thiazepin-4-yl]acetic acid
24. α-[2-benzyl-6-(1-carboxy-3-phenylpropylamino)-5-oxoperhydro-1,4-thiazepin-4-yl]acetic acid
25. α-[6-(1-ethoxycarbonyl-3-phenylpropylamino)-3-p-hydroxybenzyl-5-oxoperhydro-1,4-thiazepin-4-yl]acetic acid
26. α-[6-(1-carboxy-3-phenylpropylamino)-3-p-hydroxybenzyl-5-oxoperhydro-1,4-thiazepin-4-yl]acetic acid
27. α-[6-(1-ethoxycarbonyl-3-phenylpropylamino)-5-oxo-3-phenylperhydro-1,4-thiazepin-4-yl]acetic acid
28. α-[6-(1-carboxy-3-phenylpropylamino)-5-oxo-3-phenylperhydro-1,4-thiazepin-4-yl]acetic acid
29. α-[6-(1-ethoxycarbonyl-3-phenylpropylamino)-5-oxo-2-phenylperhydro-1,4-thiazepin-4-yl]acetic acid
30. α-[6-(1-carboxy-3-phenylpropylamino)-5-oxo-2-phenylperhydro-1,4-thiazepin-4-yl]acetic acid
31. α-[6-(1-ethoxycarbonyl-3-phenylpropylamino)-3-(2-naphthyl)-5-oxoperhydro-1,4-thiazepin-4-yl]acetic acid
32. α-[6-(1-carboxy-3-phenylpropylamino)-3-(2-naphthyl)-5-oxoperhydro-1,4-thiazepin-4-yl]acetic acid
33. α-[6-(1-ethoxycarbonyl-3-phenylpropylamino)-3-(1-naphthyl)-5-oxoperhydro-1,4-thiazepin-4-yl]acetic acid
34. α-[6-(1-carboxy-3-phenylpropylamino)-3-(1-naphthyl)-5-oxoperhydro-1,4-thiazepin-4-yl]acetic acid
35. α-[6-(1-ethoxycarbonyl-3-phenylpropylamino)-3-(2-indolylmethyl)-5-oxoperhydro-1,4-thiazepin-4-yl]acetic acid
36. α-[6-(1-carboxy-3-phenylpropylamino)-3-(2-indolylmethyl)-5-oxoperhydro-1,4-thiazepin-4-yl]acetic acid
37. α-[6-(1-ethoxycarbonyl-3-phenylpropylamino)-3-(2-imidazolylmethyl)-5-oxoperhydro-1,4-thiazepin-4-yl]acetic acid
38. α-[6-(1-carboxy-3-phenylpropylamino)-3-(2-imidazolylmethyl)-5-oxoperhydro-1,4-thiazepin-4-yl]acetic acid
39. α-[6-(1-ethoxycarbonyl-3-phenylpropylamino)-5-oxo-3-(2-thienyl)perhydro-1,4-thiazepin-4-yl]acetic acid
40. α-[6-(1-carboxy-3-phenylpropylamino)-5-oxo-3-(2-thienyl)perhydro-1,4-thiazepin-4-yl]acetic acid
41. α-[6-(1-ethoxycarbonyl-3-phenylpropylamino)-5-oxo-3-(1,3-thiazol-2-yl)perhydro-1,4-thiazepin-4-yl]acetic acid
42. α-[6-(1-carboxy-3-phenylpropylamino)-5-oxo-3-(1,3-thiazol-2-yl)perhydro-1,4-thiazepin-4-yl]acetic acid
43. α-[6-(1-ethoxycarbonyl-3-phenylpropylamino)-5-oxo-3-(2-pyridyl)perhydro-1,4-thiazepin-4-yl]acetic acid
44. α-[6-(1-carboxy-3-phenylpropylamino)-5-oxo-3-(2-pyridyl)perhydro-1,4-thiazepin-4-yl]acetic acid
45. α-[3-(1-ethoxycarbonyl-3-phenylpropylamino)-4-oxoperhydro-1,5-benzothiazepin-5-yl]acetic acid
46. α-[3-(1-carboxy-3-phenylpropylamino)-4-oxoperhydro-1,5-benzothiazepin-5-yl]acetic acid
47. α-[6-(1-ethoxycarbonyl-3-phenylpropylamino)-5-oxoperhydro-1,4-thiazepine-3-spiro-1'-cyclopentan-4-yl]acetic acid
48. α-[6-(1-carboxy-3-phenylpropylamino)-5-oxoperhydro-1,4-thiazepine-3-spiro-1'-cyclopentan-4-yl]acetic acid
49. α-[6-(1-ethoxycarbonyl-3-phenylpropylamino)-5-oxo-2,3,4,5,6,7-hexahydro-1,4-thiazepine-3-spiro-2'-indan-4-yl]acetic acid
50. α-[6-(1-carboxy-3-phenylpropylamino)-5-oxo-2,3,4,5,6,7-hexahydro-1,4-thiazepine-3-spiro-2'-indan-4-yl]acetic acid
51. α-[6-(1-ethoxycarbonyl-3-phenylpropylamino)-5-oxoperhydro-1,4-thiazepine-3-spiro-1'-cyclohexan-4-yl]acetic acid
52. α-[6-(1-carboxy-3-phenylpropylamino)-5-oxoperhydro-1,4-thiazepine-3-spiro-1'-cyclohexan-4-yl]acetic acid
53. α-[6-(1-ethoxycarbonyl-3-phenylpropylamino)-5-oxo-1',2,2',3,3',4,4',5,6,7-decahydro-1,4-thiazepine-3-spiro-2'-naphthalen-4-yl]acetic acid
54. α-[6-(1-carboxy-3-phenylpropylamino)-5-oxo-1',2,2',3,3',4,4',5,6,7-decahydro-1,4-thiazepine-3-spiro-2'-naphthalen-4-yl]acetic acid
55. 1-[6-(1-ethoxycarbonyl-3-phenylpropylamino)-5-oxo-3-phenylperhydro-1,4-thiazepin-4-yl]cyclopropanecarboxylic acid
56. α-{3-benzyl-6-[1-ethoxycarbonyl-2-(1-naphthyl)ethylamino]-5-oxoperhydro-1,4-thiazepin-4-yl}acetic acid
57. α-{3-benzyl-6-[1-carboxy-2-(1-naphthyl)ethylamino]-5-oxoperhydro-1,4-thiazepin-4-yl}acetic acid
58. α-{6-[1-ethoxycarbonyl-3-(2-naphthyl)propylamino]-5-oxo-3-phenylperhydro-1,4-thiazepin-4-yl}acetic acid
59. α-{6-[1-carboxy-3-(2-naphthyl)propylamino]-5-oxo-3-phenylperhydro-1,4-thiazepin-4-yl}acetic acid
60. α-{6-[1-ethoxycarbonyl-3-(2-thienyl)propylamino]-5-oxo-3-phenylperhydro-1,4-thiazepin-4-yl}acetic acid
61. α-{6-[1-carboxy-3-(2-thienyl)propylamino]-5-oxo-3-phenylperhydro-1,4-thiazepin-4-yl}acetic acid
62. α-{6-[1-ethoxycarbonyl-3-(2-imidazolyl)propylamino]-5-oxo-3-phenylperhydro-1,4-thiazepin-4-yl}acetic acid
63. α-{6-[1-carboxy-3-(2-imidazolyl)propylamino]-5-oxo-3-phenylperhydro-1,4-thiazepin-4-yl}acetic acid
64. α-{6-[1-ethoxycarbonyl-3-(1,3-thiazol-2-yl)propylamino]-5-oxo-3-phenylperhydro-1,4-thiazepin-4-yl}acetic acid
65. α-{6-[1-carboxy-3-(1,3-thiazol-2-yl)propylamino]-5-oxo-3-phenylperhydro-1,4-thiazepin-4-yl}acetic acid
66. α-[6-(1-ethoxycarbonyl-2-phenoxyethylamino)-5-oxo-3-phenylperhydro-1,4-thiazepin-4-yl]acetic acid
67. α-[6-(1-carboxy-2-phenoxyethylamino)-5-oxo-3-phenylperhydro-1,4-thiazepin-4-yl]acetic acid
68. α-[6-(1-ethoxycarbonyl-2-phenylthioethylamino)-5-oxo-3-phenylperhydro-1,4-thiazepin-4-yl]acetic acid
69. α-[6-(1-carboxy-2-phenylthioethylamino)-5-oxo-3-phenylperhydro-1,4-thiazepin-4-yl]acetic acid
70. pivaloyloxymethyl α-[6-(1-ethoxycarbonyl-3-phenylpropylamino)-5-oxo-3-phenylperhydro-1,4-thiazepin-4-yl]acetate
71. 1-(ethoxycarbonyloxy)ethyl α-[6-(1-ethoxycarbonyl-3-phenylpropylamino)-5-oxo-3-phenylperhydro-1,4-thiazepin-4-yl]acetate 72. (5-methyl-2-oxo-1,3-dioxolen-4-yl)methyl α-[6-(1-ethoxycarbonyl-3-phenylpropylamino)-5-oxo-3-phenylperhydro-1,4-thiazepin-4-yl]acetate
73. α-{5-oxo-3-phenyl-6-[3-phenyl-1-(pivaloyloxymethoxycarbonyl)propylamino]perhydro-1,4-thiazepin-4-yl}acetic acid
74. t-butyl α-[6-(1-ethoxycarbonyl-3-phenylpropylamino)-5-oxo-3-phenylperhydro-1,4-thiazepin-4-yl]acetate
75. t-butyl α-[6-(1-ethoxycarbonyl-3-phenylopropylamino)-5-oxo-2-phenylperhydro-1,4-thiazepin-4-yl]acetate
76. t-butyl 2-[6-(1-ethoxycarbonyl-3-phenylpropylamino)-5-oxo-3-phenylperhydro-1,4-thiazepin-4-yl]propionate
77. α-[6-(1-carboxy-3-phenylpropylamino)-5-oxo-2-(2-thienyl)perhydro-1,4-thiazepin-4-yl]acetic acid
78. α-[6-(1-ethoxycarbonyl-3-phenylpropylamino)-5-oxo-2-(2-thienyl)perhydro-1,4-thiazepin-4-yl]acetic acid
79. α-[6-(1-butoxycarbonyl-3-phenylpropylamino)-5-oxo-2-(2-thienyl)perhydro-1,4-thiazepin-4-yl]acetic acid
80. α-[6-(1-isobutoxycarbonyl-3-phenylpropylamino)-5-oxo-2-(2-thienyl)perhydro-1,4-thiazepin-4-yl]acetic acid
81. α-[6-(1-benzyloxycarbonyl-3-phenylpropylamino)-5-oxo-2-(2-thienyl)perhydro-1,4-thiazepin-4-yl]acetic acid
82. α-[6-(1-carboxy-3-phenylpropylamino)-5-oxo-2-(3-thienyl)perhydro-1,4-thiazepin-4-yl]acetic acid
83. α-[6-(1-ethoxycarbonyl-3-phenylpropylamino)-5-oxo-2-(3-thienyl)perhydro-1,4-thiazepin-4-yl]acetic acid
84. α-[6-(1-butoxycarbonyl-3-phenylpropylamino)-5-oxo-2-(3-thienyl)perhydro-1,4-thiazepin-4-yl]acetic acid
85. α-[6-(1-isobutoxycarbonyl-3-phenylpropylamino)-5-oxo-2-(3-thienyl)perhydro-1,4-thiazepin-4-yl]acetic acid
86. α-[6-(1-benzyloxycarbonyl-3-phenylpropylamino)-5-oxo-2-(3-thienyl)perhydro-1,4-thiazepin-4-yl]acetic acid
87. α-[6-(1-carboxy-3-phenylpropylamino)-2-(2-furyl)-5-oxoperhydro-1,4-thiazepin-4-yl]acetic acid
88. α-[6-(1-ethoxycarbonyl-3-phenylpropylamino)-2-(2-furyl)-5-oxoperhydro-1,4-thiazepin-4-yl]acetic acid
89. α-[6-(1-butoxycarbonyl-3-phenylpropylamino)-2-(2-furyl)-5-oxoperhydro-1,4-thiazepin-4-yl]acetic acid
90. α-[2-(2-furyl)-6-(1-isobutoxycarbonyl-3-phenylpropylamino)-5-oxoperhydro-1,4-thiazepin-4-yl]acetic acid
91. α-[6-(1-benzyloxycarbonyl-3-phenylpropylamino)-2-(2-furyl)-5-oxoperhydro-1,4-thiazepin-4-yl]acetic acid
92. α-[6-(1-carboxy-3-phenylpropylamino)-2-(3-furyl)-5-oxoperhydro-1,4-thiazepin-4-yl]acetic acid
93. α-[6-(1-ethoxycarbonyl-3-phenylpropylamino)-2-(3-furyl)-5-oxoperhydro-1,4-thiazepin-4-yl]acetic acid
94. α-[6-(1-butoxycarbonyl-3-phenylpropylamino)-2-(3-furyl)-5-oxoperhydro-1,4-thiazepin-4-yl]acetic acid
95. α-[6-(1-benzyloxycarbonyl-3-phenylpropylamino)-2-(3-furyl)-5-oxoperhydro-1,4-thiazepin-4-yl]acetic acid
96. α-[6-(1-carboxy-3-phenylpropylamino)-5-oxo-2-(1,3-thiazol-4-yl)perhydro-1,4-thiazepin-4-yl]acetic acid
97. α-[6-(1-ethoxycarbonyl-3-phenylpropylamino)-5-oxo-2-(1,3-thiazol-4-yl)perhydro-1,4-thiazepin-4-yl]acetic acid
98. α-[6-(1-butoxycarbonyl-3-phenylpropylamino)-5-oxo-2-(1,3-thiazol-4-yl)perhydro-1,4-thiazepin-4-yl]acetic acid
99. α-[6-(1-benzyloxycarbonyl-3-phenylpropylamino)-5-oxo-2-(1,3-thiazol-4-yl)perhydro-1,4-thiazepin-4-yl]acetic acid
100. α-[6-(1-carboxynonylamino)-5-oxo-2-(2-thienyl)perhydro-1,4-thiazepin-4-yl]acetic acid
101. α-[6-(1-ethoxycarbonylnonylamino)-5-oxo-2-(2-thienyl)perhydro-1,4-thiazepin-4-yl]acetic acid
102. α-[6-(1-carboxy-3-methylbutylamino)-5-oxo-2-(2-thienyl)perhydro-1,4-thiazepin-4-yl]acetic acid
103. α-[6-(1-ethoxycarbonyl-3-methylbutylamino)-5-oxo-2-(2-thienyl)perhydro-1,4-thiazepin-4-yl]acetic acid
104. α-[6-(1-carboxy-3-cyclohexylpropylamino)-5-oxo-2-(2-thienyl)perhydro-1,4-thiazepin-4-yl]acetic acid
105. α-[6-(3-cyclohexyl-1-ethoxycarbonylpropylamino)-5-oxo-2-(2-thienyl)perhydro-1,4-thiazepin-4-yl]acetic acid
106. α-[6-(1-carboxy-3-(2-indanyl)propylamino)-5-oxo-2-(2-thienyl)perhydro-1,4-thiazepin-4-yl]acetic acid
107. α-[6-(1-ethoxycarbonyl-3-(2-indanyl)-propylamino)-5-oxo-2-(2-thienyl)perhydro-1,4-thiazepin-4-yl]acetic acid
108. 2-[6-(1-ethoxycarbonyl-3-phenylpropylamino)-5-oxo-2-(2-thienyl)perhydro-1,4-thiazepin-4-yl]propionic acid
109. α-[6-(1-ethoxycarbonylnonylamino)-5-oxo-2-(3-thienyl)perhydro-1,4-thiazepin-4-yl]acetic acid
110. α-[6-(1-ethoxycarbonyl-3-methylbutylamino)-5-oxo-2-(3-thienyl)perhydro-1,4-thiazepin-4-yl]acetic acid
111. α-[6-(3-cyclohexyl-1-ethoxycarbonylpropylamino)-5-oxo-2-(3-thienyl)perhydro-1,4-thiazepin-4-yl]acetic acid
112. α-[6-(1-ethoxycarbonyl-3-(2-indanyl)-propylamino)-5-oxo-2-(3-thienyl)perhydro-1,4-thiazepin-4-yl]acetic acid
113. pivaloyloxymethyl α-[6-(1-ethoxycarbonyl-3-phenylpropylamino)-5-oxo-2-(2-thienyl)perhydro-1,4-thiazepin-4-yl]acetate
114. pivaloyloxymethyl α-[6-(1-ethoxycarbonyl-3-phenylpropylamino)-5-oxo-2-(3-thienyl)perhydro-1,4-thiazepin-4-yl]acetate
115. 1-(ethoxycarbonyloxy)ethyl α-[6-(1-ethoxycarbonyl-3-phenylpropylamino)-5-oxo-2-(2-thienyl)perhydro-1,4-thiazepin-4-yl]acetate
116. 1-(ethoxycarbonyloxy)ethyl α-[6-(1-ethoxycarbonyl-3-phenylpropylamino)-5-oxo-2-(3-thienyl)perhydro-1,4-thiazepin-4-yl]acetate
117. (5-methyl-2-oxo-1,3-dioxolen-4-yl)methyl α-[6-(1-ethoxycarbonyl)-3-phenylpropylamino)-5-oxo-2-(2-thienyl)perhydro-1,4-thiazepin-4-yl]acetate
118. (5-methyl-2-oxo-1,3-dioxolen-4-yl)methyl α-[6-(1-ethoxycarbonyl-3-phenylpropylamino)-5-oxo-2-(3-thienyl)perhydro-1,4-thiazepin-4-yl]acetate
119. t-butyl α-[6-(1-ethoxycarbonyl-3-phenylpropylamino)-5-oxo-2-(2-thienyl)perhydro-1,4-thiazepin-4-yl]acetate
120. t-butyl α-[6-(1-ethoxycarbonyl-3-phenylpropylamino)-5-oxo-2-(3-thienyl)perhydro-1,4-thiazepin-4-yl]acetate 121. α-[6-(1-ethoxycarbonyl-3-phenylpropylamino)-2-(2-methyl-1,3-thiazol-4-yl)-5-oxoperhydro-1,4-thiazepin-4-yl]acetic acid
122. α-[6-(1-ethoxycarbonyl-3-phenylpropylamino)-5-oxo-2-(2-phenyl-1,3-thiazol-4-yl)perhydro-1,4-thiazepin-4-yl]acetic acid
123. α-{5-oxo-6-[3-phenyl-1-(pivaloyloxymethoxycarbonyl)propylamino]-2-(2-thienyl)perhydro-1,4-thiazepin-4-yl}acetic acid
124. α-{5-oxo-6-[3-phenyl-1-(pivaloyloxymethoxycarbonyl)propylamino]-2-(3-thienyl)perhydro-1,4-thiazepin-4-yl}acetic acid
125. α-{6-[1-(1-ethoxycarbonyloxyethoxycarbonyl)-3-phenylpropylamino]-5-oxo-2-(2-thienyl)perhydro-1,4-thiazepin-4-yl}acetic acid
126. α-{6-[1-(1-ethoxycarbonyloxyethoxycarbonyl)-3-phenylpropylamino]-5-oxo-2-(3-thienyl)perhydro-1,4-thiazepin-4-yl}acetic acid
127. α-[6-(1-ethoxycarbonyl-3-phenylpropylamino)-2-(3-methyl-2-thienyl)-5-oxoperhydro-1,4-thiazepin-4-yl]acetic acid
128. α-[6-(1-ethoxycarbonyl-3-phenylpropylamino)-2-(5-methyl-2-thienyl)-5-oxoperhydro-1,4-thiazepin-4-yl]acetic acid
129. 3-[6-(1-ethoxycarbonyl-3-phenylpropylamino)-5-oxo-2-(2-thienyl)perhydro-1,4-thiazepin-4-yl]propionic acid
130. 3-[6-(1-ethoxycarbonyl-3-phenylpropylamino)-5-oxo-2-(3-thienyl)perhydro-1,4-thiazepin-4-yl]propionic acid
131. α-[6-(1-ethoxycarbonyl-2-phenylethylamino)-5-oxo-2-(2-thienyl)perhydro-1,4-thiazepin-4-yl]acetic acid
132. α-[6-(1-ethoxycarbonyl-2-phenylethylamino)-2-(2-furyl)-5-oxoperhydro-1,4-thiazepin-4-yl]acetic acid
133. α-[6-(1-carboxy-3-phenylpropylamino)-2-(1-naphthyl)-5-oxoperhydro-1,4-thiazepin-4-yl]acetic acid
134. α-[6-(1-ethoxycarbonyl-3-phenylpropylamino)-2-(1-naphthyl)-5-oxoperhydro-1,4-thiazepin-4-yl]acetic acid
135. α-[6-(1-butoxycarbonyl-3-phenylpropylamino)-2-(1-naphthyl)-5-oxoperhydro-1,4-thiazepin-4-yl]acetic acid
136. α-[6-(1-isobutoxycarbonyl-3-phenylpropylamino)-2-(1-naphthyl)-5-oxoperhydro-1,4-thiazepin-4-yl]acetic acid
137. α-[6-(1-benzyloxycarbonyl-3-phenylpropylamino)-2-(1-naphthyl)-5-oxoperhydro-1,4-thiazepin-4-yl]acetic acid
138. α-[6-(1-carboxy-3-phenylpropylamino)-2-(2-naphthyl)-5-oxoperhydro-1,4-thiazepin-4-yl]acetic acid
139. α-[6-(1-ethoxycarbonyl-3-phenylpropylamino)-2-(2-naphthyl)-5-oxoperhydro-1,4-thiazepin-4-yl]acetic acid
140. α-[6-(1-butoxycarbonyl-3-phenylpropylamino)-2-(2-naphthyl)-5-oxoperhydro-1,4-thiazepin-4-yl]acetic acid
141. α-[6-(1-isobutoxycarbonyl-3-phenylpropylamino)-2-(2-naphthyl)-5-oxoperhydro-1,4-thiazepin-4-yl]acetic acid
142. α-[6-(1-benzyloxycarbonyl-3-phenylpropylamino)-2-(2-naphthyl)-5-oxoperhydro-1,4-thiazepin-4-yl]acetic acid
143. α-[6-(1-carboxynonylamino)-2-(1-naphthyl)-5-oxoperhydro-1,4-thiazepin-4-yl]acetic acid
144. α-[6-(1-ethoxycarbonylnonylamino)-2-(1-naphthyl)-5-oxoperhydro-1,4-thiazepin-4-yl]acetic acid
145. α-[6-(1-carboxy-3-methylbutylamino)-2-(1-naphthyl)-5-oxoperhydro-1,4-thiazepin-4-yl]acetic acid
146. α-[6-(1-ethoxycarbonyl-3-methylbutylamino)-2-(1-naphthyl)-5-oxoperhydro-1,4-thiazepin-4-yl]acetic acid
147. α-[6-(1-carboxy-3-cyclohexylpropylamino)-2-(1-naphthyl)-5-oxoperhydro-1,4-thiazepin-4-yl]acetic acid
148. α-[6-(3-cyclohexyl-1-ethoxycarbonylpropylamino)-2-(1-naphthyl)-5-oxoperhydro-1,4-thiazepin-4-yl]acetic acid
149. α-{6-[1-carboxy-3-(2-indanyl)propylamino]-2-(1-naphthyl)-5-oxoperhydro-1,4-thiazepin-4-yl}acetic acid
150. α-{6-[1-ethoxycarbonyl-3-(2-indanyl)propylamino]-2-(1-naphthyl)-5-oxoperhydro-1,4-thiazepin-4-yl}acetic acid
151. 2-[6-(1-ethoxycarbonyl-3-phenylpropylamino)-2-(1-naphthyl)-5-oxoperhydro-1,4-thiazepin-4-yl]propionic acid
152. α-[6-(1-ethoxycarbonylnonylamino)-2-(2-naphthyl)-5-oxoperhydro-1,4-thiazepin-4-yl]acetic acid
153. α-[6-(1-ethoxycarbonyl-3-methylbutylamino)-2-(2-naphthyl)-5-oxoperhydro-1,4-thiazepin-4-yl]acetic acid
154. α-[6-(3-cyclohexyl-1-ethoxycarbonylpropylamino)-2-(2-naphthyl)-5-oxoperhydro-1,4-thiazepin-4-yl]acetic acid
155. α-[6-(1-ethoxycarbonyl-2-phenylethylamino)-2-(2-naphthyl)-5-oxoperhydro-1,4-thiazepin-4-yl]acetic acid
156. α-{6-[1-ethoxycarbonyl-3-(2-indanyl)propylamino]-2-(2-naphthyl)-5-oxoperhydro-1,4-thiazepin-4-yl}acetic acid
157. pivaloyloxymethyl α-[6-(1-ethoxycarbonyl-3-phenylpropylamino)-2-(1-naphthyl)-5-oxoperhydro-1,4-thiazepin-4-yl]acetate
158. pivaloyloxymethyl α-[6-(1-ethoxycarbonyl-3-phenylpropylamino)-2-(2-naphthyl)-5-oxoperhydro-1,4-thiazepin-4-yl]acetate
159. 1-(ethoxycarbonyloxy)ethyl α-[6-(1-ethoxycarbonyl-3-phenylpropylamino)-2-(1-naphthyl)-5-oxoperhydro-1,4-thiazepin-4-yl]acetate
160. 1-(ethoxycarbonyloxy)ethyl α-[6-(1-ethoxycarbonyl-3-phenylpropylamino)-2-(2-naphthyl)-5-oxoperhydro-1,4-thiazepin-4-yl]acetate
161. (5-methyl-2-oxo-1,3-dioxolen-4-yl)methyl α-[6-(1-ethoxycarbonyl-3-phenylpropylamino)-2-(1-naphthyl)-5-oxoperhydro-1,4-thiazepin-4-yl]acetate
162. (5-methyl-2-oxo-1,3-dioxolen-4-yl)methyl α-[6-(1-ethoxycarbonyl-3-phenylpropylamino)-2-(2-naphthyl)-5-oxoperhydro-1,4-thiazepin-4-yl]acetate
163. t-butyl α-[6-(1-ethoxycarbonyl-3-phenylpropylamino)-2-(1-naphthyl)-5-oxoperhydro-1,4-thiazepin-4-yl]acetate
164. t-butyl α-[6-(1-ethoxycarbonyl-3-phenylpropylamino)-2-(2-naphthyl)-5-oxoperhydro-1,4-thiazepin-4-yl]acetate
165. α-{2-(1-naphthyl)-5-oxo-6-[3-phenyl-1-(pivaloyloxymethoxycarbonyl)propylamino]perhydro-1,4-thiazepin-4-yl}acetic acid
166. α-{2-(2-naphthyl)-5-oxo-6-[3-phenyl-1-(pivaloyloxymethoxycarbonyl)propylamino]perhydro-1,4-thiazepin-4-yl}acetic acid
167. α-{6-[1-(1-ethoxycarbonyloxyethoxycarbonyl)-3-phenylpropylamino]-2-(1-naphthyl)-5-oxoperhydro-1,4-thiazepin-4-yl}acetic acid 168. α-{6-[1-(1-ethoxycarbonyloxyethoxycarbonyl)-3-phenylpropylamino]-2-(2-naphthyl)-5-oxoperhydro-1,4-thiazepin-4-yl}acetic acid
169. 3-[6-(1-ethoxycarbonyl-3-phenylpropylamino)-2-(1-naphthyl)-5-oxoperhydro-1,4-thiazepin-4-yl]propionic acid
170. 3-[6-(1-ethoxycarbonyl-3-phenylpropylamino)-2-(2-naphthyl)-5-oxoperhydro-1,4-thiazepin-4-yl]propionic acid
171. α-[6-(1-ethoxycarbonyl-3-phenylpropylamino)-3-methyl-5-oxoperhydro-1,4-thiazepin-4-yl]acetic acid
172. α-[6-(1-carboxy-3-phenylpropylamino)-3-methyl-5-oxoperhydro-1,4-thiazepin-4-yl]acetic acid
173. α-[6-(1-ethoxycarbonyl-3-phenylpropylamino)-3-isopropyl-5-oxoperhydro-1,4-thiazepin-4-yl]acetic acid
174. α-[6-(1-carboxy-3-phenylpropylamino)-3-isopropyl-5-oxoperhydro-1,4-thiazepin-4-yl]acetic acid
175. α-[3-sec-butyl-6-(1-ethoxycarbonyl-3-phenylpropylamino)-5-oxoperhydro-1,4-thiazepin-4-yl]acetic acid
176. α-[3-sec-butyl-6-(1-carboxy-3-phenylpropylamino)-5-oxoperhydro-1,4-thiazepin-4-yl]acetic acid
177. α-[6-(1-ethoxycarbonyl-3-phenylpropylamino)-2-methyl-5-oxoperhydro-1,4-thiazepin-4-yl]acetic acid
178. α-[6-(1-butoxycarbonyl-3-phenylpropylamino)-2-methyl-5-oxoperhydro-1,4-thiazepin-4-yl]acetic acid
179. α-[6-(1-carboxy-3-phenylpropylamino)-2-methyl-5-oxoperhydro-1,4-thiazepin-4-yl]acetic acid
180. α-[6-(1-ethoxycarbonyl-3-phenylpropylamino)-2-isopropyl-5-oxoperhydro-1,4-thiazepin-4-yl]acetic acid
181. α-[6-(1-butoxycarbonyl-3-phenylpropylamino)-2-isopropyl-5-oxoperhydro-1,4-thiazepin-4-yl]acetic acid
182. α-[6-(1-carboxy-3-phenylpropylamino)-2-isopropyl-5-oxoperhydro-1,4-thiazepin-4-yl]acetic acid
183. α-[6-(1-ethoxycarbonyl-3-phenylpropylamino)-2-isobutyl-5-oxoperhydro-1,4-thiazepin-4-yl]acetic acid
184. α-[6-(1-butoxycarbonyl-3-phenylpropylamino)-2-isobutyl-5-oxoperhydro-1,4-thiazepin-4-yl]acetic acid
185. α-[6-(1-carboxy-3-phenylpropylamino)-2-isobutyl-5-oxoperhydro-1,4-thiazepin-4-yl]acetic acid
186. α-[6-(1-butoxycarbonyl-3-phenylpropylamino)-5-oxo-3-phenylperhydro-1,4-thiazepin-4-yl]acetic acid
187. α-[6-(1-benzyloxycarbonyl-3-phenylpropylamino)-5-oxo-2-phenylperhydro-1,4-thiazepin-4-yl]acetic acid
188. α-[6-(1-butoxycarbonyl-3-phenylpropylamino)-5-oxo-2-phenylperhydro-1,4-thiazepin-4-yl]acetic acid
189. α-[6-(1-benzyloxycarbonyl-3-phenylpropylamino)-5-oxo-2-phenylperhydro-1,4-thiazepin-4-yl]acetic acid
190. α-[6-(1-butoxycarbonyl-3-phenylpropylamino)-5-oxo-3-(2-thienyl)perhydro-1,4-thiazepin-4-yl]acetic acid
191. α-[6-(1-benzyloxycarbonyl-3-phenylpropylamino)-5-oxo-3-(2-thienyl)perhydro-1,4-thiazepin-4-yl]acetic acid
192. α-[6-(1-butoxycarbonyl-3-phenylpropylamino)-3-methyl-5-oxoperhydro-1,4-thiazepin-4-yl]acetic acid
193. α-[6-(1-butoxycarbonyl-3-phenylpropylamino)-3-isopropyl-5-oxoperhydro-1,4-thiazepin-4-yl]acetic acid
194. α-[6-(1-butoxycarbonyl-3-phenylpropylamino)-3-sec-butyl-5-oxoperhydro-1,4-thiazepin-4-yl]acetic acid
195. α-[6-(1-butoxycaronyl-3-phenylpropylamino)-3-isobutyl-5-oxoperhydro-1,4-thiazepin-4-yl]acetic acid
196. t-butyl α-[6-(1-butoxycarbonyl-3-phenylpropylamino)-5-oxo-2-(2-thienyl)perhydro-1,4-thiazepin-4-yl]acetate
197. t-butyl α-[6-(1-butoxycarbonyl-3-phenylpropylamino)-5-oxo-2-(3-thienyl)perhydro-1,4-thiazepin-4-yl]acetate
198. t-butyl α-[6-(1-butoxycarbonyl-3-phenylpropylamino)-2-(2-furyl)-5-oxoperhydro-1,4-thiazepin-4-yl]acetate
199. t-butyl α-[6-(1-butoxycarbonyl-3-phenylpropylamino)-2-(3-furyl)-5-oxoperhydro-1,4-thiazepin-4-yl]acetate
200. t-butyl α-[6-(1-butoxycarbonyl-3-phenylpropylamino)-5-oxo-2-(1,3-thiazol-4-yl)perhydro-1,4-thiazepin-4-yl]acetate.
201. t-butyl α-[6-(1-ethoxycarbonyl-3-phenylpropylamino)-5-oxo-3-(2-thienyl)perhydro-1,4-thiazepin-4-yl]acetate.
202. t-butyl α-[6-(1-butoxycarbonyl-3-phenylpropylamino)-5-oxo-2-phenylperhydro-1,4-thiazepin-4-yl]acetate.
203. t-butyl α-[6-(1-benzyloxycarbonyl-3-phenylpropylamino)-5-oxo-2-phenylperhydro-1,4-thiazepin-4-yl]acetate.
204. t-butyl α-[6-(1-butoxycarbonyl-3-phenylpropylamino)-5-oxo-3-(2-thienyl)perhydro-1,4-thiazepin-4-yl]acetate.
205. t-butyl α-[6-(1-benzyloxycarbonyl-3-phenylpropylamino)-5-oxo-3-(2-thienyl)perhydro-1,4-thiazepin-4-yl]acetate.
206. t-butyl α-[6-(1-ethoxycarbonyl-3-phenylpropylamino)-3-isopropyl-5-oxoperhydro-1,4-thiazepin-4-yl]acetate.
207. t-butyl α-[6-(1-ethoxycarbonyl-3-phenylpropylamino)-3-methyl-5-oxoperhydro-1,4-thiazepin-4-yl]acetate.
208. t-butyl α-[3-benzyl-6-(1-ethoxycarbonyl-3-phenylpropylamino)-5-oxoperhydro-1,4-thiazepin-4-yl]acetate.
209. t-butyl α-[6-(1-benzyloxycarbonyl-3-phenylpropylamino)-5-oxo-2-(3-thienyl)perhydro-1,4-thiazepin-4-yl]acetate
210. t-butyl α-[6-(1-benzyloxycarbonyl-3-phenylpropylamino)-5-oxo-2-(2-thienyl)perhydro-1,4-thiazepin-4-yl]acetate
211. t-butyl α-[6-(1-ethoxycarbonyl-3-phenylpropylamino)-2-(2-furyl)-5-oxoperhydro-1,4-thiazepin-4-yl]acetate
212. t-butyl α-[6-(1-benzyloxycarbonyl-3-phenylpropylamino)-2-(2-furyl)-5-oxoperhydro-1,4-thiazepin-4-yl]acetate Of the compounds listed above, preferred compounds from the point of view of their biological activity, are Compounds Nos. 11, 12, 27, 28, 29, 30, 39, 40, 77, 78, 79, 80, 81, 82, 83, 84, 85, 86, 87, 88, 89, 92, 93, 94, 96, 97, 98, 100, 101, 109, 127, 128, 133, 134, 138, 139, 173, 174, 177, 178, 179, 180, 181, 182, 183, 184, 185, 186, 188, 190, 193, 194 and 195, Compounds Nos. 77, 78, 79, 82, 83, 84, 87, 88, 89, 92, 93, 94, 96, 97, 98, 100, 101, 109, 127 and 128 being more preferred and Compounds Nos. 77, 78, 79, 82, 83, 84, 87, 88, 89, 92, 93 and 94 being most preferred. Compounds Nos. 74, 75, 76, 119, 120, 163, 164, 196, 197, 198, 199, 200, and 201–212 inclusive are of particular value in the synthesis of other, biologically more active, compounds.

The compounds of the present invention can contain many asymmetric carbon atoms and can thus exist in the form of many stereoisomers and the present invention envisages both the individual isolated isomers as well as mixtures thereof. The following carbon atoms are asymmetric in all of the compounds of the invention: the carbon atom to which the group represented by $R^1$—A— is attached; the carbon atom at the 6-position of the thiazepine ring; and either or both of the carbon atoms at the 2 and 3 positions of the thiazepine ring. In addition, depending upon the nature of the substituent groups on the compounds of the invention, other carbon atoms may also be asymmetric. The compounds of the invention may be prepared as mixtures of isomers and then separated by conventional techniques or they may be prepared by stereo-specific synthesis techniques, all of which are well-known to those skilled in the art.

The compounds of the present invention can be prepared by the condensation of a compound of formula (II):

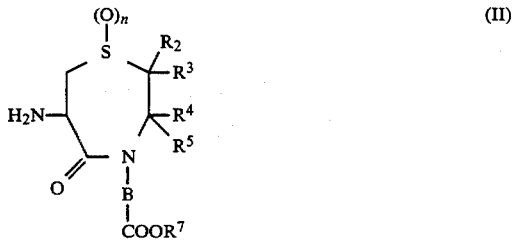

(in which $R^2$, $R^3$, $R^4$, $R^5$, $R^7$, B and n are as defined above) with a compound of formula (III):

(in which $R^1$, $R^6$ and A are as defined above and X represents a halogen atom or a sulfonyloxy group) or by reductive condensation of the aforementioned compound of formula (II) with a compound of formula (IV):

(in which $R^1$, $R^6$ and A are as defined above).

In the compound of formula (III), where X represents a halogen atom, this is preferably a chlorine, bromine or iodine atom; where X represents a sulfonyloxy group, this is preferably a substituted or unsubstituted $C_1$-$C_6$ alkanesulfonyloxy group, such as a methanesulfonyloxy, ethanesulfonyloxy or trifluoromethanesulfonyloxy group, or a substituted or unsubstituted aromatic sulfonyloxy group, such as a benzenesulfonyloxy or p-toluenesulfonyloxy group; in the case of the substituted groups, substituents are selected from the group consisting of substituents (a) defined above.

Condensation of the compound of formula (II) with the compound of formula (III) is preferably effected in the presence of a solvent and of a base. The nature of the solvent is not critical, provided that it has no adverse effect upon the reaction; suitable solvents include: aliphatic and aromatic hydrocarbons, such as hexane or benzene; halogenated aliphatic or aromatic, preferably aliphatic, hydrocarbons, such as methylene chloride or 1,2-dichloroethane; ethers, such as tetrahydrofuran or dioxane; esters, such as ethyl acetate; ketones, such as acetone; amides, such as dimethylformamide, dimethylacetamide or hexamethylphosphoric triamide; and sulfoxides, such as dimethyl sulfoxide. There is likewise no criticality as to the nature of the base to be employed, provided that it does not adversely affect the reaction. Suitable bases include, for example: alkali metal and alkaline earth metal carbonates, such as sodium carbonate, potassium carbonate or calcium carbonate; alkali metal bicarbonates, such as sodium bicarbonate or potassium bicarbonate; alkali metal hydrides, such as sodium hydride or lithium hydride; or organic bases, such as triethylamine, pyridine, picoline or tetraethylammonium hydroxide. If desired, the reaction may be carried out as a two-phase reaction employing water as the solvent for one phase and a water-immiscible solvent (such as methylene chloride or chloroform) for the other phase; in this case, a phase-transfer catalyst (such as tetrabutylammonium bromide or benzyltriethylammonium iodide) should be employed and the base may be a relatively strong base, such as an alkali metal hydroxide (for example sodium hydroxide or potassium hydroxide).

The reaction will take place over a wide range of temperatures and the precise temperature chosen is not critical to the present invention; we generally find it convenient to carry out the reaction at a temperature within the range from 0° to 120° C. The time required for the reaction will vary depending upon many factors, but primarily upon the natures of the solvent, base and reagents, and upon the reaction temperature, but a period of from 1 hour to 3 days will normally suffice.

After completion of the reaction, the desired compound may be obtained from the reaction mixture by conventional means. For example, one suitable recovery technique comprises: adding an organic solvent, such as ethyl acetate, to the reaction mixture; separating the organic layer and washing it with water; drying the organic layer; and distilling off the solvent to give the desired product. If necessary, this product can be further purified by various conventional techniques, such as recrystallization and/or the chromatography techniques, particularly column chromatography.

Reaction of the compound of formula (II) with the compound of formula (IV) takes place under reductive condensation conditions. The reductive conditions may be provided by a variety of means, for example: catalytic reduction using a metal, such as platinum, palladium, Raney nickel or rhodium, optionally on a carrier, in the presence of hydrogen; reduction with a metal hydride, such as lithium aluminum hydride, lithium borohydride, lithium cyanoborohydride, sodium cyanoborohydride, sodium borohydride or potassium borohydride; reduction with an active metal, such as sodium or magnesium, together with an alcohol, such as methanol or ethanol; or reduction with a metal, such as iron or zinc, and an acid, such as hydrochloric acid or acetic acid. The reaction is preferably effected in the presence of a solvent, the nature of which is not critical, provided that it has no adverse effect upon (although it may participate in) the reaction. Suitable solvents include water and a variety of organic solvents, for example: alcohols, such as methanol or ethanol; ethers, such as tetrahydrofuran, diethyl ether or dioxane; halogenated hydrocarbons, such as methylene chloride or chloroform; esters, such as ethyl acetate; aromatic hydrocarbons, such as benzene or toluene; amides, such as dimethylformamide or dimethylacetamide; and organic acids, such as acetic acid. It will be noted that certain of the compounds mentioned herein as potential solvents may also serve as part of the reduction system described above and, in that case, the same compound may serve both as a reagent and as a solvent, if desired.

The reaction will take place over a wide range of temperatures, for example from $-20°$ C. to $+100°$ C., although the precise temperature chosen will depend upon several factors, of which the most important is the nature of the reductive system employed. The reaction can be carried out under atmospheric pressure, although, in some cases, it may be desirable to carry it out under an elevated or reduced pressure.

Of the compounds of formula (I), the monoester monocarboxylic acids in which $R^6$ represents an ester residue and $R^7$ represents a hydrogen atom and the dicarboxylic acids in which both $R^6$ and $R^7$ represent hydrogen atoms, as well as the salts of these acids, are medically the most important compounds. The monoester monocarboxylic acid can be prepared by selective deprotection of the ester residue represented by $R^7$ in a diester compound in which both $R^6$ and $R^7$ represent ester residues; alternatively, it may be prepared by the reductive condensation of an amino acid of formula (II) in which $R^7$ represents a hydrogen atom with a ketoester of formula (IV) in which $R^6$ represents an ester residue.

A dicarboxylic acid of formula (I) in which both $R^6$ and $R^7$ represent hydrogen atoms can also be prepared by hydrolyzing a diester or monoester of formula (I) (in which $R^6$ and $R^7$ represent ester residues or $R^6$ represents an ester residue and $R^7$ represents a hydrogen atom) with an acid or base; it may also be prepared by reductive removal of the ester group or groups of the diester or monoester. The reaction conditions employed are the same as those described for deprotection of the carboxy-protecting group represented by $R^{12}$ in the compound of formula (VII) described hereafter.

If desired, compounds of formula (I) in which n is 0 may be converted to the corresponding compounds in which n is 1 or 2 by oxidation, as described in more detail hereafter.

The starting materials of formula (II) employed in the processes of the present invention may be prepared in a variety of ways. For example, these compounds of formula (II) in which n is 0, that is to say compounds of formula (IIa):

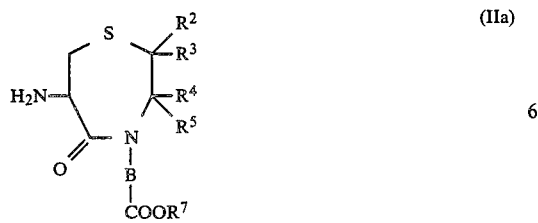

(in which $R^2$–$R^5$, B and $R^7$ are as defined above) can be prepared, for example, by the process illustrated in the following reaction scheme:

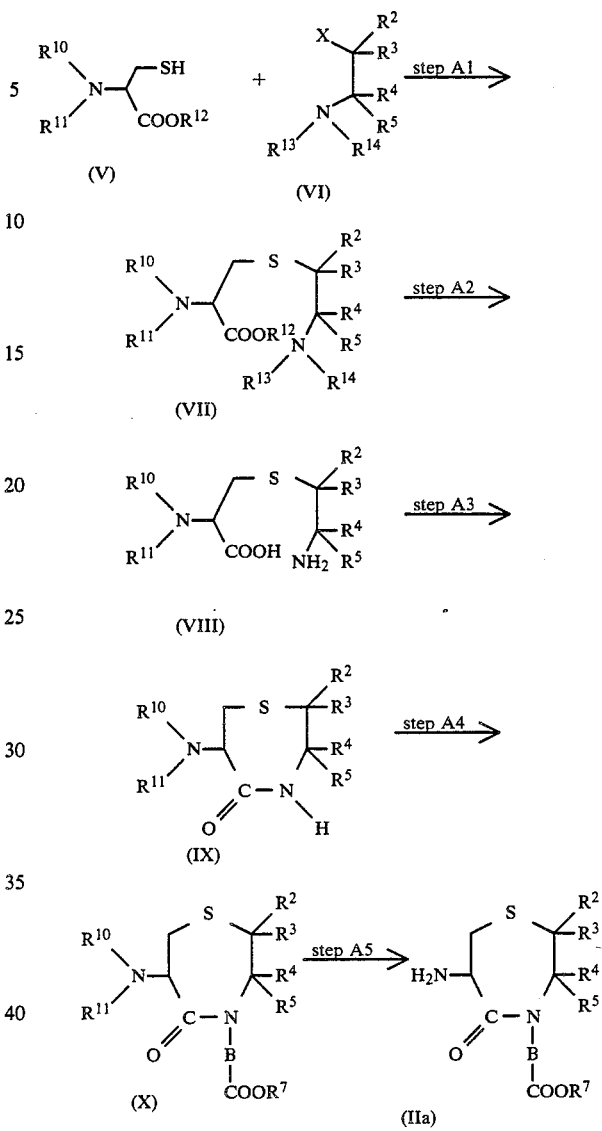

In the above formulae, $R^2$–$R^5$, $R^7$ and B are as defined above. $R^{10}$, $R^{11}$, $R^{13}$ and $R^{14}$ are the same or different and each represents a hydrogen atom or an amino-protecting group ($R^{10}$ and $R^{11}$ being different from $R^{13}$ and $R^{14}$) and $R^{12}$ represents a hydrogen atom or carboxy-protecting group.

The nature of the carboxy-protecting group represented by $R^{12}$ is not critical to the present invention, as its purpose is merely to protect the carboxy group from participation in the reaction of step A1 and it is then immediately eliminated in step A2. Accordingly, any protecting group known in the art for use in this type of reaction may be employed, normally an ester residue. Examples include: methyl and substituted methyl groups, such as the methyl, allyl, methoxymethyl, methylthiomethyl, 2-methoxyethoxymethyl, benzyloxymethyl, phenacyl, p-bromophenacyl or phthalimidomethyl groups; other lower (e.g. $C_2$–$C_6$, preferably $C_2$–$C_4$) alkyl groups, which may be substituted or unsubstituted, for example the ethyl, 2,2,2-trichloroethyl, 2-iodoethyl, 2-trimethylsilylethyl, 2-(p-toluenesulfonyl)ethyl or t-butyl groups; benzyl groups which may be substituted or unsubstituted, for example the benzyl, benzhydryl (i.e. diphenylmethyl), p-methoxybenzyl or p-nitrobenzyl groups; or silyl groups, preferably trialkylsilyl groups in which each alkyl part has from 1 to 6, preferably from 1 to 4, carbon atoms, for example the trimethylsilyl or t-butyldimethylsilyl groups. It should, however, be appreciated that these groups are given merely by way of exemplification and there is no limitation on the nature of the carboxy-protecting group, provided that it is capable of serving a protecting function.

Likewise, there is no criticality as to the nature of the amino-protecting group represented by $R^{10}$, $R^{11}$, $R^{13}$ or $R^{14}$, as these groups are present in certain of the steps of the reaction scheme merely in order to prevent participation of the amino group which they protect in the relevant reaction and they are removed either in step A2 or in step A5 and thus do not appear in the final product, the starting material of formula (IIa), of this reaction scheme. Accordingly, they have no influence on the nature of the final product and may be chosen having regard solely to their protecting function. Examples of such protecting groups include: alkoxycarbonyl groups, in which the alkoxy part preferably has from 1 to 6, more preferably from 1 to 4, carbon atoms and which may be substituted or unsubstituted [examples of substituents being any of those groups and atoms listed above as substituents (a) and (b) as well as lower (e.g. $C_1$–$C_4$) alkylidene groups], for example the 2,2,2-trichloroethoxycarbonyl, 2-iodoethoxycarbonyl, trimethylsilylethoxycarbonyl, t-butoxycarbonyl, allyloxycarbonyl, benzyloxycarbonyl, p-methoxybenzyloxycarbonyl or p-nitrobenzyloxycarbonyl groups; alkanesulfonylalkoxycarbonyl groups in which each alkyl part has from 1 to 6, preferably from 1 to 4, carbon atoms or aromatic sulfonylalkoxycarbonyl groups in which the aryl part is $C_6$–$C_{10}$ carbocyclic aryl and the alkyl part is $C_1$–$C_6$, preferably $C_1$–$C_4$, alkyl and where the aryl part may be unsubstituted or have one or more of the substituents heretofore listed as substituent (a), for example the 2-methanesulfonylethoxycarbonyl or 2-(p-toluenesulfonyl)ethoxycarbonyl group; $C_1$–$C_7$ aliphatic acyl or ($C_6$–$C_{10}$ carbocyclic aryl) acyl groups, which may be unsubstituted or have one or more of the substituents listed in group (a) above, for example the formyl, acetyl, benzoyl, chloroacetyl or trifluoroacetyl groups; cyclic diacyl groups, such as the phthaloyl or 2,3-diphenylmalonyl groups; substituted methyl groups, such as the methoxymethyl, benzyloxymethyl, benzyl, 3,4-dimethoxybenzyl or trityl groups; alkylidene or aralkylidene groups, such as the propylidene, benzylidene or salicylidene groups; acylvinyl groups, such as the 2-acetyl-1-methylvinyl or 2-benzoyl-1-methylvinyl groups; and silyl groups, particularly trialkylsilyl groups in which each alkyl part has from 1 to 6, preferably from 1 to 4, carbon atoms, for example the trimethylsilyl or t-butyldimethylsilyl groups. It should, however, be appreciated that these groups are given by way of example only and that the nature of the group is not critical, provided that it serves its required protecting function.

The compound of formula (V) is a derivative of cysteine and its reaction in step A1 with the compound of formula (VI) is preferably effected in a suitable solvent and in the presence of a base. The nature of the solvent is not critical, provided that it has no adverse effect upon the reaction, and similarly the nature of the base is not critical. The reagents and reaction conditions, such as the solvent, base, reaction temperature, and reaction time, as well as the techniques for isolation and purification of the reaction product are similar to those described in detail in relation to the reaction of the compound of formula (II) with the compound of formula (III).

In step A2, the carboxy-protecting group represented by $R^{12}$ and the amino-protecting groups represented by $R^{13}$ and $R^{14}$ are removed by conventional means well-known in chemical synthesis and, apart from one consideration, the reaction employed to remove these groups is not critical to the present process. It is, however, necessary that the removal reaction should have no effect on the amino-protecting groups represented by $R^{10}$ and $R^{11}$ in the cysteine part of the molecule of the compound of formula (VII). The precise removal reaction or reactions chosen will, of course, depend upon the precise nature of the carboxy-protecting group represented by $R^{12}$ and the amino-protecting groups represented by $R^{13}$ and $R^{14}$, for example:

where $R^{12}$ represents an alkyl group, such as a methyl or ethyl group, the compound may be deprotected by hydrolysis with an alkali, preferably an alkali metal hydroxide, such as lithium hydroxide, sodium hydroxide or potassium hydroxide;

where $R^{12}$ represents a protecting group such as a methoxymethyl, methoxyethoxymethyl, t-butyl, benzhydryl, p-methoxybenzyl, trimethylsilyl or t-butyldimethylsilyl group, the compound may be deprotected by reaction with an acid or a Lewis acid, such as hydrochloric acid, trifluoroacetic acid or aluminum chloride;

where $R^{13}$ and/or $R^{14}$ represents a protecting group such as a t-butoxycarbonyl, p-methoxybenzyloxycarbonyl, trityl or t-butyldimethylsilylethoxycarbonyl group, this is similarly removed by reaction with an acid or a Lewis acid;

where $R^{12}$ represents a group such as a benzyl or p-nitrobenzyl group and/or $R^{13}$ or $R^{14}$ represents a group such as a benzyloxycarbonyl or p-nitrobenzyloxycarbonyl group, the compound may be deprotected by catalytic reduction, employing hydrogen in the presence of a suitable catalyst, for example palladium, which may be supported, for example, on carbon;

where $R^{12}$ represents a group such as a 2,2,2-trichloroethyl, 2-iodoethyl, phenacyl or p-bromophenacyl group and/or $R^{13}$ or $R^{14}$ represents a group such as a 2,2,2-trichloroethoxycarbonyl or 2-iodoethoxycarbonyl group, the compound may be deprotected by reduction employing a mixture of a metal powder (e.g. zinc powder) and an acid (e.g. acetic acid or hydrochloric acid);

where $R^{12}$ represents a group such as an allyl group and/or $R^{13}$ or $R^{14}$ represents a group such as an allyloxycarbonyl group, the compound may be deprotected by a catalytic reaction, employing, for example, tetrakis(triphenylphosphine)palladium (O); or where $R^{13}$ or $R^{14}$ is a group such as a phthaloyl group, the compound may be deprotected by reaction with hydrazine or a hydrazine derivative, preferably an alkylhydrazine, such as hydrazine or methylhydrazine.

The reaction in this deprotection step A2 is preferably effected in the presence of a solvent, the nature of which is not critical, provided that it has no adverse effect upon the reaction. The optimum solvent will, of course, depend upon the precise reaction chosen and, as is obvious to those skilled in the art, in some cases, the solvent may participate in the deprotection reaction. In general terms, suitable solvents may be chosen from the class consisting of: water; acids, preferably carboxylic and more preferably aliphatic carboxylic, acids such as acetic acid or formic acid; alcohols, such as methanol or ethanol; ethers, such as tetrahydrofuran, dioxane or anisole; ketones, such as acetone; halogenated hydrocarbons, preferably halogenated aliphatic hydrocarbons, such as methylene chloride or chloroform; and hydrocarbons, which may be aliphatic or aromatic, such as benzene or toluene. These reactions will take place over a wide range of temperatures, for example at a temperature within the range from $-10°$ C. to $+100°$ C.; in general, the time allowed for the reaction will vary depending upon the nature of the deprotection reaction and other reaction conditions, including the reaction temperature; at one extreme, a relatively fast reaction will be complete within perhaps 30 minutes, whereas, at the other extreme, it may be advisable to allow a whole day and night for the reaction: however, these are matters well within the skill and knowledge of the laboratory technician.

It will, of course, be appreciated that removal of the amino-protecting groups and carboxy-protecting groups may be carried out in any order or (assuming a suitable removal reaction is chosen in relation to the particular protecting groups) simultaneously; likewise, although it is not preferred, if the amino-protecting groups $R^{13}$ and $R^{14}$ are different, these may be removed sequentially or simultaneously. In general, however, either the carboxy-protecting group represented by $R^{12}$ is first removed, and then the amino-protecting groups $R^{13}$ and/or $R^{14}$ are removed or the amino-protecting groups represented by $R^{13}$ and/or $R^{14}$ are first removed, and then the carboxy-protecting group $R^{12}$ is removed, or all protecting groups, $R^{12}$ and $R^{13}$ and/or $R^{14}$, are removed together. For example, if $R^{12}$ represents a t-butyl group, $R^{13}$ represents a t-butoxycarbonyl group and $R^{14}$ represents a hydrogen atom, the compound of formula (VIII) may be obtained in a single step by deprotection with an acid. Similarly, if $R^{12}$ represents a 2,2,2-trichloroethyl group, $R^{13}$ represents a 2,2,2-trichloroethoxycarbonyl group and $R^{14}$ represents a hydrogen atom, the compound of formula (VIII) may be obtained by deprotection in a single step with a combination of zinc powder and an acid.

If desired, the compound of formula (VIII) may be purified by various conventional means, for example by isoelectric precipitation, recrystallization or the various chromatography techniques, such as column chromatography; however, if desired, the crude product obtained from this reaction may be employed directly in the next step without any specific purification.

In step A3, the compound of formula (VIII) is cyclized to form a perhydrothiazepine derivative of formula (IX) by condensing the free amino group with the free carboxy group, to form an amide linkage, of a type which is well-known in the field of peptide chemistry. This reaction may generally be carried out by contacting the compound of formula (VIII) with a dehydrating agent, such as N,N'-dicyclohexylcarbodiimide, carbonyldiimidazole, diphenylphosphoryl azide, diethyl cyanophosphate or phosphorus pentachloride. If a dehydrating agent of the carbodiimide kind is employed, the reaction can be accelerated by carrying out the reaction in the presence of 1-hydroxybenzotriazole, N-hydroxysuccinimide or a similar compound. It may also be advantageous to carry out the reaction in the presence of a base, which may be an organic base, for example pyridine, picoline, triethylamine or N-methylmorpholine, or an inorganic base, such as sodium carbonate or sodium bicarbonate. The reaction is preferably effected in the presence of a solvent, the nature of which is not critical, provided that it has no adverse effect upon the reaction. Suitable solvents include, for example: amides, such as dimethylformamide, hexamethylphosphoric triamide, or dimethylacetamide; ethers, such as tetrahydrofuran or dioxane; halogenated hydrocarbons, preferably aliphatic hydrocarbons, such as methylene chloride or chloroform; esters, such as ethyl acetate; or aromatic hydrocarbons, such as benzene or toluene. Sometimes, the product can be isolated as crystals from the reaction mixture; at other times, other recovery technique (such as those described elsewhere in the specification) may be employed; if desired, the product can be purified by various conventional technique, such as the chromatography techniques, especially column chromatography.

In step A4 of the reaction scheme, the compound of formula (X) can be prepared by N-alkylation of the compound of formula (IX), employing a compound of formula (XI):

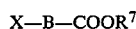

$$X-B-COOR^7 \qquad (XI)$$

[in which B and $R^7$ are as defined above and X represents preferably a bromine atom; other examples are given in relation to the atom or group represented by X in the compound of formula (III)]. This reaction is preferably effected in the presence of a solvent and of a base. The nature of the solvent employed is not critical, provided that it has no adverse effect upon the reaction. Suitable solvents include, for example: hydrocarbons, which may be aliphatic or aromatic, for example hexane or benzene; halogenated hydrocarbons, which likewise may be aliphatic or aromatic, but which are preferably aliphatic, such as methylene chloride or 1,2-dichloroethane; ethers, such as tetrahydrofuran or dioxane; esters, such as ethyl acetate; ketones, such as acetone; amides, such as dimethylformamide, dimethylacetamide or hexamethylphosphoric triamide; or sulfoxides, such as dimethyl sulfoxide. The nature of the base is likewise not critical, and examples include: alkali metal hydrides, such as sodium hydride, lithium hydride or potassium hydride; alkyl-alkali metal compounds, such as butyllithium; alkali metal amides, such as lithium diisopropylamide, lithium dicyclohexylamide or lithium bis(trimethylsilyl)amide; alkali metal carbonates, such as sodium carbonate or potassium carbonate; or organic amines, such as triethylamine, triethylenediamine, 1,5-diazabicyclo[4.3.0]non-5-ene or 1,8-diazabicyclo-[5.4.0]undec-7-ene. If desired, this reaction may be carried out as a two-phase reaction employed water and a water-immiscible solvent as the reaction media; suitable water-immiscible solvents include methylene chloride and chloroform. In the case of the two-phase reaction, a phase transfer catalyst, such as tetrabutylammonium bromide or benzyltriethylammonium iodide, may be employed and the base may be a relatively strong base, such as an alkali metal hydroxide, e.g. sodium hydroxide or potassium hydroxide. The reaction will take place over a wide range of temperatures, for example from $-20°$ C. to $+100°$ C. The time required for the reaction will vary widely, depending on many factors, including the reaction temperature as well as the natures of the solvent, base and reagents, but a period of from 30 minutes to 24 hours will normally suffice. After completion of the reaction, the desired compound of formula (X) may be obtained from the reaction mixture by conventional means. For example, one suitable recovery technique comprises: adding an organic solvent, such as ethyl acetate, to the reaction mixture; washing the organic layer with water and then drying it; and finally distilling off the solvent to give the desired compound. If necessary, this compound may be further purified by such conventional means as recrystallization or the various chromatography techniques, particularly column chromatography.

In step A5, the compound of formula (X) is converted to a compound of formula (IIa) by deprotection of the amino group at the 6-position of the thiazepine ring. The reactions involved are similar to those employed for removal of the amino-protecting groups represented by $R^{13}$ and $R^{14}$ from the compound of formula (VII) in step A2 and, depending upon the precise amino-protecting group or groups chosen, the same conditions and reagents as described in more detail in step A2 may be employed in step A5. After the reaction, the reaction product may be separated from the reaction mixture, as described in relation to step A2 and may then, if necessary, be further purified by such conventional techniques as recrystallization and/or the various chromatography techniques, particularly column chromatography.

Compounds of formula (II) in which m is 1 or 2, that is to say compounds of formula (IIb), may be prepared as illustrated in the following reaction scheme:

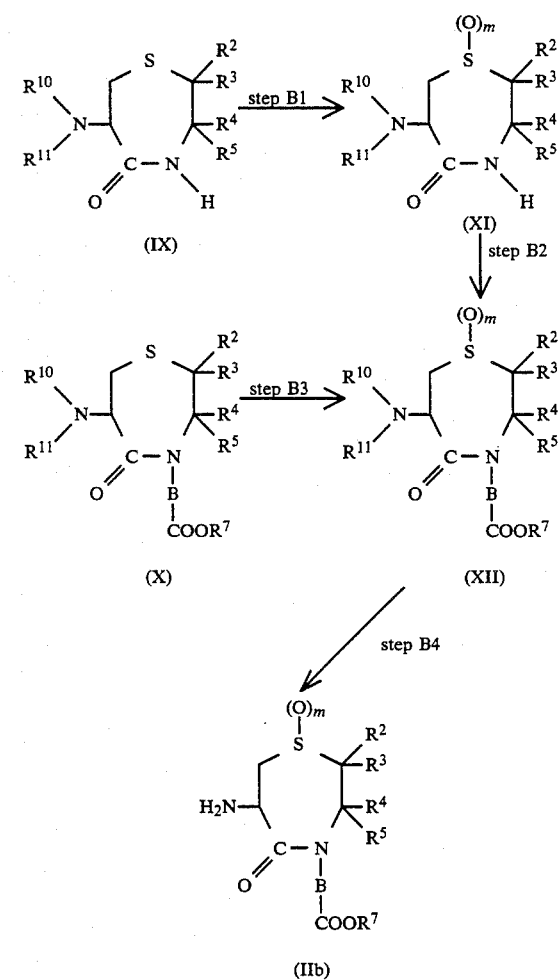

In the above formulae, $R^2$, $R^3$, $R^4$, $R^5$, B and $R^7$ are as defined above and m is 1 or 2.

In step B1 or B3 of this reaction sequence, the compound of formula (IX) or (X) (prepared as illustrated in steps A3 or A4 above) is oxidized to give, respectively, a compound of formula (XI) or (XII). The reaction is preferably effected in the presence of a solvent, the nature of which is not critical, provided that it has no adverse effect upon the reaction. Suitable solvents include: water; acids, preferably carboxylic acids and more preferably aliphatic carboxylic acids, such as acetic acid or formic acid; alcohols, such as methanol or ethanol; ethers, such as tetrahydrofuran or dioxane; ketones, such as acetone; halogenated hydrocarbons, particularly halogenated aliphatic hydrocarbons, such as methylene chloride or chloroform; or hydrocarbons, particularly aromatic hydrocarbons, such as benzene or toluene. For the oxidation reaction, any oxidizing agent known for the oxidization of sulfides to sulfoxides (m=1) or sulfones (m=2) may be employed. Examples of suitable oxidizing agents include such organic oxidizing agents as peracetic acid or m-chloroperbenzoic acid and such inorganic oxidizing agents as hydrogen peroxide, ozone or various periodates. The reaction will take place over a wide range of temperatures, for example from $-80°$ C. to $+100°$ C., and the time required for the reaction will vary, depending upon the nature of the reagents, the reaction conditions (notably reaction temperature) and the desired product. By controlling the nature and amount of oxidizing agent, the reaction temperature and the reaction time, it is possible to prepare selectively either a sulfoxide [a compound of formula (IIb) in which m is 1] or a sulfone [a compound of formula (IIb) in which m is 2].

After the reaction, excess oxidizing agent may be removed, if necessary, by treatment with dimethyl sulfide, an aqueous solution of sodium thiosulfate or an aqueous solution of sodium sulfite. The product of the oxidative reaction, the compound of formula (XI) or (XII), may then be obtained from the reaction mixture by extraction with a suitable organic solvent, washing, drying and then distillation of the organic solvent.

In step B2, the compound of formula (XI) is N-alkylated, precisely as in step A4, employing the same reagents and reaction conditions. The compound of formula (XII) which is the product of step B2 or step B3 is then deprotected, as described in more detail in step A5, employing the same reagents and reaction conditions.

Compounds of formula (Ib):

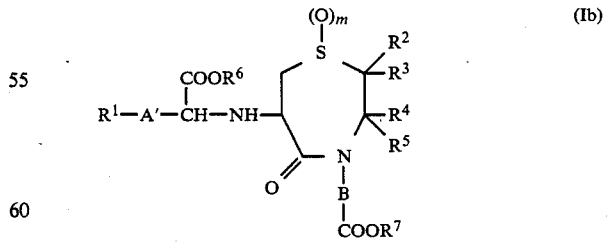

(in which $R^1$—$R^7$, B and m are as defined above and A' represents a direct single bond, a methylene group, an ethylene group or an oxymethyl group, that is any one of the bond or groups represented by A except the thiomethyl group) can be prepared by oxidation of a corresponding compound of formula (Ic):

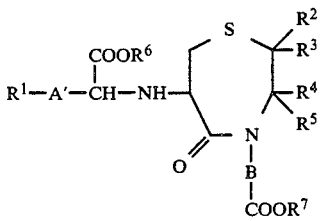

(in which R¹—R⁷, B and A' are as defined above). The reaction conditions are precisely the same as described above in relation to steps B1 and B3, employing the same reagents.

The processes described above will produce mixtures of optical isomers of the compounds of the invention, even if the starting materials are isolated optical isomers, as the reactions involved will racemize the compounds. However, by adopting alternative stereospecific reactions, it is possible to obtain specific isomers of the compounds of the invention. For example, in the reactions to produce the starting materials of formula (IIa), reaction of the compound of formula (V) with the compound of formula (VI) to produce the compound of formula (VII) tends to result in racemization of the carbon atom to which the cysteine nitrogen atom is attached, depending upon the sort of $R^{10}$, $R^{11}$ and/or $R^{12}$ and the base to be used, especially where $R^{12}$ is an ester residue in formula (V). However, if, instead of employing a compound of formula (VI) to react with the compound of formula (V), a compound of formula (XX):

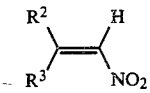

(in which $R^2$ and $R^3$ are as defined above) is reacted with the compound of formula (V) wherein $R^{12}$ is typically a hydrogen atom under a mild condition, the resulting compound of formula (XXI):

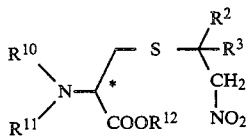

(in which $R^2$, $R^3$, $R^{10}$, $R^{11}$ and $R^{12}$ are as defined above) retains an optically active, non-racemized, carbon atom at that point marked with an asterisk. This compound of formula (XXI) may then be reduced by conventional means (well-known for the reduction of nitro groups to amino groups) to give a compound of formula (VII) in which $R^4$, $R^5$, $R^{13}$ and $R^{14}$ all represent hydrogen atoms and this may then subsequently be subjected to steps A2–A5 as already described.

In any case, where mixtures of optical isomers are produced at any stage during the preparation of the final product of formula (I) or the starting material of formula (II), the mixture of optical isomers may, if desired, be separated by conventional resolution methods, for example the formation of salts with optically active bases, such as cinchonine, cinchonidine, quinine or quinidine, or with optically active organic acids, e.g. l-camphorsulfonic acid or d-camphorsulfonic acid. Optical isomers can also be resolved by other known techniques, including various kinds of chromatography, fractional crystallization etc.

As noted above, the compounds of the present invention have the ability to inhibit the activity of ACE, the enzyme which converts angiotensin I to angiotensin II and also inactivates bradykinin. The physiological activity of the compounds of the invention can be evaluated by determining the concentration of the test compound required to inhibit the activity of ACE by 50% in vitro ($IC_{50}$), for example by the procedure of D. W. Cushman et al. [Biochemical Pharmachology, 20, 1637 (1971)]. Specifically, solutions of ACE extracted from rabbit lungs and, as substrate, hippurylhistidylleucine, to which had been added the test compound at various concentrations, were added to a borate buffer solution containing sodium chloride, and the pH was adjusted to a value of 8.3. The enzymatic reaction was allowed to proceed at 37° C. for 30 minutes, after which time the reaction was terminated by adding 1N aqueous hydrochloric acid. The hippuric acid formed by this reaction was extracted with ethyl acetate and the solvent was then distilled from the extract. The residual hippuric acid was dissolved in water. The amount of hippuric acid in the resulting aqueous solution was determined by the absorbency to ultraviolet radiation at 228 nm. These values were then plotted to form a curve indicating the relationship between the amount of hippuric acid formed and the concentration of the test compound. The $IC_{50}$ value can be obtained by reading on this curve the concentration of the test compound which reduces the amount of hippuric acid formed to one half of that formed when no test compound is present. The $IC_{50}$ values obtained for various of the compounds of the invention by this procedure are shown in the following Table. The compounds tested were as follows:

A: α-{6(R)-[1(S)-carboxy-3-phenylpropylamino]-5-oxo-3(R)-phenylperhydro-1,4-thiazepin-4-yl}acetic acid (product of Example 6);

B: α-{6(R)-[1(S)-carboxy-3-phenylpropylamino]-3(R)-isopropyl-5-oxoperhydro-1,4-thiazepin-4-yl}acetic acid (product of Example 29);

C: α-[6-(1-carboxy-3-phenylpropylamino)-5-oxo-2-phenylperhydro-1,4-thiazepin-4-yl]acetic acid (product of Example 13);

D: α-[6-(1-carboxy-3-phenylpropylamino)-5-oxo-2-(3-thienyl)perhydro-1,4-thiazepin-4-yl]acetic acid (product of Example 44);

E: α-[6-(1-carboxy-3-phenylpropylamino)-5-oxo-2-(2-thienyl)perhydro-1,4-thiazepin-4-yl]acetic acid (product of Example 51);

F: α-[6-(1-carboxy-3-phenylpropylamino)-2-(2-furyl)-5-oxoperhydro-1,4-thiazepin-4-yl]acetic acid (product of Example 58);

G: α-{6(R)-[1(S)-carboxy-3-phenylpropylamino]-5-oxo-3(S)-(2-thienyl)perhydro-1,4-thiazepin-4-yl}acetic acid (product of Example 18);

H: α-[6-(1-carboxy-3-phenylpropylamino)-2-(1-naphthyl)-5-oxoperhydro-1,4-thiazepin-4-yl]acetic acid (product of Example 38);

I: α-[6-(1carboxy-3-phenylpropylamino)-2-(2-naphthyl)-5-oxoperhydro-1,4-thiazepin-4-yl]acetic acid (product of Example 41);

J: α-{6(R)-[1(S)-carboxy-3-phenylpropylamino]-3(R)-methyl-5-oxoperhydro-1,4-thiazepin-4-yl}acetic acid (product of Example 32);

K: α-{3(S)-benzyl-6(R)-[1(S)-carboxy-3-phenyl-propylamino]-5-oxoperhydro-1,4-thiazepin-4-yl}acetic acid (product of Example 35).

TABLE

| Test Compound | IC$_{50}$ (moles/liter) |
|---|---|
| A | $1.1 \times 10^{-9}$ |
| B | $1.6 \times 10^{-9}$ |
| C | $2.4 \times 10^{-9}$ |
| D | $2.5 \times 10^{-9}$ |
| E | $2.4 \times 10^{-9}$ |
| F | $3.0 \times 10^{-9}$ |
| G | $1.4 \times 10^{-9}$ |
| H | $1.6 \times 10^{-9}$ |
| I | $2.0 \times 10^{-9}$ |
| J | $3.0 \times 10^{-9}$ |
| K | $1.3 \times 10^{-9}$ |

As can be clearly seen from the results in the above Table, the compounds of the invention inhibit ACE activity at very low concentrations and are thus useful as diagnostic, preventative and therapeutic agents for hypertensive patients; likewise, salts of these compounds would have similar activities.

For practical, therapeutic use, the compounds of the invention are preferably administered in combination with suitable pharmaceutically acceptable carriers, vehicles or diluents. The compounds can be administered orally or non-orally (e.g. parenterally by intravenous or intramuscular injection) and the form of the composition will, of course, be determined by the intended route of administration. For oral administration, the compounds of the invention may, for example, be administered as powders, granules, tablets, capsules, syrups or elixirs. For parenteral administration, the compounds will be administered in the form of a suitable injectible composition, in which the compound of the invention is dissolved or suspended in a pyrogen-free injectible medium. The dose will vary depending upon the nature and severity of the disorder, as well as upon the age, condition and body weight of the patient. For example, for the therapy of an adult human patient, the dose at each administration would preferably be from 0.5 to 1000 mg, more preferably from 5 to 100 mg, for oral administration, whilst the preferred dose at each administration for intravenous injection is from 0.5 to 100 mg, more preferably from 0.5 to 10 mg. One or more of these doses, preferably from 1 to 3 doses, may be administered daily.

The invention is further illustrated by the following Examples, which describe the preparation of various of the compounds of the invention, including separation and/or preparation of individual isomers thereof. In the nuclear magnetic resonance spectra reported in certain of these Examples, the abbreviation "Ph" signifies the phenyl group. The values for optical rotation were all measured with the sodium D-line, i.e. all values are $[\alpha]_D$.

EXAMPLE 1 t-Butyl α-[6(R)-(1-ethoxycarbonyl-3-phenylpropylamino)-5-oxo-3(R)-phenylperhydro-1,4-thiazepin-4-yl]acetate (Compound No. 74)

1(a) 2-(R)-t-Butoxycarbonylamino-2-phenylethanol 10.5 g of di-t-butyl pyrocarbonate were added, with ice-cooling, to a mixture of 6 g of D-(−)-α-phenyl-glycinol and 6 ml of triethylamine dissolved in 100 ml of methylene chloride, and the mixture was stirred for 15 hours at room temperature. The reaction solution was then concentrated by evaporation under reduced pressure, and the residue was dissolved in ethyl acetate and water. The ethyl acetate layer was separated, washed with an aqueous solution of potassium hydrogen sulfate and an aqueous solution of sodium bicarbonate, and then dried over anhydrous magnesium sulfate. The solvent was distilled off, leaving the title compound as crystals. The compound was then washed with small amounts of diisopropyl ether and cyclohexane, to yield 9.9 g of the purified compound, melting at 136°–138° C.

Nuclear Magnetic Resonance Spectrum [CDCl$_3$+sufficient (CD$_3$)$_2$SO to dissolve the product] δ ppm: 1.36 (9H, singlet, t-butyl); 3.6–3.75 (3H, multiplet, CH$_2$—OH); 4.3–4.7 (1H, multiplet, Ph—CH—N); 6.34 (1H, broad doublet, J=7 Hz, NH); 7.20 (5H, singlet, phenyl protons).

1(b) 1(R)-t-Butoxycarbonylamino-2-methanesulfonyloxy-1-phenylethane 11 ml of pyridine and then 6.6 ml of methanesulfonyl chloride were added dropwise, at room temperature, to a solution containing 9.9 g of 2(R)-t-butoxycarbonylamino-2-phenylethanol [prepared as described in step (a) above] dissolved in 120 ml of methylene chloride. This mixture was stirred for 15 hours at room temperature, after which the solvent was removed by distillation. The residue was dissolved in ethyl acetate and water and the ethyl acetate layer was separated. This layer was washed with an aqueous solution of potassium hydrogen sulfate and an aqueous solution of sodium bicarbonate and then dried over anhydrous magnesium sulfate, after which the solvent was distilled off. The crystalline residue was collected by filtration and washed with a small amount of diisopropyl ether and cyclohexane to give 12.2 g of the title compound, melting at 108°–109° C.

Nuclear Magnetic Resonance Spectrum (CDCl$_3$) δ ppm: 1.42 (9H, singlet, t-butyl); 2.84 (3H, singlet, CH$_3$SO$_2$); 4.36 (2H, doublet, J=5 Hz, C—CH$_2$—O); 4.7–5.4 (2H, multiplet, —NH—CH—Ph); 7.27 (5H, singlet, phenyl protons).

1(c) Benzhydryl ester of S-[2-(R)-t-butoxycarbonylamino-2-phenylethyl]-N-phthaloyl-L-cysteine 7.26 g of sodium bicarbonate were added, under an atmosphere of nitrogen gas, to a mixture of 11.7 g of L-cysteine p-toluenesulfonate and 8.8 g of N-ethoxycarbonylphthalimide dissolved in 80 ml of dimethylformamide, and then the mixture was stirred for 3.5 hours at 90°–100° C. The reaction mixture was then cooled and dissolved in a mixture of ethyl acetate and an aqueous solution of potassium hydrogen sulfate; the aqueous layer was acidified; and then the ethyl acetate layer was separated. The separated ethyl acetate layer was washed with an aqueous solution of sodium chloride and then dried over anhydrous magnesium sulfate. 8.6 g of diphenyldiazomethane were then added. The resulting mixture was stirred for 1 hour under a stream of nitrogen and then the solvent was removed by distillation. The residue was dissolved in 140 ml of dimethyl-formamide, and then 12.2 g of 2(R)-t-butoxycarbonylamino-2-methanesulfonyloxy-1-phenylethane [prepared as described in step (b) above] and 12.2 g of sodium carbonate were added. The mixture was then stirred for 16 hours at 70° C. under a stream of nitrogen. The reaction mixture was then dissolved in ethyl acetate and water; the ethyl acetate layer was separated, washed with an aqueous solution of sodium chloride and dried over anhydrous magnesium sulfate. The solvent was distilled off, and the residue was subjected to silica gel column chromatography using a 1:4 by volume mixture of ethyl acetate and cyclohexane as the eluent; 9.9 g of the title compound were obtained as an amorphous substance.

Nuclear Magnetic Resonance Spectrum (CDCl$_3$) δ ppm: 1.34 (9H, singlet, t-butyl); 2.88 (2H, broad doublet, J=6 Hz, S—CH$_2$); 3.28 (2H, broad doublet, J=8 Hz, S—CH$_2$); 4.6–5.5 (3H, multiplet, NH, N—CH—CO, Ph—CH—N); 6.91 (1H, singlet, CHPh$_2$); 7.23 (10H, singlet, (C$_6$H$_5$)$_2$CH); 7.28 (5H, singlet, C$_6$H$_5$CH—); 7.5–7.9 (4H, multiplet, phthaloyl protons).

1(d) S-[2(R)-Amino-2-phenylethyl]-N-phthaloyl-L-cysteine trifluoroacetate 50 ml of trifluoroacetic acid were added, with ice-cooling, to solution containing 9.9 g of the benzhydryl ester of S-[2(R)-t-butoxycarbonylamino-2-phenylethyl]-N-phthaloyl-L-cysteine [prepared as described in step (c) above] dissolved in 50 ml of anisole, and the mixture was allowed to react for 2 hours at room temperature. The reaction solution was concentrated by evaporation under reduced pressure, diisopropyl ether was added to the residue and the desired compound was obtained by filtration as a crude powder in a yield of 8.6 g. This crude compound was subjected to the next step of cyclization without purification.

1(e) 5-Oxo-3(R)-phenyl-6(R)-phthalimidoperhydro-1,4-thiazepine

At room temperature, 9.8 g of diphenylphosphoryl azide were added dropwise, followed by 6.1 ml of N-methylmorpholine, to a solution containing 8.6 g of S-[2-(R)-amino-2-phenylethyl]-N-phthaloyl-L-cysteine trifluoroacetate [prepared as described in step (d) above] dissolved in 50 ml of dimethylformamide and 200 ml of methylene chloride, and the mixture was stirred for 16 hours. The solution was concentrated by evaporation of the methylene chloride, and the desired substance separated out as crystals during the addition of 100 ml of ethyl acetate and then an aqueous solution of sodium chloride to the reaction mixture which continued to be shaken and stirred. These crystals were then collected by filtration and washed with water and a small amount of ethyl acetate, to give 2.25 g of the title compound, melting at 280°–282° C.

Nuclear Magnetic Resonance Spectrum [(CD$_3$)$_2$SO] δ ppm: 2.95 (2H, broad doublet, J=7 Hz, SCH$_2$); 3.40 (2H, broad doublet, J=6 Hz, SCH$_2$); 5.00 (1H, broad quartet, J=7 Hz, HN—CHPh); 5.50 (1H, broad triplet, J=6 Hz, N—CH—CO); 7.1–7.5 (5H, multiplet, phenyl protons); 7.7 (1H, broad doublet, J=7 Hz, NH); 7.77 (4H, singlet, phthaloyl protons).

1(f) t-Butyl α-[5-oxo-3(R)-phenyl-6(R)-phthalimidoperhydro-1,4-thiazepin-4-yl]acetate 270 mg of a 50% w/w suspension of sodium hydride in mineral oil were added to a solution containing 5 ml of hexamethylphosphoric triamide and 1.9 g of 5-oxo-3(R)-phenyl-6(R)-phthalimidoperhydro-1,4-thiazepine [prepared as described in step (e) above] dissolved in 20 ml of dimethylformamide, and the mixture was stirred for 5 minutes at room temperature, 1.8 g of t-butyl bromoacetate was then added to the mixture. The resulting mixture was stirred for 1 hour at room temperature, after which a further 0.2 g of a 55% w/w suspension of sodium hydride in oil and 1 g of t-butyl bromoacetate were added. The mixture was stirred for a further 1 hour at room temperature. Ethyl acetate was then added to the mixture, and the mixture was washed with an aqueous solution of sodium chloride and then dried over anhydrous magnesium sulfate, after which the solvent was distilled off. The residue was subjected to silica gel column chromatography, using a 1:40 by volume mixture of ethyl acetate and methylene chloride as eluent, to give 1.65 g of the title compound as an amorphous substance.

Nuclear Magnetic Resonance Spectrum (CDCl$_3$) δ ppm: 1.32 (9H, singlet, t-butyl); 2.8–4.0 (6H, multiplet, CH$_2$SCH$_2$, NCH$_2$CO); 5.30 (1H, broad doublet, J=8 Hz, N—CH—Ph); 5.72 (1H, doublet of doublets, J=4 & 7.5 Hz, N—CH—CO);
7.30 (5H, singlet, phenyl protons);
7.45–7.85 (4H, multiplet, phthaloyl protons).

1(g) t-Butyl α-[6(R)-amino-5-oxo-3(R)-phenylperhydro-1,4-thiazepin-4-yl]acetate 0.7 ml of methylhydrazine was added to a solution containing 1.65 g of t-butyl α-[5-oxo-3(R)-phenyl-6(R)-phthalimidoperhydro-1,4-thiazepin-4-yl]acetate [prepared as described in step (f) above] dissolved in 20 ml of methylene chloride, and the mixture was allowed to stand at room temperature for 2 hours. The solvent and excess methylhydrazine were then distilled off, and the residue was dissolved in 10 ml of methylene chloride and 1 ml of methanol. The resulting solution was allowed to stand overnight at room temperature, after which the solvent was removed by distillation. A small amount of methylene chloride was added to the residue, and the precipitate was filtered off. The filtrate was subjected to silica gel column chromatography eluted with a 1:20 by volume mixture of methanol and methylene chloride, to give 1.1 g of the title compound as an amorphous substance.

Nuclear Magnetic Resonance Spectrum (CDCl$_3$) δ ppm: 1.38 (9H, singlet, t-butyl); 2.09 (2H, broad singlet, NH$_2$); 2.7–3.4 (4H, multiplet, CH$_2$SCH$_2$); 3.64 (2H, AB quartet, Δδ=0.47 ppm, J=18 Hz, NCH$_2$CO); 4.47 (1H, doublet of doublets, J=5 & 7 Hz, H$_2$N—CH—CO); 5.36 (1H, doublet of doublets, J=2 & 10 Hz, N—CH—Ph); 7.40 (5H, singlet, phenyl protons).

1(h) t-Butyl α-[6(R)-(1-ethoxycarbonyl-3-phenylpropylamino)-5-oxo-3(R)-phenylperhydro-1,4-thiazepin-4-yl]acetate 2.4 g of sodium carbonate were added to a mixture of 1.1 g of t-butyl α-[6(R)-amino-5-oxo-3(R)-phenylperhydro-1,4-thiazepin-4-yl]acetate [prepared as described in step (g) above]]and 1.4 g of ethyl 2-bromo-4-phenethylbutyrate dissolved in 15 ml of dimethylformamide, and this mixture was stirred for 15 hours at 65° C. The reaction mixture was then dissolved in ethyl acetate and an aqueous sodium chloride solution. The ethyl acetate layer was separated, washed with water and dried over anhydrous magnesium sulfate, after which the solvent was removed by distillation. The residue was subjected to silica gel column chromatography, using a 1:9 by volume mixture of ethyl acetate and methylene chloride as eluent. t-Butyl α-[6(R)-[1(R)-ethoxycarbonyl-3-phenylpropylamino]-5-oxo-3(R)-phenylperhydro-1,4-thiazepin-4-yl]acetate was obtained from the first fraction as an oily substance in a yield of 0.53 g.

Nuclear Magnetic Resonance Spectrum (CDCl$_3$) δppm: 1.25 (3H, triplet, J=7 Hz, CO$_2$CH$_2$CH$_3$); 1.37 (9H, singlet, t-butyl); 1.75-2.2 (2H, multiplet, PhCH$_2$—CH$_2$—S); 2.5-4.4 (11H, multiplet, PhCH$_2$—, CO—CH—NH—CH—CH$_2$—S—CH$_2$—, N—CH$_2$CO); 4.15 (2H, quartet, J=7 Hz, CO$_2$CH$_2$CH$_3$); 5.22 (1H, broad doublet, J=8.5 Hz, N—CH—Ph); 7.23 (5H, singlet, phenyl protons); 7.31 (5H, singlet, phenyl protons).

From the next fraction was obtained 0.60 g of t-butyl δ-[6(R)-[1(S)-ethoxycarbonyl-3-phenylpropylamino]-5-oxo-3(R)-phenylperhydro-1,4-thiazepin-4-yl]acetate as an oily substance.

Nuclear Magnetic Resonance Spectrum (CDCl$_3$) δppm: 1.27 (3H, triplet, J=7 Hz, CO$_2$CH$_2$CH$_3$); 1.36 (9H, singlet, t-butyl); 1.8-2.25 (2H, multiplet, PhCH$_2$—CH$_2$—C); 2.5-4.3 (11H, multiplet, PhCH$_2$, CO—CH—NH—CH—CH$_2$—S—CH$_2$—, N—CH$_2$CO); 4.15 (2H, quartet, J=7 Hz, CO$_2$CH$_2$CH$_3$); 5.26 (1H, broad doublet, J=8.5 Hz, N—CH—Ph); 7.18 (5H, singlet, phenyl protons); 7.29 (5H, singlet, phenyl protons).

EXAMPLE 2 t-Butyl δ-[6(R)-(1-ethoxycarbonyl-3-phenylpropylamino)-5-oxo-3(R)-phenylperhydro-1,4-thiazepin-4-yl]-acetate (Compound No. 74)

2 g of molecular sieve 4A were added to 10 ml of an ethanolic solution of t-butyl α-[6(R)-5-oxo-3(R)-phenylperhydro-1,4-thiazepin-4-yl]acetate [prepared as described in Example 1(g)] and 500 mg of ethyl 2-oxo-4-phenylbutyrate. The resulting ethanolic solution was stirred for 1 hour at room temperature, after which 6 ml of an ethanolic solution of 90 mg of sodium cyanoborohydride were added dropwise. The mixture was stirred for 6 hours at room temperature, after which 5 ml of an ethanolic solution of 400 mg of ethyl 2-oxo-4-phenylbutyrate and 90 mg of sodium cyanoborohydride were added, and the mixture was stirred for a further 16 hours at room temperature. The reaction mixture was then filtered, and the filtrate was condensed by evaporation under reduced pressure. The condensate was diluted with ethyl acetate and washed with an aqueous solution of potassium hydrogen sulfate and then with an aqueous solution of sodium bicarbonate. The resulting solution was dried over anhydrous magnesium sulfate, and then the solvent was distilled off. The residue was subjected to silica gel column chromatography as described in Example 1(h), to give 0.15 g of t-butyl α-{[6(R)-[1(R)-ethoxycarbonyl-3-phenylpropylamino]-5-oxo-3-(R)-phenylperhydro-1,4-thiazepin-4-yl}acetate and 0.15 g of t-butyl α-{6(R)-[1(R)-ethoxycarbonyl-3-phenylpropylamino]-5-oxo-3(R)-phenylperhydro-1,4-thiazepin-4-yl}acetate, having the same properties as the products of Example 1.

EXAMPLE 3

α-{6(R)-[1(R)-Ethoxycarbonyl-3-phenylpropylamino]-5-oxo-3(R)-phenylperhydro-1,4-thiazepin-4-yl}acetic acid (Compound No. 27)

0.53 g of t-butyl α-{6(R)-[1(R)-ethoxy-carbonyl-3-phenylpropylamino]-5-oxo-3(R)-phenylperhydro-1,4-thiazepin-4-yl}acetate [prepared as described in Examples 1 and 2] dissolved in 6 ml of anisole was reacted with 6 ml of trifluoroacetic acid for 2 hours at room temperature, after which the reaction product was condensed by evaporation under reduced pressure. 20 ml of water, 0.9 g of sodium bicarbonate, a small amount of ethyl acetate and a large amount of diisopropyl ether were added to the condensate, and the mixture was thoroughly shaken; the aqueous layer was then separated. Ethyl acetate was added to this aqueous layer and its pH was adjusted to a value of 2.8 with 3N hydrochloric acid. The ethyl acetate layer was separated and the aqueous layer was further extracted twice with ethyl acetate. All of the extracts in ethyl acetate were combined, and these combined extracts were dried over anhydrous magnesium sulfate. The solvent was distilled off, giving the title compound in the form of an amorphous solid, and in a yield of 270 mg.

Nuclear Magnetic Resonance Spectrum (CDCl$_3$) δppm: 1.25 (3H, triplet, J=7 Hz, CO$_2$—CH$_2$CH$_3$); 1.8-2.35 (2H, multiplet, PhCH$_2$CH$_2$); 2.5-4.55 (10H, multiplet, PhCH$_2$—, CO—CH—NH—CH—CH$_2$—S—CH$_2$, N—CH$_2$CO—); 4.14 (2H, quartet, J=7 Hz, CO$_2$CH$_2$CH$_3$); 5.17 (1H, broad doublet, J=8.5 Hz, N—CH—Ph); 7.17 (5H, singlet, phenyl protons); 7.22 (5H, singlet, phenyl protons).

EXAMPLE 4

α-{6(R)-[1(S)-Ethoxycarbonyl-3-phenylpropylamino]-5-oxo-3(R)-phenylperhydro-1,4-thiazepin-4-yl}acetic acid (Compound No. 27)

0.60 g of t-butyl α-{6(R)-[1(S)-ethoxycarbonyl-3-phenylpropylamino]-5-oxo-3(R)-phenylperhydro-1,4-thiazepin-4-yl}acetate was treated in the same manner as described in Example 3, to give the title compound in the form of an amorphous solid, and in a yield of 0.21 g.

Nuclear Magnetic Resonance Spectrum (CDCl$_3$) δppm: 1.28 (3H, triplet, J=7 Hz, CO$_2$CH$_2$CH$_3$); 1.9-2.4 (2H, multiplet, PhCH$_2$CH$_2$); 2.5-3.8 (9H, multiplet, PhCH$_2$, CH$_2$—S—CH$_2$, NCH$_2$CO, N—CH—CO); 4.65 (1H, broad triplet, J=4.5 Hz, N—CHCO); 5.19 (1H, broad doublet, J=8.5 Hz, N—CH—Ph); 7.14 (5H, singlet, phenyl protons); 7.22 (5H, singlet, phenyl protons); 8.90 (2H, broad singlet, CO$_2$H, NH).

EXAMPLE 5

α-{6(R)-[1(R)-Carboxy-3-phenylpropylamino]-5-oxo-3(R)-phenylperhydro-1,4-thiazepin-4-yl}acetic acid (Compound No. 28)

170 mg of α-{6(R)-[(R)-ethoxycarbonyl-3-phenylpropylamino]-5-oxo-3(R)-phenylperhydro-1,4-thiazepin-4-yl}acetic acid (prepared as described in Example 4) were dissolved in 0.8 ml of a 1% w/v aqueous solution of sodium hydroxide, and the resulting solution was allowed to stand for 18 hours at room temperature. 0.8 ml of 1N hydrochloric acid was added dropwise to this reaction product, and the pH of the mixture was adjusted to the value of 2.0. The title compound was precipitated as a powder following the dropwise addition; this was separated and washed with a small amount of water and ethyl acetate, to yield 70 mg of the title compound.

Nuclear Magnetic Resonance Spectrum [(CD$_3$)$_2$SO] δppm: 1.7-2.1 (2H, multiplet, PhCH$_2$CH$_2$); 2.4-3.4 (7H, multiplet, PhCH$_2$, N—CH—CO, CH$_2$SCH$_2$); 3.51 (2H, singlet, NCH$_2$CO); 4.33 (1H, broad triplet, J=5 Hz, N—CHCO), 5.30 (1H, broad doublet, J=9 Hz, N—

CH—Ph); 7.23 (5H, singlet, phenyl protons); 7.39 (5H, singlet, phenyl protons).

EXAMPLE 6

α-{6(R)-[1(S)-Carboxy-3-phenylpropylamino]-5-oxo-3(R)-phenylperhydro-1,4-thiazepin-4-yl}acetic acid
(Compound No. 28)

165 mg of α-{6-[1(S)-ethoxycarbonyl-3-phenylpropylamino]-5-oxo-3(R)-phenylperhydro-1,4-thiazepin-4-yl}acetic acid (prepared as described in Example 4) were treated as described in Example 5, to give 100 mg of the title compound as a solid.

Nuclear Magnetic Resonance Spectrum [(CD$_3$)$_2$SO] δppm: 1.65–2.2 (2H, multiplet, PhCH$_2$CH$_2$); 2.4–3.4 (7H, multiplet, PhCH$_2$, N—CH—CO, CH$_2$SCH$_2$); 3.55 (2H, singlet, NCH$_2$CO); 4.55 (1H, broad triplet, J=5 Hz, N—CHCO), 5.38 (1H, broad doublet, J=9 Hz, N—CH—Ph); 7.25 (5H, singlet, phenyl protons); 7.41 (5H, singlet, phenyl protons).

EXAMPLE 7 t-Butyl
α-{6-[1-ethoxycarbonyl-3-phenylpropylamino]-5-oxo-2-phenylperhydro-1,4-thiazepin-4-yl}-acetate
(Compound No. 75)

7(a) 2-t-Butoxycarbonylamino-1-phenylethanol 28 g of t-butoxycarbonyl azide were added at room temperature to 200 ml of a methylene chloride solution containing 25.3 g of DL-2-amino-1-phenylethanol and 45 ml of triethylamine, and the reaction mixture was allowed to stand overnight at room temperature. The reaction mixture was then condensed by evaporation under reduced pressure, and water and diisopropyl ether were added to the condensate. The mixture was thoroughly stirred. yielding the title compound in the form of insoluble crystals melting at 123°–124° C. in a yield of 20.6 g. These crystals were filtered off. The organic layer in the filtrate was separated and washed with an aqueous solution of potassium hydrogen sulfate and with an aqueous solution of sodium bicarbonate. The resulting solution was dried over anhydrous magnesium sulfate, and the solvent was distilled off. The crystals of the title compound in the residue were collected by filtration and washed with a mixture of diisopropyl ether and petroleum ether, yielding a further 18.7 g.

Nuclear Magnetic Resonance Spectrum [(CD$_3$)$_2$SO] δppm: 1.40 (9H, singlet, t-butyl); 3.15 (2H, multiplet, C—CH$_2$—N); 4.61 (1H, multiplet, Ph—CH—C); 5.12 (1H, doublet, J=4 Hz, OH); 6.00 (1H, broad triplet, NH); 7.24 (5H, singlet, phenyl protons).

7(b) 2-t-Butoxycarbonylamino-1-chloro-1-phenylethane

A mixture of 3.7 ml of pyridine and 2.2 ml of methanesulfonyl chloride was added dropwise to 35 ml of a solution of 3.5 g of 2-t-butoxycarbonylamino-1-phenylethanol [prepared as described in step (a) above] in methylene chloride and the reaction mixture was allowed to stand overnight at room temperature. The reaction mixture was condensed by evaporation under reduced pressure, and the residue was dissolved in a mixture of ethyl acetate and water. The ethyl acetate layer was separated, washed with water and then washed with an aqueous solution of potassium hydrogen sulfate and with an aqueous solution of sodium bicarbonate. The resulting solution was dried over anhydrous magnesium sulfate. The solvent was then distilled off. The residue was subjected to silica gel column chromatography using a 15:85 by volume mixture of ethyl acetate and cyclohexane as the eluent, to give 0.75 g of the title compound as crystals melting at 57°–59° C.

Nuclear Magnetic Resonance Spectrum (CDCl$_3$) δppm: 1.44 (9H, singlet, t-butyl); 3.4–3.7 (2H, multiplet, —CH$_2$N); 4.2–5.15 (2H, multiplet, NH, PhCHCl); 7.30 (5H, singlet, phenyl protons).

7(c) Benzhydryl ester of S-(2-t-butoxycarbonylamino-1-phenylethyl)-N-phthaloylcysteine The benzhydryl ester of N-phthaloyl-L-cysteine was prepared from 5.0 g of L-cysteine p-toluenesulfonate, 3.8 g of N-ethoxycarbonylphthalimide, 2.9 g of sodium bicarbonate and 3.3 g of diphenyldiazomethane, following the same procedure as described in Example 1(c).

5 g of sodium bicarbonate were added to 60 ml of a solution of the resulting compound and 3.9 g of 2-t-butoxycarbonylamino-1-chloro-1-phenylethane [prepared as described in step (b) above] in dimethylformamide, and the mixture was stirred at 65° C. for 40 hours. The reaction mixture was then diluted with ethyl acetate, washed with an aqueous solution of sodium chloride and then dried over anhydrous magnesium sulfate. The solvent was distilled off, and the residue was subjected to silica gel column chromatography using a 1:3 by volume mixture of ethyl acetate and cyclohexane as the eluent, giving the title compound in the form of an amorphous solid and in a yield of 4.0 g.

Nuclear Magnetic Resonance Spectrum (CDCl$_3$) δppm: 1.36 (9H, singlet, t-butyl); 3.15–3.7 (4H, multiplet, CH$_2$S, C—CH$_2$—N); 4.10 (1H, broad triplet, J=7 Hz, S—CH—Ph); 4.6–5.2 (2H, multiplet NH, N—CH—CO); 6.87 and 6.89 (together 1H, both singlets, CHPh$_2$); 7.24 (10H, singlet, phenyl protons of benzhydryl); 7.29 (5H, singlet, C$_6$H$_5$—C—); 6.6–6.9 (4H, multiplet, phthaloyl protons).

7(d) S-(2-Amino-1-phenylethyl)-N-phthaloylcysteine

A mixture of 40 ml of trifluoroacetic acid with 30 ml of an anisole solution containing 4.8 g of the benzhydryl ester of S-(2-t-butoxycarbonylamino-1-phenylethyl)-N-phthaloylcysteine [prepared as described in step (c) above] was allowed to stand for 4 hours at room temperature, and then the reaction product was condensed by evaporation under reduced pressure. The residual oily substance was washed by decantation using diisopropyl ether. After the washing, 50 ml of water were added to the resulting solution. 5 g of sodium bicarbonate were then added, with stirring, and 2.4 g of the title compound precipitated. This product was separated and then subjected to the subsequent cyclization reaction in step (e) without further purification.

7(e) 2-Phenyl-6-phthalimidoperhydro-1,4-thiazepin-5-one 830 mg of 1-hydroxybenzotriazole monohydrate and 1.13 g of N,N'-dicyclohexylcarbodiimide were added to 40 ml of a dimethylformamide solution containing 2.0 g of S-[2-amino-1-phenylethyl]-N-phthaloylcysteine [prepared as described in step (d) above], and the mixture was stirred for 4 hours at room temperature. 300 ml of ethyl acetate were added to this reaction mixture. Insoluble matter was removed by filtration, and the filtrate was washed with water, and then dried over anhydrous magnesium sulfate. The solvent was distilled off, leaving the title compound in crystalline form. The crystals were collected by filtration and washed with a small amount of ethyl acetate and diisopropyl ether, yielding 2.0 g of the title compound, which softens at a temperature around 200° C. and melts at 240°–247° C.

Nuclear Magnetic Resonance Spectrum [(CD₃)₂SO] δppm: 3.9–4.4 (5H, multiplet, Ph—CHS—, —CH₂S—, —CH₂N—); 5.38 (1H, doublet of doublets, J=3 & 9 Hz, N—CHCO); 7.41 (5H, singlet, phenyl protons); 7.93 (4H, singlet, phthaloyl protons); 8.18 (1H, broad triplet, J=6 Hz, NH).

7(f) t-Butyl α-[5-oxo-2-phenyl-6-phthalimidoperhydro-1,4-thiazepin-4-yl]acetate 0.35 g of a 50% w/w suspension of sodium hydride in oil, followed by 2 g of t-butyl bromoacetate were added to 20 ml of a dimethylformamide solution containing 1.9 g of 2-phenyl-6-phthalimidoperhydro-1,4-thiazepin-5-one [prepared as described in step (e) above], and the mixture was stirred for 1 hour at room temperature. The reaction mixture was then diluted with ethyl acetate, washed with water, and dried over anhydrous magnesium sulfate. The solvent was then distilled off, and the residue was subjected to silica gel column chromatography using a 1:20 by volume mixture of ethyl acetate and methylene chloride, so as to separate two diastereomers which are derived from the carbon atom at the 2-position. The isomer first eluted in a yield of 1.3 g, was called "diastereomer A", and was in the form of a crystalline powder, softening at around 100° C. and melting at 118° C.

Nuclear Magnetic Resonance Spectrum (CDCl₃) δppm: 1.47 (9H, singlet, t-butyl); 2.8–4.8 (7H, multiplet, N—CH—CH₂—S—, N—CH₂—CO, S—CH Ph—CH₂); 5.68 (1H, doublet of doublets, J=2 & 10 Hz, N—CH—CO); 7.40 (5H, singlet, phenyl protons); 7.65–8.0 (4H, multiplet phthaloyl protons).

The next isomer eluted, in a yield of 0.4 g, was called "diastereomer B" and was an amorphous solid.

Nuclear Magnetic Resonance Spectrum (CDCl₃) δppm: 1.40 (9H, singlet, t-butyl); 2.45–4.5 (7H, multiplet, N—CH—CH₂—S, N—CH₂—CO, S—CH Ph—CH₂); 5.52 (1H, doublet of doublets, J=6 & 9 Hz, N—CH—CO); 7.2–7.5 (5H, multiplet, phenyl protons); 7.6–7.8 (4H, multiplet, phthalyl protons).

7(g) t-Butyl α-[6-amino-5-oxo-2-phenylperhydro-1,4-thiazepin-4-yl]acetate [derived from diastereomer A in step (f)]

1.2 g of diastereomer A of t-butyl α-[5-oxo-2-phenyl-6-phthalimidoperhydro-1,4-thiazepin-4-yl]acetate [prepared as described in step (f) above] were subjected to dephthaloylization with methylhydrazine in the same manner as described in Example 1(g), to give 0.66 g of the title compound as an amorphous solid.

Nuclear Magnetic Resonance Spectrum (CDCl₃) δppm: 1.46 (9H, singlet, t-butyl); 2.05 (2H, broad singlet, NH₂); 2.4–4.5 (8H, multiplet, —N—CH—CH₂-SCH—CH₂—, N—CH₂CO); 7.29 (5H, singlet, phenyl protons).

7(h) t-Butyl α-[6-amino-5-oxo-2-phenylperhydro-1,4-thiazepin-4-yl]acetate [derived from diastereomer B in step (f)]

0.4 g of diastereomer B of t-butyl α-[5-oxo-2-phenyl-6-phthalimidoperhydro-1,4-thiazepin-4-yl]acetate [prepared as described in step (f) above] was subjected to dephthaloylization with methylhydrazine in the same manner as described in Example 1(g), to give 0.22 g of the title compound as an amorphous solid.

Nuclear Magnetic Resonance Spectrum (CDCl₃) δ ppm: 1.41 (9H, singlet, t-butyl); 2.13 (2H, broad singlet, NH₂); 2.7–3.1 (3H, multiplet, C—CH₂—S—CH—Ph); 4.10–4.50 (5H, multiplet, N—CH₂CO, N—CH—CO, N—CH₂—C—Ph); 7.36 (5H, singlet, phenyl protons).

7(i) t-Butyl α-{6-[1-ethoxycarbonyl-3-phenylpropylamino]-5-oxo-2-phenylperhydro-1,4-thiazepin-4-yl}acetate (Compound No. 75)

0.66 g of the isomer of t-butyl α-[6-amino-5-oxo-2-phenylperhydro-1,4-thiazepin-4-yl]acetate produced as described in step (g) above was subjected to N-alkylation with 0.84 g of ethyl 2-bromo-4-phenylbutyrate following the procedure described in Example 1(h). The resulting compound was subjected to silica gel column chromatography using a 1:20 by volume mixture of ethyl acetate and methylene chloride as eluent. From the first fraction was obtained 0.28 g of t-butyl α-{6-[1-ethoxycarbonyl-3-phenylpropylamino]-5-oxo-2-phenylperhydro-1,4-thiazepin-4-yl}acetate as an oil.

Nuclear Magnetic Resonance Spectrum (CDCl₃) δ ppm; 1.25 (3H, triplet, J=7Hz, CO₂CH₂CH₃); 1.47 (9H, singlet, t-butyl); 1.8–2.25 (2H, multiplet, Ph—CH₂CH₂); 2.4–4.5 (14H, multiplet, Ph—CH₂, CO—CH—NH—CH—CH₂—S—CH—CH₂, NCH₂CO, CO₂CH₂CH₃); 7.25 (5H, singlet, phenyl protons); 7.33 (5H, singlet, phenyl protons).

From the second fraction to be eluted was obtained 0.26 g of the other isomer arising from the asymmetric carbon atom at the 6-position of the compound obtained above as an oil.

Nuclear Magnetic Resonance Spectrum (CDCl₃) δ ppm: 1.25 (3H, triplet, J=7 Hz, CO₂CH₂CH₃); 1.46 (9H, singlet, t-butyl); 1.8–2.25 (2H, multiplet, Ph—CH₂CH₂); 2.5–4.5 (14H, multiplet, Ph—CH₂, CO—CH—NH—CH—CH₂—S—CH—CH₂, NCH₂CO, CO₂CH₂CH₃); 7.26 (5H, singlet, phenyl protons); 7.34 (5H, singlet, phenyl protons).

7(j) t-Butyl α-{6-[1-ethoxycarbonyl-3-phenylpropylamino]-5-oxo-2-phenylperhydro-1,4-thiazepin-4-yl}acetate (Compound No. 75)

0.22 g of the isomer of t-butyl α-[6-amino-5-oxo-2-phenylperhydro-1,4-thiazepin-4-yl]acetate [prepared as described in step (h) above] was subjected to N-alkylation with 0.28 g of ethyl 2-bromo-4-phenylbutyrate in the same manner as described in Example 1(h). The resulting product was subjected to silica gel column chromatography, using a 1:20 by volume mixture of ethyl acetate and methylene chloride as the eluent. From the fraction first eluted was obtained 0.14 g of t-butyl α-{6-[1-ethoxycarbonyl-3-phenylpropylamino]-5-oxo-2-phenylperhydro-1,4-thiazepin-4-yl}acetate as an oil.

Nuclear Magnetic Resonance Spectrum (CDCl₃) δ ppm: 1.25 (3H, triplet, J=7 Hz, CO₂CH₂CH₃); 1.41 (9H, singlet, t-butyl); 1.8–2.25 (2H, multiplet, PhCH₂CH₂); 2.6–4.5 (14H, multiplet, PhCH₂, CO—CH—NH—CH—CH₂—S—CH—CH₂, NCH₂CO, CO₂CH₂CH₃); 7.26 (5H, singlet, phenyl protons); 7.36 (5H, singlet, phenyl protons).

From the fraction eluted subsequently was obtained 0.08 g of the other isomer arising from the asymmetric carbon atom at the 6-position of the compound obtained above as an oil.

Nuclear Magnetic Resonance Spectrum (CDCl$_3$) δ ppm: 1.25 (3H, triplet, J=7 Hz, CO$_2$CH$_2$CH$_3$); 1.44 (9H, singlet, t-butyl); 1.8–2.25 (2H, multiplet, PhCH$_2$CH$_2$); 2.4–4.5 (14H, multiplet, PhCH$_2$, CO—CH—NH—CH—CH$_2$—S—CH—CH$_2$, NCH$_2$CO, CO$_2$CH$_2$CH$_3$); 7.26 (5H, singlet, phenyl protons); 7.34 (5H, singlet, phenyl protons).

EXAMPLE 8

α-{6-[1-Ethoxycarbonyl-3-phenylpropylamino]-5-oxo-2-phenylperhydro-1,4-thiazepin-4-yl}acetic acid (Compound No. 29)

0.28 g of t-butyl α-{6-[1-ethoxycarbonyl-3-phenylpropylamino]-5-oxo-2-phenylperhydro-1,4-thiazepin-4-yl}acetate [prepared as described in Example 7(i) above (the first fraction)] was subjected to de-t-butylation with trifluoracetic acid in the same manner as described in Example 3, giving the title compound as an amorphous solid in a yield of 0.18 g.

Nuclear Magnetic Resonance Spectrum (CDCl$_3$) δ ppm: 1.25 (3H, triplet, J=7 Hz, CO$_2$CH$_2$CH$_3$); 1.8–2.25 (2H, multiplet, PhCH$_2$CH$_2$); 2.5–4.6 (13H, multiplet, PhCH$_2$, CO—CH—NH—CH—CH$_2$—S—CH—CH$_2$—, N—CH$_2$CO, CO$_2$CH$_2$CH$_3$); 7.25 (5H, singlet, phenyl protons); 7.34 (5H, singlet, phenyl protons).

EXAMPLE 9

α-{6-[1-Ethoxycarbonyl-3-phenylpropylamino]-5-oxo-2-phenylperhydro-1,4-thiazepin-4-yl}acetic acid (Compound No. 29)

0.26 g of t-butyl α-{6-[1-ethoxycarbonyl-3-phenylpropylamino]-5-oxo-2-phenylperhydro-1,4-thiazepin-4-yl}acetate [prepared as described in Example 7(i) above (the second fraction)] was subjected to de-t-butylation with trifluoroacetic acid in the manner described in Example 3, giving the title compound as an amorphous solid in a yield of 0.17 g.

Nuclear Magnetic Resonance Spectrum (CDCl$_3$) δ ppm: 1.26 (3H, triplet, J=7 Hz, CO$_2$CH$_2$CH$_3$); 1.8–2.25 (2H, multiplet, PhCH$_2$CH$_2$); 2.5–4.6 (13H, multiplet, PhCH$_2$, CO—CH—NH—CH—CH$_2$—S—CH—CH$_2$—, N—CH$_2$CO, CO$_2$CH$_2$CH$_3$); 7.25 (5H, singlet, phenyl protons); 7.36 (5H, singlet, phenyl protons).

EXAMPLE 10

α-{6-[1-Ethoxycarbonyl-3-phenylpropylamino]-5-oxo-2-phenylperhydro-1,4-thiazepin-4-yl}acetic acid (Compound No. 29)

0.14 g of t-butyl α-{6-[1-ethoxycarbonyl-3-phenylpropylamino]-5-oxo-2-phenylperhydro-1,4-thiazepin-4-yl}acetate [prepared as described in Example 7(j) above (the first fraction)] was subjected to de-t-butylation with trifluoracetic acid in the manner described in Example 3, giving the title compound as an amorphous solid in a yield of 0.09 g.

Nuclear Magnetic Resonance Spectrum (CDCl$_3$) δ ppm: 1.25 (3H, triplet, J=7 Hz, CO$_2$CH$_2$CH$_3$); 1.8–2.25 (2H, multiplet, PhCH$_2$CH$_2$); 2.5–4.5 (13H, multiplet, PhCH$_2$, CO—CH—NH—CH—CH$_2$—SCH—CH$_2$, N—CH$_2$CO, COCH$_2$CH$_3$); 7.25 (5H, singlet, phenyl protons); 7.35 (5H, singlet, phenyl protons).

EXAMPLE 11

α-{6-[1-Ethoxycarbonyl-3-phenylpropylamino]-5-oxo-2-phenylperhydro-1,4-thiazepin-4-yl}acetic acid (Compound No. 29)

0.08 g of t-butyl α-{6-[1-ethoxycarbonyl-3-phenylpropylamino]-5-oxo-2-phenylperhydro-1,4-thiazepin-4-yl}acetate [prepared as described in Example 7(j) above (the second fraction)] was subjected to de-t-butylation with trifluoracetic acid in the manner described in Example 3, giving the title compound as an amorphous solid in a yield of 0.05 g.

Nuclear Magnetic Resonance Spectrum (CDCl$_3$) δ ppm: 1.26 (3H, triplet, J=7 Hz, CO$_2$CH$_2$CH$_3$); 1.8–2.25 (2H, multiplet, PhCH$_2$CH$_2$); 2.5–5.1 (13H, multiplet, PhCH$_2$, CO—CH—NH—CH—CH$_2$—S—CH—CH$_2$—N—CH$_2$CO, CO$_2$CH$_2$CH$_3$); 7.25 (5H, singlet, phenyl protons); 7.34 (5H, singlet, phenyl protons).

EXAMPLE 12

α-{6-[1-Carboxy-3-phenylpropylamino]-5-oxo-2-phenylperhydro-1,4-thiazepin-4-yl}acetic acid (Compound No. 30)

0.18 of α-{6-ethoxycarbonyl-3-phenylpropylamino]-5-oxo-2-phenylperhydro-1,4-thiazepin-4-yl}acetic acid (prepared as described in Example 8 above) was hydrolysed with aqueous sodium hydroxide in the manner described in Example 5, giving the title compound as a powder in a yield of 0.14 g.

Nuclear Magnetic Resonance Spectrum [(CD$_3$)$_2$SO] δ ppm: 1.75–2.15 (2H, multiplet, PhCH$_2$CH$_2$); 2.55–4.6 (11H, multiplet, PhCH$_2$, —CH—NH—CH—CH$_2$—S—CH—CH$_2$, NCH$_2$CO); 7.30 (5H, singlet, phenyl protons); 7.40 (5H, multiplet, phenyl protons).

EXAMPLE 13

α-{6-[1-Carboxy-3-phenylpropylamino]-5-oxo-2-phenylperhydro-1,4-thiazepin-4-yl}acetic acid (Compound No. 30)

0.17 g of α-{6-[1-ethoxycarbonyl-3-phenylpropylamino]-5-oxo-2-phenylperhydro-1,4-thiazepin-4-yl}acetic acid (prepared as described in Example 9 above) was hydrolysed with caustic soda in the manner described in Example 5, giving the title compound as a powder in a yield of 0.13 g.

Nuclear Magnetic Resonance Spectrum [(CD$_3$)$_2$SO] δ ppm: 1.75–2.1 (2H, multiplet, PhCH$_2$CH$_2$); 2.55–4.5 (11H, multiplet, PhCH$_2$, —CH—NH—CH—CH$_2$—S—CH—CH$_2$, NCH$_2$CO); 7.27 (5H, singlet, phenyl protons); 7.38 (5H, singlet, phenyl protons).

EXAMPLE 14

α-{6-[1-Carboxy-3-phenylpropylamino]-5-oxo-2-phenylperhydro-1,4-thiazepin-4-yl}acetic acid (Compound No. 30)

90 mg of α-{6-[1-ethoxycarbonyl-3-phenylpropylamino]-5-oxo-2-phenylperhydro-1,4-thiazepin-4-yl}acetic acid (prepared as described in Example 10 above) was hydrolysed with aqueous sodium hydroxide in the manner described in Example 5, giving the title compound as a powder in a yield of 70 mg.

Nuclear Magnetic Resonance Spectrum [(CD$_3$)$_2$SO] δ ppm: 1.7–2.1 (2H, multiplet, PhCH$_2$CH$_2$); 2.55–4.5 (11H, multiplet, PhCH$_2$, —CH—NH—CH—CH$_2$—S—CH—CH$_2$, NCH$_2$CO); 7.27 (5H, singlet, phenyl protons); 7.40 (5H, singlet, phenyl protons).

EXAMPLE 15

α-{6-[1-Carboxy-3-phenylpropylamino]-5-oxo-2-phenylperhydro-1,4-thiazepin-4-yl}acetic acid
(Compound No. 30)

50 mg of α-{6-[1-ethoxycarbonyl-3-phenylpropylamino]-5-oxo-2-phenylperhydro-1,4-thiazepin-4-yl}acetic acid (prepared as described in Example 11 above) was hydrolyzed with aqueous sodium hydroxide in the manner described in Example 5, giving the title compound as a powder in a yield of 40 mg.

Nuclear Magnetic Resonance Spectrum [$(CD_3)_2SO$] δ ppm: 1.7–2.1 (2H, multiplet, PhCH$_2$C$\underline{H}_2$); 2.6–5.1 (9H, multiplet, PhC$\underline{H}_2$, —C$\underline{H}$—NH—C$\underline{H}$—C$\underline{H}_2$—S—C$\underline{H}$—C$\underline{H}_2$); 3.97 ($\overline{2H}$, AB quartet, Δδ=0.27 ppm, J=19 Hz, NC$\underline{H}_2$CO); 7.26 (5H, singlet, phenyl protons); 7.40 (5H, singlet, phenyl protons).

EXAMPLE 16 t-Butyl α-{6(R)-[1-ethoxycarbonyl-3-phenylpropylamino]-5-oxo-3(S)-(2-thienyl)perhydro-1,4-thiazepin-4-yl)acetate
(Compound No. 201)

16(a) 2(S)-t-Butoxycarbonylamino-2-(2-thienyl)ethanol 5.0 g of D-(2-thienyl)glycinol were subjected to t-butoxycarbonylation in the manner described in Example 1(a), giving 6.5 g of the title compound, melting at 79° C.

Nuclear Magnetic Resonance Spectrum (CDCl$_3$) δ ppm: 1.43 (9H, singlet, t-butyl); 2.78 (1H, triplet, J=6.5 Hz, OH); 3.81 (2H, doublet of doublets, J=5 & 6.5 Hz, CH$_2$); 4.98 (1H, doublet of triplets, J=5 & 7 Hz, N—C$\underline{H}$—CO); 5.34 (1H, broad doublet, J=7 Hz, NH); 6.95 (2H, multiplet, protons at C3 and C4 of the thiophene ring); 7.20 (1H, multiplet, proton at C5 of the thiophene ring).

16(b) 1(S)-t-Butoxycarbonylamino-1-(2-thienyl)-2-methanesulfonyloxyethane 7.07 g of 2-(S)-t-butoxycarbonylamino-2-(2-thienyl)ethanol [prepared as described in step (a) above] was subjected to methaneseulfonylation in the manner described in Example 1(b), giving 8.25 g of the title compound, melting at 116° C.

Nuclear Magnetic Resonance Spectrum (CDCl$_3$) δ ppm; 1.45 (9H, singlet, t-butyl); 2.94 (3H, singlet, CH$_3$SO$_2$); 4.42 (2H, doublet, J=4 Hz, C—CH$_2$—O); 5.0–5.4 (2H, multiplet, —N$\underline{H}$—C$\underline{H}$—thienyl); 6.8–7.25 (3H, multiplet, protons of the thiophene ring).

16(c) Benzhydryl ester of S-[2(S)-t-butoxycarbonylamino-1-(2-thienyl)ethyl]-N-phthaloylcysteine The benzhydryl ester of N-phthaloyl-L-cysteine was manufactured from 11.7 g of L-cysteine p-toluenesulfonate, 8.8 g of N-ethoxycarbonylphthalimide, 7.26 g of sodium bicarbonate and 8.6 g of diphenyldiazomethane in the manner described in Example 1(c), and this was reacted with 11.8 g of 1(S)-t-butoxycarbonylamino-1-(2-thienyl)-2-methanesulfonyloxyethane [prepared as described in step (b) above], giving 13.7 g of the title compound as an amorphous solid.

Nuclear Magnetic Resonance Spectrum (CDCl$_3$) δ ppm: 1.40 (9H, singlet, t-butyl); 2.8–3.4 (4H, multiplet, CH$_2$—S—CH$_2$); 4.8–5.2 (3H, multiplet, NH, N—C$\underline{H}$—CO, N—C$\underline{H}$—thienyl); 6.5–7.2 (3H, multiplet, protons of the thiophene ring); 6.80 (1H, singlet, CO$_2$C$\underline{H}$Ph$_2$); 7.11 and 7.18 (together 10H, each singlet, phenyl protons of benzyhydryl); 7.4–7.8 (4H, multiplet, phthaloyl protons).

16(d) S-[2(S)-Amino-2-(2-thienyl)ethyl]-N-phthaloylcysteine trifluoroacetate 15.6 g of the benzyhydryl ester of S-[2-(S)-t-butoxycarbonylamino-2-(2-thienyl)ethyl]-N-phthaloylcysteine [prepared as described in step (c) above] was reacted with trifluoroacetic acid in the manner described in Example 1(d), to give 12.8 g of the title compound. This product was subjected to the following cyclization reactin in step (e) without purification.

16(e) 5-Oxo-6(R)-phthalimido-3(S)-(2-thienyl)perhydro-1,4-thiazepine 12.8 g of S-[2(S)-amino-2-(2-thienyl)ethyl]-N-phthaloylcysteine trifluoroacetate [prepared as described in step (d) above] were subjected to condensation and cyclization with diphenylphosphoryl azide in the manner described in Example 1(e), to give 2.25 g of the title compound, melting at 254°–255° C.

Nuclear Magnetic Resonance Spectrum (CDCl$_3$) δ ppm: 2.8–3.15 (4H, multiplet, C$\underline{H}_2$—S—C$\underline{H}_2$); 4.8–5.65 (2H, multiplet, N—C$\underline{H}$—CO, N—C$\underline{H}$—thienyl); 6.9–7.6 (3H, multiplet, protons of the thiophene ring); 7.87 (4H, singlet, phthaloyl protons).

16(f) t-Butyl α-[5-oxo-6-(R)-phthalimido-3-(S)-(2-thienyl)perhydro-1,4-thiazepin-4-yl]acetate 1.3 g of 5-oxo-6(R)-phthalimido-3(S)-(2-thienyl)perhydro-1,4-thiazepine [prepared as described in step (e) above] was treated with t-butyl bromoacetate in the manner described in Example 1(f), to give 0.99 g of the title compound as crystals, melting at 211°–212° C.

Nuclear Magnetic Resonance Spectrum (CDCl$_3$) δ ppm: 1.36 (9H, singlet, t-butyl); 2.8–4.2 (6H, multiplet, C$\underline{H}_2$—S—C$\underline{H}_2$, NC$\underline{H}_2$CO); 5.4–5.9 (2H, multiplet, N—C$\underline{H}$—CO, N—C$\underline{H}$—thienyl); 6.9–7.45 (3H, multiplet, protons of the thiophene ring); 7.6–8.0 (4H, multiplet, phthaloyl protons).

16(g) t-Butyl α-[6(R)-amino-5-oxo-3(S)-(2-thienyl)perhydro-1,4-thiazepin-4-yl]acetate 1.18 g of t-butyl α-[5-oxo-6(R)-phthalimido-3(S)-(2-thienyl)perhydro-1,4-thiazepin-4-yl]acetate [prepared as described in step (f) above] was subjected to dephthaloylization with methylhydrazine in the manner described in Example 1(g), to give 0.77 g of the title compound as an amorphous solid.

Nuclear Magnetic Resonance Spectrum (CDCl$_3$) δ ppm: 1.38 (9H, singlet, t-butyl); 2.41 (2H, broad singlet, NH$_2$); 2.7–3.65 (4H, multiplet, C$\underline{H}_2$—S—C$\underline{H}_2$); 3.68 (2H, AB quartet, Δδ=0.48 ppm, J=17 Hz, NC$\underline{H}_2$CO); 4.33 (1H, doublet of doublets, J=6 & 7 Hz, NH$_2$—C$\underline{H}$—CO); 5.44 (1H, doublet of doublets, J=2.5 & 9 Hz, N—C$\underline{H}$—thienyl); 6.93 (2H, multiplet, protons at C$_3$ and C$_4$ of the thiophene ring); 7.26 (1H, multiplet, proton at C$_5$ of the thiophene ring).

16(h) t-Butyl α-{6(R)-[1-ethoxycarbonyl-3-phenylpropylamino]-5-oxo-3(S)-(2-thienyl)perhydro-1,4-thiazepin-4-yl}acetate (compound No. 201)

344 mg of t-butyl α-[6(R)-amino-5-oxo-3(S)-(2-thienyl)perhydro-1,4-thiazepin-4-yl]acetate [prepared as described in step (g) above] were subjected to N-alkylation with 406 mg of ethyl 2-bromo-4-phenylbutyrate in the manner described in Example 1(h). The reaction product was subjected to silica gel column chromatography using a 1:20 by volume mixture of ethyl acetate and methylene chloride as eluent, which separated the compound into two isomers, A and B, (ascribed to the asymmetric carbon atom to which the phenethyl group is attached). Isomer A (in which the carbon attached to the phenethyl group had the R-configuration) was eluted first as an oily compound in a yield of 0.17 g.

Nuclear Magnetic Resonance Spectrum (CDCl$_3$) δ ppm: 1.25 (3H, triplet, J=7.5 Hz, CO$_2$CH$_2$CH$_3$); 1.40 (9H, singlet, t-butyl); 1.7–2.25 (2H, multiplet, PhCH$_2$CH$_2$); 2.5–4.35 (14H, multiplet, PhCH$_2$CH$_2$—CH—NH, protons of the thiazepine ring, N—CH$_2$CO, CO$_2$CH$_2$CH$_3$); 5.43 (1H, doublet of doublets, J=2 & 9 Hz, N—CH—thienyl); 6.9–7.4 (3H, multiplet, protons of the thiophene ring); 7.20 (singlet, phenyl protons).

Isomer B (in which the carbon atom attached to the phenethyl group had the S-configuration) was eluted next. This was an oily compound in a yield of 0.17 g.

Nuclear Magnetic Resonance Spectrum (CDCl$_3$) δ ppm: 1.28 (3H, singlet, J=7.5 Hz, CO$_2$CH$_2$CH$_3$); 1.39 (9H, singlet, t-butyl); 1.8–2.2 (2H, multiplet, PhCH$_2$CH$_2$); 2.55–4.2 (12H, multiplet, PhCH$_2$CH$_2$—CH—NH), protons of the thiazepine ring, N—CH$_2$CO); 4.16 (2H, quartet, J=7.5 Hz, CO$_2$CH$_2$CH$_3$); 5.45 (1H, doublet of doublets, J=2.5 & 10 Hz, N—CH—thienyl); 6.95–7.45 (3H, multiplet, protons of the thiophene ring); 7.20 (5H, singlet, phenyl protons).

EXAMPLE 17

α-{6(R)-[1(S)-ethoxycarbonyl-3-phenylpropylamino]-5-oxo-3(S)-(2-thienyl)perhydro-1,4-thiazepin-4-yl}acetic acid (Compound No. 39)

160 mg of isomer B of t-butyl α-{6(R)-[1-ethoxycarbonyl-3-phenylpropylamino]-5-oxo-3(S)-(2-thienyl)perhydro-1,4-thiazepin-4-yl}acetate [prepared as described in Example 16(h)] were subjected to de-t-butylation with trifluoroacetic acid in the manner described in Example 3, to give 118 mg of the title compound as an amorphous solid.

Nuclear Magnetic Resonance Spectrum [(CD$_3$)$_2$SO] δ ppm: 1.29 (3H, triplet, J=7.5 Hz, CO$_2$CH$_2$CH$_3$); 1.9–2.35 (2H, multiplet, PhCH$_2$CH$_2$); 2.45–4.2 (9H, multiplet, PhCH$_2$CH$_2$—CH—N, CH$_2$—S—CH$_2$, N—CH$_2$CO); 4.26 (2H, quartet, J=7.5 Hz, CO$_2$CH$_2$CH$_3$); 5.03 (1H, broad triplet, J=6 Hz, N—CH—CO); 5.62 (1H, doublet of doublets, J=3 & 11 Hz, N—CH—thienyl); 6.9–7.3 (2H, multiplet, protons at C$_3$ and C$_4$ of the thiophene ring); 7.32 (5H, singlet, phenyl protons); 7.67 (1H, doublet, J=5 Hz, proton at C$_5$ of the thiophene ring).

EXAMPLE 18

α-{6(R)-[1(S)-Carboxy-3-phenylpropylamino]-5-oxo-3(S)-(2-thienyl)perhydro-1,4-thiazepin-4-yl}acetic acid (Compound No. 40)

90 mg of α-{6(R)-[1(S)-ethoxycarbonyl-3-phenylpropylamino]-5-oxo-3(S)-(2-thienyl)perhydro-1,4-thiazepin-4-yl}acetic acid (prepared as described in Example 17 above) were hydrolyzed with aqueous sodium hydroxide in the manner described in Example 5, to give 65 mg of the title compound as a powder.

Nuclear Magnetic Resonance Spectrum [(CD$_3$)$_2$SO] δ ppm: 1.7–2.1 (2H, multiplet, PhCH$_2$CH$_2$); 2.4–3.8 (7H, multiplet, PhCH$_2$CH$_2$—CH—N, CH$_2$—S—CH$_2$); 3.67 (2H, singlet, N—CH$_2$—CO); 4.46 (1H, broad triplet, J=6 Hz, N—CH—CO); 5.58 (1H, doublet of doublets, J=2.5 & 10 Hz, N—CH—thienyl); 6.9–7.2 (2H, multiplet, protons at C$_3$ and C$_4$ of the thiophene ring); 7.27 (5H, singlet, phenyl protons); 7.62 (1H, doublet, J=5 Hz, proton at C$_5$ of the thiophene ring).

EXAMPLE 19 t-Butyl α-{6-[1-butoxycarbonyl-3-phenylpropylamino]-5-oxo-2-phenylperhydro-1,4-thiazepin-4-yl}acetate (Compound No. 202)

0.34 g of t-butyl α-(6-amino-5-oxo-2-phenylperhydro-1,4-thiazepin-4-yl)acetate [prepared as described in Example 7(g) above] was N-alkylated with 0.45 g of butyl 2-bromo-4-phenylbutyrate in the manner described in Example 1(h). The resulting product was subjected to silica gel column chromatography using a 1:40 by volume mixture of ethyl acetate and methylene chloride as the eluent. As a result, the title compound was separated into isomers A and B (resulting from the asymmetric carbon atom to which the phenethyl group is attached).

Isomer A, first eluted: an oily substance, yield 0.13 g.

Nuclear Magnetic Resonance Spectrum (CDCl$_3$) δ ppm: 0.7–1.1 (3H, multiplet, CH$_3$ of n-butyl); 1.46 (9H, singlet, t-butyl); 1.1–2.3 [7H, multiplet, CO$_2$CH$_2$(CH$_2$)$_2$CH$_3$, PhCH$_2$CH$_2$, NH]; 2.3–4.4 [13H, multiplet, PhCH$_2$CH$_2$—CH—N, protons of the thiazepine ring, N—CH$_2$—CO, CO$_2$CH$_2$(CH$_2$)$_2$CH$_3$]; 7.17 (10H, singlet, protons of the 2 phenyl groups).

Isomer B subsequently eluted: an oily substance, yield 0.12 g.

Nuclear Magnetic Resonance Spectrum (CDCl$_3$) δ ppm: 0.7–1.1 (3H, multiplet, CH$_3$ of n-butyl); 1.46 (9H, singlet, t-butyl); 1.1–2.25 [7H, multiplet, CO$_2$CH$_2$(CH$_2$)$_2$CH$_3$, PhCH$_2$CH$_2$, NH]; 2.3–4.4 [13H, multiplet, PhCH$_2$CH$_2$—CH—N, protons of the thiazepine ring, N—CH$_2$CO, CO$_2$CH$_2$(CH$_2$)$_2$CH$_3$]. 7.15 (10H, singlet, protons of the 2 phenyl groups).

EXAMPLE 20

α-{6-[1-Butoxycarbonyl-3-phenylpropylamino]-5-oxo-2-phenylperhydro-1,4-thiazepin-4-yl}acetic acid (Compound No. 188)

0.12 g of isomer B of t-butyl α-[6-(1-butoxycarbonyl-3-phenylpropylamino)-5-oxo-2-phenylperhydro-1,4-thiazepin-4-yl]acetate (prepared as described in Example 19 above) was subjected to de-t-butylation with trifluoroacetic acid in the manner described in Example 3, to give 78 mg of the title compound as an amorphous solid.

Nuclear Magnetic Resonance Spectrum (CDCl$_3$) δ ppm: 0.7–1.1 (3H, multiplet, CH$_3$ of n-butyl); 1.1–1.8 [4H, multiplet, CO$_2$CH$_2$(CH$_2$)$_2$CH$_3$]; 1.95–2.5 (2H, multiplet, PhCH$_2$CH$_2$); 2.5–4.7 [13H, multiplet, PhCH$_2$CH$_2$CH—N, protons of the thiazepine ring, N—CH$_2$—CO, CO$_2$CH$_2$(CH$_2$)$_2$CH$_3$]; 7.18 (10H, singlet, protons of the 2 phenyl groups).

EXAMPLE 21 t-Butyl
α-[6-(1-benzyloxycarbonyl-3-phenylpropylamino)-5-oxo-2-phenylperhydro-1,4-thiazepin-4-yl]acetate
(Compound No. 203)

0.34 g of t-butyl α-(6-amino-5-oxo-2-phenylperhydro-1,4-thiazepin-4-yl)acetate [prepared as described in Example 7(g)] was N-alkylated with 0.50 g of benzyl 2-bromo-4-phenylbutyrate in the same manner as in Example 1(h). The reaction product was subjected to silica gel column chromatography using a 1:40 by volume mixture of ethyl acetate and methylene chloride as eluent, to separate it into two isomers, A and B, (ascribed to the asymmetric carbon atom to which the phenethyl group is attached).

Isomer A was eluted first as an oil in a yield of 0.15 g.

Nuclear Magnetic Resonance Spectrum (CDCl$_3$) δ ppm: 1.46 (9H, singlet t-butyl); 1.8-2.2 (2H, multiplet, PhCH$_2$CH$_2$); 2.4-4.5 (12H, multiplet, PhCH$_2$CH$_2$—CH—NH, protons of the thiazepine ring, N—CH$_2$—CO); 5.09 (2H, AB quartet, Δδ=0.20 ppm, J=13 Hz, CH$_2$Ph); 7.1-7.4 (15H, multiplet, protons of the 3 phenyl groups).

Isomer B was eluted next as an oil in a yield of 0.15 g.

Nuclear Magnetic Resonance Spectrum (CDCl$_3$) δ ppm: 1.46 (9H, singlet, t-butyl); 1.8-2.25 (2H, multiplet, PhCH$_2$CH$_2$); 2.45-4.45 (12H, multiplet, PhCH$_2$CH$_2$—CH—NH, protons of the thiazepine ring, N—CH$_2$—CO); 5.12 (2H, singlet, CH$_2$Ph); 7.16, 7.27, 7.33 (together 15H, each singlet, protons of the 3 phenyl groups).

EXAMPLE 22

α-[6-(1-Benzyloxycarbonyl-3-phenylpropylamino)-5-oxo-2-phenylperhydro-1,4-thiazepin-4-yl]acetic acid
(Compound No. 189)

0.10 g of isomer B of t-butyl α-[6-(1-benzyloxycarbonyl-3-phenylpropylamino)-5-oxo-2-phenylperhydro-1,4-thiazepin-4-yl]acetate (prepared as described in Example 21) was treated with trifluoroacetic acid to remove its t-butyl group by the process described in Example 3. 70 mg of the title compound were obtained as amorphous solid.

Nuclear Magnetic Resonance Spectrum [(CD$_3$)$_2$SO] δ ppm: 1.95-2.3 (2H, multiplet, PhCH$_2$CH$_2$); 2.4-5.0 (11H, multiplet, PhCH$_2$CH$_2$—CH—N, protons of the thiazepine ring); 5.28 (2H, AB quartet, Δδ=2.0 ppm, J=13 Hz, CH$_2$Ph); 7.1-7.35 (5H, multiplet, CH$_2$Ph); 7.4, 7.47 (together 10H, each singlet, protons of the 2 phenyl groups).

EXAMPLE 23 t-Butyl
α-[6(R)-(1-butoxycarbonyl-3-phenylpropylamino)-5-oxo-3(S)-(2-thienyl)perhydro-1,4-thiazepin-4-yl]acetate
(Compound No. 204)

345 mg of t-butyl α-[6(R)-amino-5-oxo-3(S)-(2-thienyl)perhydro-1,4-thiazepin-4-yl]acetate [prepared as described in Example 16(g)] were N-alkylated with 450 mg of butyl 2-bromo-4-phenylbutyrate in the same manner as in Example 1(h). The reaction product was then subjected to silica gel column chromatography using a 1:40 by volume mixture of ethyl acetate and methylene chloride as eluent, to separate it into two isomers, A and B (ascribed to the asymmetric carbon atom to which the phenethyl group is attached).

Isomer A (in which the carbon atom attached to the phenethyl group had the R-configuration) was eluted first as an oily substance in a yield of 78 mg.

Nuclear Magnetic Resonance Spectrum (CDCl$_3$) δ ppm: 0.7-1.1 (3H, multiplet, CH$_3$ of n-butyl); 1.1-2.25 (6H, multiplet, CO$_2$CH$_2$(CH$_2$)$_2$CH$_3$, PhCH$_2$CH$_2$); 1.40 (9H, singlet, t-butyl); 2.5-4.3 [14H, multiplet, PhCH$_2$CH$_2$—CH—NH, protons of the thiazepine ring, N—CH$_2$—CO, CO$_2$CH$_2$(CH$_2$)$_2$CH$_3$]; 5.44 (1H, doublet of doublets, J=2.5 & 9.5 Hz, N—CH—thienyl); 6.9-7.4 (3H, multiplet, the thiophene ring protons); 7.20 (5H, singlet, phenyl protons).

Isomer B (in which the carbon atom attached to the phenethyl group had the S configuration) was eluted next as an oily substance in a yield of 100 mg.

Nuclear Magnetic Resonance Spectrum (CDCl$_3$) δ ppm: 0.8-1.1 (3H, multiplet, CH$_3$ of n-butyl); 1.15-2.2 [6H, multiplet, CO$_2$CH$_2$(CH$_2$)$_2$CH$_3$, PhCH$_2$CH$_2$]; 1.41 (9H, singlet t-butyl); 2.5-4.3 [14H, multiplet, PhCH$_2$CH$_2$—CH—NH, protons of the thiazepine ring, N—CH$_2$—CO, CO$_2$CH$_2$(CH$_2$)$_2$CH$_3$]; 5.43 (1H, broad doublet, J=9 Hz, N—CH—thienyl); 6.9-7.4 (3H, multiplet, the thiophene ring protons); 7.20 (5H, singlet, phenyl protons).

EXAMPLE 24

α-{6(R)-[1(S)-Butoxycarbonyl-3-phenylpropylamino]-5-oxo-3(S)-(2-thienyl)perhydro-1,4-thiazepin-4-yl}acetic acid (Compound No. 190)

100 mg of isomer B of t-butyl α-[6(R)-(1-butoxycarbonyl-3-phenylpropylamino)-5-oxo-3(S)-(2-thienyl)perhydro-1,4-thiazepin-4-yl]acetate (prepared as described in Example 23) was treated with trifluoroacetic acid to remove its t-butyl group in the same manner as in Example 3. 60 mg of the title compound were obtained as an amorphous solid.

Nuclear Magnetic Resonance Spectrum [(CD$_3$)$_2$SO] δ ppm: 0.90 (3H, broad triplet, J=7 Hz, CH$_3$ of n-butyl); 1.1-1.8 [4H, multiplet, CO$_2$CH$_2$(CH$_2$)$_2$CH$_3$]; 2.0-2.3 (2H, multiplet, PhCH$_2$CH$_2$); 2.5-4.3 [11H, multiplet, PhCH$_2$CH$_2$—CH—N, CH$_2$SCH$_2$, N—CH$_2$—CO, CO$_2$CH$_2$(CH$_2$)$_2$CH$_3$]; 5.03 (1H, broad triplet, J=5 Hz, N—CH—CO); 5.62 (1H, doublet of doublets, J=3 & 10 Hz, N—CH—thienyl); 6.95-7.3 (2H, multiplet, protons at the C3 and C4 positions of the thiophene ring); 7.30 (5H, singlet, phenyl protons); 7.67 (1H, doublet, J=5 Hz, proton at the 5-position of the thiophene ring).

EXAMPLE 25 t-Butyl
α-[6(R)-(1-benzyloxycarbonyl-3-phenylpropylamino)-5-oxo-3(S)-(2-thienyl)perhydro-1,4-thiazepin-4-yl]acetate (Compound No. 205)

282 mg of t-butyl α-[6(R)-amino-5-oxo-3(S)-(2-thienyl)perhydro-1,4-thiazepin-4-yl]acetate [prepared as described in Example 16(g)] were N-alkylated with 684 mg of benzyl 2-bromo-4-phenylbutyrate in the same manner as in Example 1(h). The reaction product was subjected to silica gel column chromatography using a 1:4 by volume mixture of ethyl acetate and cyclohexane, to separate it into two isomers, A and B (ascribed to the asymmetric carbon atom to which the phenethyl group is attached).

Isomer A (in which the carbon atom attached to the phenethyl group had the R-configuration) was eluted first as an oily substance in a yield of 128 mg.

Nuclear Magnetic Resonance Spectrum (CDCl$_3$) δ ppm: 1.41 (9H, singlet, t-butyl); 1.75–2.2 (2H, multiplet, PhCH$_2$CH$_2$); 2.5–4.3 (9H, multiplet, PhCH$_2$CH$_2$—CH—NH, CH$_2$SCH$_2$, N—CH—CO); 3.68 (2H, AB quartet, Δδ=0.72 ppm, J=17 Hz, N—CH$_2$—CO); 5.12 (2H, singlet, CH$_2$Ph); 5.35 (1H, doublet of doublets, J=1.5 & 9 Hz, N—CH—thienyl); 6.8–7.35 (3H, multiplet, the thiophene ring protons); 7.16, 7.32 (together 10H, each singlet, protons of the 2 phenyl groups).

Isomer B (in which the carbon atom attached to the phenethyl group had the S-configuration) was eluted next as an oily substance in a yield of 158 mg.

Nuclear Magnetic Resonance Spectrum (CDCl$_3$) δ ppm: 1.38 (5H, singlet, t-butyl); 1.8–2.3 (2H, multiplet, PhCH$_2$CH$_2$); 2.4–4.25 (11H, multiplet, PhCH$_2$CH$_2$—CH—NH, CH$_2$SCH$_2$, N—CH—CO, N—CH$_2$—CO); 5.14 (2H, singlet, CH$_2$Ph); 5.34 (1H, doublet of doublets, J=2.5 & 10 Hz, N—CH—thienyl); 6.9–7.4 (3H, multiplet, the thiophene ring protons); 7.16, 7.33 (together 10H, each singlet, protons of the 2 phenyl groups).

EXAMPLE 26

α-{6(R)-[1(S)-Benzyloxycarbonyl-3-phenyl-propylamino]-5-oxo-3(S)-(2-thienyl)perhydro-1,4-thiazepin-4-yl}acetic acid (Compound No. 191)

158 mg of isomer B of t-butyl α-[6(R)-(1-benzyloxycarbonyl-3-phenylpropylamino)-5-oxo-3(S)-(2-thienyl)perhydro-1,4-thiazepin-4-yl]acetate (prepared as described in Example 25) were treated with trifluoroacetic acid to remove its t-butyl group in the same manner as described in Example 3. The title compound was obtained as an amorphous solid in a yield of 109 mg.

Nuclear Magnetic Resonance Spectrum (CDCl$_3$) δ ppm: 1.8–2.3 (2H, multiplet, PhCH$_2$CH$_2$); 2.44–4.8 (10H, multiplet, PhCH$_2$CH$_2$—CH—N, CH$_2$SCH$_2$, N—CH$_2$—CO, N—CH—CO); 5.15 (2H, singlet, CH$_2$Ph); 5.30 (1H, broad doublet, J=10 Hz, N—CH—thienyl); 6.8–7.4 (3H, multiplet, the thiophene ring protons); 7.13, 7.32, (together 10H, each singlet, protons of the 2 phenyl groups).

EXAMPLE 27 t-Butyl α-[6(R)-(1-ethoxycarbonyl-3-phenylpropylamino)-3(R)-isopropyl-5-oxoperhydro-1,4-thiazepin-4-yl]acetate (Compound No. 206)

The procedure described in steps (a) to (h) of Example 1 was repeated, except that D-2-amino-3-methyl-1-butanol was used as the starting material. Two isomers (derived from the asymmetric carbon atom to which the phenethyl group is attached), that is t-butyl α-{6(R)-[1(R)-ethoxycarbonyl-3-phenylpropylamino]-3(R)-isopropyl-5-oxoperhydro-1,4-thiazepin-4-yl}acetate (isomer A) and t-butyl α-{6(R)-[1(S)-ethoxycarbonyl-3-phenylpropylamino]-3(R)-isopropyl-5-oxoperhydro-1,4-thiazepin-4-yl}acetate (isomer B), were obtained as oils.

Isomer A

Nuclear Magnetic Resonance Spectrum (CDCl$_3$) δ ppm: 0.98 [6H, doublet of doublets, J=3 & 6.5 Hz, CH(CH$_3$)$_2$]; 1.22 (3H, triplet, J=7 Hz, CO$_2$CH$_2$CH$_3$); 1.47 (9H, singlet, t-butyl); 1.6–2.2 (2H, multiplet, PhCH$_2$CH$_2$); 2.4–4.4 [15H, multiplet, PhCH$_2$CH$_2$CHCO—NH, protons of the thiazepine ring, CH(CH$_3$)$_2$, N—CH$_2$—CO, CO$_2$CH$_2$CH$_3$]; 7.19 (5H, singlet, phenyl protons).

Isomer B

Nuclear Magnetic Resonance Spectrum (CDCl$_3$) δ ppm: 1.00 [6H, doublet, J=6.5 Hz, CH(CH$_3$)$_2$]; 1.23 (3H, triplet, J=7 Hz, CO$_2$CH$_2$CH$_3$); 1.47 (9H, singlet, t-butyl); 1.7–2.2 (2H, multiplet, PhCH$_2$CH$_2$); 2.4–4.2 [13H, multiplet, PhCH$_2$CH$_2$CHCO—NH, protons of the thiazepine ring, CH(CH$_3$)$_2$, N—CH$_2$—CO] 4.12 (2H, quartet, J=7.5 Hz, CO$_2$CH$_2$CH$_3$); 1.19 (5H, singlet, phenyl protons).

EXAMPLE 28

α-{6(R)-[1(S)-Ethoxycarbonyl-3-phenylpropylamino]-3(R)-isopropyl-5-oxoperhydro-1,4-thiazepin-4-yl}acetic acid (Compound No. 173)

0.32 g of t-butyl α-{6(R)-[1(S)-ethoxycarbonyl-3-phenylpropylamino]-3(R)-isopropyl-5-oxoperhydro-1,4-thiazepin-4-yl}acetate (isomer B) synthesized as described in Example 27 was subjected to de-t-butylation with trifluoroacetic acid in the same manner as described in Example 3, to give 260 mg of the title compound as an amorphous solid.

Nuclear Magnetic Resonance Spectrum (CDCl$_3$) δ ppm: 0.98 [6H, broad doublet, J=4 Hz, CH(CH$_3$)$_2$]; 1.24 (3H, triplet, J=7 Hz, CO$_2$CH$_2$CH$_3$); 1.7–2.3 (2H, multiplet, PhCH$_2$CH$_2$); 2.4–4.8 [12H, · multiplet, PhCH$_2$CH$_2$CHCO—NH, protons of the thiazepine ring, CH(CH$_3$)$_2$, N—CH$_2$—CO]; 4.15 (2H, quartet, J=7 Hz, CO$_2$CH$_2$CH$_3$); 7.12 (5H, singlet, phenyl protons).

EXAMPLE 29

α-{6(R)-[1(S)-Carboxy-3-phenylpropylamino]-3(R)-isopropyl-5-oxoperhydro-1,4-thiazepin-4-yl}acetic acid (Compound No. 174)

160 mg of α-{6(R)-[1(S)-ethoxycarbonyl-3-phenylpropylamino]-3(R)-isopropyl-5-oxoperhydro-1,4-thiazepin-4-yl}acetic acid (prepared as described in Example 28 above) were hydrolyzed with aqueous sodium hydroxide in the same manner as described in Example 5, giving 113 mg of the title compound as a powder.

Nuclear Magnetic Resonance Spectrum [(CD$_3$)$_2$SO] δ ppm: 0.97 [6H, doublet, J=6 Hz, CH(CH$_3$)$_2$]; 1.7–2.2 (2H, multiplet, PhCH$_2$CH$_2$); 2.3–4.4 [10H, multiplet, PhCH$_2$CH$_2$CHCO—NH, protons of the thiazepine ring, CH(CH$_3$)$_2$]; 3.83 (2H, singlet, N—CH$_2$—CO); 7.25 (5H, singlet, phenyl protons).

EXAMPLE 30 t-Butyl α-[6(R)-(1-ethoxycarbonyl-3-phenylpropylamino)-3(R)-methyl-5-oxoperhydro-1,4-thiazepin-4-yl]acetate (Compound No. 207)

The procedure described in steps (a) to (h) of Example 1 was repeated, except that D-2-amino-1-propanol was used as the starting material. Two isomers (derived from the asymmetric carbon atom to which the phenethyl group is attached), that is t-butyl α-{6(R)-[1(R)-ethoxycarbonyl-3-phenylpropylamino]-3(R)-methyl-5-oxoperhydro-1,4-thiazepin-4-yl}acetate (isomer A) and t-butyl α-{6(R)-[1(S)-ethoxycarbonyl-3-phenylpropylamino]-3(R)-methyl-5-oxoperhydro-1,4-thiazepin-4-yl}acetate (isomer B) were obtained as oils.

Isomer A Nuclear Magnetic Resonance Spectrum (CDCl$_3$) δ ppm: 1.22 (3H, triplet, J=7 Hz, CO$_2$CH$_2$CH$_3$); 1.29 (3H, doublet, J=6 Hz, 3—CH$_3$); 1.46 (9H, singlet, t-butyl); 1.7-2.2 (2H, multiplet, PhCH$_2$CH$_2$); 2.3-4.2 (10H, multiplet, PhCH$_2$CH$_2$CHCO—NH, protons of the thiazepine ring); 3.97 (2H, singlet, N—CH$_2$—CO); 4.11 (2H, quartet, J=7 Hz, CO$_2$CH$_2$CH$_3$); 7.19 (5H, singlet, phenyl protons).

Isomer B Nuclear Magnetic Resonance Spectrum (CDCl$_3$) δ ppm: 1.26 (3H, triplet, J=7 Hz, CO$_2$CH$_2$CH$_3$); 1.32 (3H, doublet, J=6 Hz, 3—CH$_3$); 1.7-2.3 (2H, multiplet, PhCH$_2$CH$_2$); 2.35-4.35 (10H, multiplet, PhCH$_2$CH$_2$CHCO—NH, protons of the thiazepine ring); 3.98 (2H, AB quartet, Δδ=0.33 ppm, J=17 Hz, N—CH$_2$—CO); 4.13 (2H, quartet, J=7 Hz, CO$_2$CH$_2$CH$_3$); 7.18 (5H, singlet, phenyl protons).

EXAMPLE 31

α-{6(R)-[1(S)-Ethoxycarbonyl-3-phenylpropylamino]-3(R)-methyl-5-oxoperhydro-1,4-thiazepin-4-yl}acetic acid (Compound No. 171)

0.41 g of t-butyl α-{6(R)-[1(S)-ethoxycarbonyl-3-phenylpropylamino]-3(R)-methyl-5-oxoperhydro-1,4-thiazepin-4-yl}acetate (isomer B) synthesized as described in Example 30 was subjected to de-t-butylation with trifluoroacetic acid in the same manner as described in Example 3, to give 334 mg of the title compound as an amorphous solid.

Nuclear Magnetic Resonance Spectrum (CDCl$_3$) δ ppm: 1.26 (3H, triplet, J=7 Hz, CO$_2$CH$_2$CH$_3$); 1.32 (3H, doublet, J=6 Hz, 3—CH$_3$); 1.8-5.0 (15H, multiplet, PhCH$_2$CH$_2$CHCO—NH, protons of the thiazepine ring, N—CH$_2$—CO, CO$_2$CH$_2$CH$_3$); 7.12 (5H, singlet, phenyl protons).

EXAMPLE 32

α-{6(R)-[1(S)-Carboxy-3-phenylpropylamino]-3(R)-methyl-5-oxoperhydro-1,4-thiazepin-4-yl}acetic acid (Compound No. 172)

175 mg of α-{6(R)-[1(S)-ethoxycarbonyl-3-phenylpropylamino]-3(R)-methyl-5-oxoperhydro-1,4-thiazepin-4-yl}acetic acid (prepared as described in Example 31 above) was hydrolyzed with aqueous sodium hydroxide in the same manner as described in Example 5, to give 93 mg of the title compound as a powder.

Nuclear Magnetic Resonance Spectrum [(CD$_3$)$_2$SO] δ ppm: 1.28 (3H, doublet, J=6.5 Hz, 3—CH$_3$); 1.7-2.1 (2H, multiplet, PhCH$_2$CH$_2$); 2.3-4.35 (9H, multiplet, PhCH$_2$CH$_2$CHCO—NH, protons of the thiazepine ring); 3.98 (2H, AB quartet, Δδ=0.28 ppm, J=17 Hz, N—CH$_2$—CO); 7.26 (5H, singlet, phenyl protons).

EXAMPLE 33 t-Butyl α-[3(S)-benzyl-6(R)-(1-ethoxycarbonyl-3-phenylpropylamino)-5-oxoperhydro-1,4-thiazepin-4-yl]acetate (Compound No. 208)

The procedure described in steps (a) to (h) of Example 1 was repeated, except that L-2-amino-3-phenyl-1-propanol was used as the starting material. Two isomers (derived from the asymmetric carbon atom to which the phenethyl group is attached), that is t-butyl α-{3(S)-benzyl-6(R)-[1(R)-ethoxycarbonyl-3-phenylpropylamino]-5-oxoperhydro-1,4-thiazepin-4-yl}acetate (isomer A) and t-butyl α-{3(S)-benzyl-6(R)-[1(S)-ethoxycarbonyl-3-phenylpropylamino]-5-oxoperhydro-1,4-thiazepin-4-yl}acetate (isomer B) were obtained as oils.

Isomer A

Nuclear Magnetic Resonance Spectrum (CDCl$_3$) δ ppm: 1.24 (3H, triplet, J=7 Hz, CO$_2$CH$_2$CH$_3$); 1.43 (9H, singlet, t-butyl); 1.7-2.2 (2H, multiplet, PhCH$_2$CH$_2$); 2.3-4.4 (14H, multiplet, pHCH$_2$CH$_2$CHCO—NH, protons of the thiazepine ring, 3—CH$_2$Ph, N—CH$_2$—CO); 4.14 (2H, quartet, J=7 Hz, CO$_2$CH$_2$CH$_3$); 7.19 (10H, singlet, protons of two phenyl groups).

Isomer B

Nuclear Magnetic Resonance Spectrum (CDCl$_3$) δ ppm: 1.27 (3H, triplet, J=7 Hz, CO$_2$CH$_2$CH$_3$); 1.47 (9H, singlet, t-butyl); 1.8-2.2 (2H, multiplet, PhCH$_2$CH$_2$); 2.4-4.4 (14H, multiplet, PhCH$_2$CH$_2$CHCO—NH, protons of the thiazepine ring, 3—CH$_2$Ph, N—CH$_2$—CO); 4.16 (2H, quartet, J=7 Hz, CO$_2$CH$_2$CH$_3$); 7.20 (10H, singlet, protons of two phenyl groups).

EXAMPLE 34

α-{3(S)-Benzyl-6(R)-[1(S)-ethoxycarbonyl-3-phenylpropylamino]-5-oxoperhydro-1,4-thiazepin-4-yl}acetic acid (Compound No. 17)

630 mg of t-butyl α-{3(S)-benzyl-6(R)-[1(S)-ethoxycarbonyl-3-phenylpropylamino]-5-oxoperhydro-1,4-thiazepin-4-yl}acetate (isomer B) synthesized as described in Example 33 was subjected to de-t-butylation with trifluoroacetic acid in the same manner as described in Example 3, to give 438 mg of the title compound as an amorphous solid.

Nuclear Magnetic Resonance Spectrum (CDCl$_3$) δ ppm: 1.23 (3H, triplet, J=7 Hz, CO$_2$CH$_2$CH$_3$); 1.7-2.3 (2H, multiplet, PhCH$_2$CH$_2$); 2.4-4.6 (13H, multiplet, PhCH$_2$CH$_2$CHCO—NH, protons of the thiazepine ring, 3—CH$_2$Ph, N—CH$_2$—CO); 4.14 (2H, quartet, J=7 Hz, CO$_2$CH$_2$CH$_3$); 7.18 (10H, singlet, protons of two phenyl groups).

EXAMPLE 35

α-{3(S)-Benzyl-6(R)-[1(S)-carboxy-3-phenylpropylamino]-5-oxoperhydro-1,4-thiazepin-4-yl}acetic acid (Compound No. 18)

326 mg of α-{3(S)-benzyl-6(R)-[1(S)-ethoxycarbonyl-3-phenylpropylamino]-5-oxoperhydro-1,4-thiazepin-4-yl}acetic acid were hydrolyzed with aqueous sodium hydroxide in the same manner as described in Example 5, to give 225 mg of the title compound as a powder.

Nuclear Magnetic Resonance Spectrum [(CD$_3$)$_2$SO] δ ppm: 1.6-2.2 (2H, multiplet, PhCH$_2$CH$_2$); 2.4-4.5 (13H, multiplet, PhCH$_2$CH$_2$CHCO—NH, protons of the thiazepine ring, 3—CH$_2$Ph, N—CH$_2$—CO); 7.22 (10H, singlet, protons of two phenyl groups).

EXAMPLE 36 t-Butyl α-[6-(1-ethoxycarbonyl-3-phenylpropylamino)-2-(1-naphthyl)-5-oxoperhydro-1,4-thiazepin-4-yl]acetate (Compound No. 163)

36(a) 2-t-Butoxycarbonylamino-1-(1-naphthyl)ethanol

Crude 2-amino-1-(1-naphthyl)ethanol (obtained by the reduction of 44 g of 1-naphthaldehyde cyanohydrin with lithium aluminum hydride) was stirred with 12.8 g of triethylamine and 20 g of di-t-butyl pyrocarbonate in 200 ml of methanol for 1 hour at room temperature.

The reaction mixture was then concentrated by evaporation under reduced pressure, and the residue was dissolved in a mixture of ethyl acetate and water. The ethyl acetate layer was separated, washed with water and dried over anhydrous magnesium sulfate, and the solvent was distilled off. The crystalline residue was collected by filtration using diisopropyl ether to give 14.2 g of the title compound melting at 109°–110° C.

Nuclear Magnetic Resonance Spectrum (CDCl$_3$) δ ppm: 1.44 (9H, singlet, t-butyl); 3.05–3.9 (3H, multiplet, —CH$_2$, OH); 5.08 (1H, broad, NH); 5.60 (1H, doublet of triplets, J=4 & 8 Hz, —CH—OH); 7.25–8.25 (7H, multiplet, naphthyl protons).

36(b) 2-t-Butoxycarbonylamino-1-chloro-(1-naphthyl)ethane

To a solution of 13 g of 2-t-butoxycarbonylamino-1-(1-naphthyl)ethanol [prepared as described in step (a) above] in 200 ml of anhydrous methylene chloride was added at 0°–5° C. a solution of 9.4 g of phosphorus pentachloride in 190 ml of anhydrous methylene chloride. The reaction mixture was then stirred for 5 minutes, after which 195 ml of 4N aqueous sodium hydroxide was added all at once to the reaction mixture and the mixture was stirred for 30 minutes whilst ice-cooling. The methylene chloride layer was separated, washed with a large amount of water and dried over anhydrous magnesium sulfate; the solvent was then evaporated off. The residue was subjected to silica gel column chromatography eluted with a 1:7 by volume mixture of ethyl acetate and cyclohexane, to give 9.0 g of the title compound as a syrup.

Nuclear Magnetic Resonance Spectrum (CDCl$_3$) δ ppm: 1.43 (9H, singlet, t-butyl); 3.3–4.2 (2H, multiplet, CH$_2$); 5.00 (1H, broad triplet, NH); 5.83 (1H, doublet of doublets, J=5.5 & 8 Hz, —CH—naphthyl); 7.2–8.3 (7H, multiplet, naphthyl protons).

36(c) Benzhydryl ester of S-[2-t-butoxycarbonylamino-1-(1-naphthyl)ethyl]-N-phthaloylcysteine To a solution of 10 g of L-cysteine p-toluenesulfonate and 7.5 g of N-ethoxycarbonylphthalimide in 68 ml of dimethylformamide were added 6.2 g of sodium bicarbonate under a nitrogen atmosphere. The reaction mixture was then stirred at 90°–100° C. for 3.5 hours, after which it was cooled. The reaction mixture was then poured into a mixture of ethyl acetate and an aqueous solution of potassium hydrogen sulfate, to acidify it. The ethyl acetate layer was separated, washed with an aqueous solution of sodium chloride and dried over anhydrous magnesium sulfate.

To the resulting solution was added 7.4 g of diphenyldiazomethane, and the reaction mixture was stirred for 1 hour under a nitrogen atmosphere. The solvent was then evaporated off and the residue was dissolved in 60 ml of dimethylformamide. To this solution was added 9.6 g of 2-t-butoxycarbonylamino-1-chloro-1-(1-naphthyl)ethane, and the reaction mixture was stirred at 70° C. for 16 hours under a stream of nitrogen. The reaction mixture was then dissolved in a mixture of ethyl acetate and water. The ethyl acetate layer was separated, washed with an aqueous solution of sodium chloride and dried over anhydrous magnesium sulfate, and the solvent was evaporated off. The residue was subjected to silica gel column chromatography using a 1:4 by volume mixture of ethyl acetate and cyclohexane as eluent, to give the title compound as an amorphous solid in a yield of 10.4 g.

Nuclear Magnetic Resonance Spectrum (CDCl$_3$) δ ppm: 1.35 (9H, singlet, t-butyl); 3.15–3.8 (4H, multiplet, CH$_2$—S, C—CH$_2$—N); 4.5–5.1 (3H, multiplet, NH, N—CH—CO, S—CH—naphthyl); 6.61 and 6.70 (together 1H, two kinds of singlet, CHPh$_2$); 6.75–8.3 [21H, multiplet, CH(C$_6$H$_5$)$_2$, naphthyl protons, phthaloyl protons].

36(d) S-[2-Amino-1-(1-naphthyl)ethyl]-N-phthaloylcysteine

To a solution of 10.4 g of the benzyhydryl ester of S-[2-t-butoxycarbonylamino-1-(1-naphthyl)ethyl]-N-phthaloylcysteine in 40 ml of anisole were added 50 ml of trifluoroacetic acid, and the reaction mixture was stirred for 2 hours at room temperature. The solvent was evaporated off, and 40 ml of ethyl acetate, 30 ml of water and 2.0 g of sodium bicarbonate were added to the residue, with stirring. The pH of the reaction mixture was adjusted to a value of 5.8 with 3N hydrochloric acid. Whilst ice-cooling, the reaction mixture was stirred and the precipitate of the title compound was collected by filtration and washed with a 1:1 by volume mixture of acetone and diethyl ether, to yield 5.6 g of the title compound melting at 195°–199° C.

36(e) 2-(1-Naphthyl)-5-oxo-6-phthalimidoperhydro-1,4-thiazepine

To a solution of 5.5 g of S-[2-amino-1-(1-naphthyl)ethyl]-N-phthaloylcysteine in 110 ml of dimethylformamide were added 5.1 g of diphenylphosphoryl azide and 2.6 ml of N-methylmorpholine, and the mixture was stirred for 15 hours at room temperature. Water (about 200 ml) and ethyl acetate (about 500 ml) were added to the reaction mixture, with stirring. The precipitate of the title compound was collected by filtration and washed with water and ethyl acetate, to yield 3.5 g of the title compound melting above 300° C.

Nuclear Magnetic Resonance Spectrum [(CD$_3$)$_2$SO] δ ppm: 2.7–4.6 (4H, multiplet, CH$_2$—S, N—CH$_2$—C); 4.94 (1H, broad doublet, J=8 Hz, S—CH—naphthyl); 5.47 (1H, doublet of doublets, J=3 & 8 Hz, N—CH—CO); 7.4–8.5 (11H, naphthyl protons, phthaloyl protons).

36(f) t-Butyl α-[2(1-naphthyl)-5-oxo-6-phthalimidoperhydro-1,4-thiazepin-4-yl]acetate To a suspension of 3.4 g of 2-(1-naphthyl)-5-oxo-6-phthalimidoperhydro-1,4-thiazepine [prepared as described in step (e) above] in a mixture of 34 ml of dimethylformamide and 10 ml of hexamethylphosphoric triamide were added dropwise 2.25 ml of t-butyl bromoacetate and then, bit by bit, 609 mg of a 55% w/w suspension of sodium hydride in oil at 0°–5° C., under a nitrogen stream. After this addition, the reaction mixture was stirred for 16 hours at room temperature. Ethyl acetate and water were then added to the reaction mixture. The ethyl acetate layer was separated, washed with water and dried over anhydrous magnesium sulfate, and the solvnet was distilled off. The residue was subjected to silica gel column chromatography using a 2:1 by volume mixture of cyclohexane and ethyl acetate as eluent, to give 2.6 g of the title compound as crystals, melting at 211°–213° C.

Nuclear Magnetic Resonance Spectrum (CDCl$_3$) δ ppm: 1.47 (9H, singlet, t-butyl); 3.0–4.9 (6H, multiplet, —CH$_2$—S, N—CH$_2$—CO, —CH$_2$—N); 5.30 (1H, doublet, J=9 Hz, N—CH—CO); 5.78 (1H, broad doublet, J=10 Hz, S—CH—naphthyl); 7.3–8.35 (11H, naphthyl protons, phthaloyl protons).

36(g) t-Butyl α-[6-amino-2-(1-naphthyl)-5-oxoperhydro-1,4-thiazepin-4-yl]acetate To a solution of 2.5 g of t-butyl[2-(1-naphthyl)-5-oxo-6-phthalimidoperhydro-1,4-thiazepin-4-yl]acetate [prepared as described in step (f) above] in a mixture of 20 ml of methylene chloride and 2 ml of methanol was added 0.77 ml of methylhydrazine, and the reaction mixture was allowed to stand for 2 days at room temperature. The reaction mixture was then concentrated by evaporation under reduced pressure, 15 ml of methylene chloride were added to the residue and the mixture was stirred. The resulting precipitate was filtered off and the filtrate was concentrated by evaporation under reduced pressure. The residue was subjected to silica gel column chromatography using a 1:20 by volume mixture of methanol and ethyl acetate as eluent, to give 1.92 g of the title compound as an amorphous solid.

Nuclear Magnetic Resonance Spectrum (CDCl$_3$) δ ppm: 1.47 (9H, singlet, t-butyl); 2.11 (2H, broad singlet, NH$_2$); 2.45–4.8 (7H, multiplet, N—CH$_2$—CO, H$_2$N—CH—CH$_2$S, N—CH$_2$—C); 5.15 (1H, doublet, J=9.5 Hz, S—CH—naphthyl); 7.2–8.3 (7H, multiplet, naphthyl protons).

36(h) t-Butyl α-[6-(1-ethoxycarbonyl-3-phenylpropylamino)-2-(1-naphthyl)-5-oxoperhydro-1,4-thiazepin-4-yl]acetate (Compound No. 163)

To a solution of a mixture of 803 g of t-butyl α-[6-amino-2-(1-naphthyl)-5-oxoperhydro-1,4-thiazepin-4-yl]acetate [prepared as described in step (g) above] and 1.13 g of ethyl 3-bromo-4-phenylbutyrate in 10 ml of dimethylformamide was added 0.66 g of sodium carbonate. The reaction mixture was stirred at 80° C. for 15 hours and then dissolved in a mixture of ethyl acetate and an aqueous solution of sodium chloride. The ethyl acetate layer was separated, washed with water and dried over anhydrous magnesium sulfate, and the solvent was then evaporated off. The residue was subjected to silica gel column chromatography using a 1:30 by volume mixture of ethyl acetate and methylene chloride as eluent, which separated the product into two isomers, A and B, (ascribed to the asymmetric carbon atom to which the phenethyl group is attached).

Isomer A was eluted first: an oily substance in a yield of 0.49 g

Nuclear Magnetic Resonance Spectrum (CDCl$_3$) δ ppm: 1.24 (3H, triplet, J=7.5 Hz, CO$_2$CH$_2$CH$_3$); 1.46 (9H, singlet, t-butyl); 1.7–2.2 (2H, multiplet, PhCH$_2$CH$_2$); 2.4–4.7 (13H, multiplet, PhCH$_2$CH$_2$CH—NH, CO—CH—CH$_2$S—CH—CH$_2$, N—CH$_2$—CO, CO$_2$CH$_2$CH$_3$); 5.13 (1H, broad doublet, J=9 Hz, S—CH—naphthyl); 7.14 (5H, singlet, phenyl protons); 7.2–8.2 (7H, multiplet, naphthyl protons).

Isomer B was eluted next: an oily substance in a yield of 0.46 g.

Nuclear Magnetic Resonance Spectrum (CDCl$_3$) δ ppm: 1.28 (3H, triplet, J=7.5 Hz, CO$_2$CH$_2$CH$_3$); 1.48 (9H, singlet, t-butyl); 1.8–2.3 (2H, multiplet, PhCH$_2$CH$_2$); 2.5–4.8 (13H, multiplet, PhCH$_2$CH$_2$CH—NH, CO—CH—CH$_2$S—CH—CH$_2$, N—CH$_2$—CO, CO$_2$CH$_2$CH$_3$); 5.18 (1H, doublet, J=9.5 Hz, S—CH-naphthyl); 7.21 (5H, singlet, phenyl protons); 7.35–8.3 (7H, multiplet, naphthyl protons).

EXAMPLE 37

α-[6-(1-Ethoxycarbonyl-3-phenylpropylamino)-2-(1-naphthyl)-5-oxoperhydro-1,4-thiazepin-4-yl]acetic acid (Compound No. 134)

455 mg of isomer B of t-butyl α-[6-(1-ethoxycarbonyl-3-phenylpropylamino)-2-(1-naphthyl)-5-oxoperhydro-1,4-thiazepin-4-yl]acetate [prepared as described in Example 36(h)] were dissolved in a mixture of 2 ml of anisole and 2 ml of trifluoroacetic acid. The reaction mixture was then stirred for 4 hours at room temperature, after which it was concentrated by evaporation under reduced pressure. Diisopropyl ether was added to the residue, whilst stirring, and the resulting crystalline powder was collected by filtration, a yield of 447 mg.

This powder was dissolved in a mixture of 2 ml of ethyl acetate and 2 ml of water. 0.2 g of sodium bicarbonate was added to the resulting solution. The reaction mixture was adjusted to a pH value of 2.5 by adding 3N hydrochloric acid. The precipitate of the title compound was collected by filtration to yield 216 mg. The ethyl acetate layer was separated and the aqueous layer was extracted with ethyl acetate. These resulting ethyl acetate solutions were combined and dried over anhydrous magnesium sulfate, and the solvent was then evaporated off to give the title compound as crystals. These crystals (a further 70 mg) were collected by filtration using diisopropyl ether. The crystalline compound melted at 201°–203° C.

Nuclear Magnetic Resonance Spectrum [(CD$_3$)$_2$SO] δ ppm: 1.28 (3H, triplet, J=7.5 Hz, CO$_2$CH$_2$CH$_3$); 2.0–2.4 (2H, multiplet, PhCH$_2$CH$_2$); 2.5–5.4 (13H, multiplet, PhCH$_2$CH$_2$CH—N, protons of the thiazepine ring, N—CH$_2$—CO, CO$_2$CH$_2$CH$_3$); 7.32 (5H, singlet, phenyl protons); 7.2–8.3 (7H, multiplet, naphthyl protons).

EXAMPLE 38

α-[6-(1-Carboxy-3-phenylpropylamino)-2-(1-naphthyl)-5-oxoperhydro-1,4-thiazepin-4-yl]acetic acid (Compound No. 133)

216 mg of α-[6-(1-ethoxycarbonyl-3-phenylpropylamino)-2-(1-naphthyl)-5-oxoperhydro-1,4-thiazepin-4-yl]acetic acid prepared as described in Example 37, were mixed with 2 ml of a 1N aqueous solution of sodium hydroxide, and the mixture was stirred for 16 hours at room temperature. A small amount of insolubles was filtered off and the pH of the filtrate was adjusted to a value of 2.0 by adding 1N hydrochloric acid; the resulting powdery compound was collected by filtration and washed with a small amount of water, to yield 201 mg of the title compound.

Nuclear Magnetic Resonance Spectrum [(CD$_3$)$_2$SO] δ ppm: 1.7–2.1 (2H, multiplet, PhCH$_2$CH$_2$); 2.5–5.35 (11H, multiplet, PhCH$_2$CH$_2$CH—N, protons of the thiazepine ring, N—CH$_2$—CO); 7.28 (5H, singlet, phenyl protons); 7.1–8.3 (7H, naphthyl protons).

EXAMPLE 39 t-Butyl
α-[6-(1-ethoxycarbonyl-3-phenylpropylamino)-2-(2-naphthyl)-5-oxoperhydro-1,4-thiazepin-4-yl]acetate
(Compound No. 164)

39(a) 2-t-Butoxycarbonylamino-1-(2-naphthyl)ethanol

Crude 2-amino-1-(2-naphthyl)ethanol (obtained by the reduction of 26 g of 2-naphthaldehyde cyanohydrin with lithium aluminum hydride) was t-butoxycarbonylated in the same manner as described in Example 36(a), to give 16 g of the title compound as a crystalline solid melting at 99°–100.5° C.

Nuclear Magnetic Resonance Spectrum (CDCl$_3$)δppm: 1.43 (9H, singlet, t-butyl); 3.1–3.75 (3H, multiplet, —CH$_2$—OH); 4.95 (1H, broad, NH); 4.96 (1H, doublet of doublets, J=4 & 8 Hz, —CH—OH); 7.4–8.0 (7H, multiplet, naphthyl protons).

39(b) 2-t-Butoxycarbonylamino-1-chloro-1-(2-naphthyl)ethane 16 g of 2-t-butoxycarbonylamino-1-(2-naphthyl)ethanol [prepared as described in step (a) above] were chlorinated with phosphorus pentachloride in the same manner as in Example 36(b) to give 9.1 g of the crystalline title compound, melting at 97°–98° C.

Nuclear Magnetic Resonance Spectrum (CDCl$_3$)δppm: 1.43 (9H, singlet, t-butyl); 3.4–4.0 (2H, multiplet, CH$_2$); 4.93 (1H, broad, NH); 5.18 (1H, doublet of doublets, J=6 & 7 Hz, —CH—naphthyl); 7.45–8.0 (7H, multiplet, naphthyl protons).

39(c) Benzhydryl ester of S-[2-t-butoxycarbonylamino-1-(2-naphthyl)ethyl]-N-phthaloylcysteine To a solution of the benzhydryl ester of N-phthaloylcysteine [which was prepared by treating 10 g of L-cysteine p-toluenesulfonate, 7.5 g of N-ethoxycarbonylphthalimide, 6.2 g of sodium bicarbonate and 7.4 g of diphenyldiazomethane in the same manner as in Example 36(c)] and 9.6 g of 2-t-butoxycarbonylamino-1-chloro-1-(2-naphthyl)ethane [prepared as described in step (b) above] in 80 ml of dimethyformamide were added 7.3 g of sodium carbonate. The reaction mixture was stirred at 80° C. for 18 hours under a stream of nitrogen. Treatment of the reaction solution was conducted in the same manner as described in Example 36(c), to give 12.3 g of the title compound as an amorphous solid.

Nuclear Magnetic Resonance Spectrum (CDCl$_3$)δppm: 1.37 (9H, singlet, t-butyl); 3.2–3.7 (4H, multiplet, CH$_2$S, C—CH$_2$—N); 4.22 (1H, triplet, J=4.5 Hz, S—CH—naphthyl); 4.67 (1H, broad, NH); 5.05 (1H, multiplet, N—CH—CO); 6.79 and 7.82 (together 1H, two kinds of singlet, CHPh$_2$); 7.0–8.0 [21H, multiplet, CH(C$_6$H$_5$)$_2$, naphthyl protons, phthaloyl protons].

39(d) S-[2-Amino-1-(2-naphthyl)ethyl]-N-phthaloylcysteine 12.3 g of the benzhydryl ester of S-[2-t-butoxycarbonylamino-1-(2-naphthyl)ethyl]-N-phthaloylcysteine [prepared as described in step (c) above] were treated with trifluoroacetic acid to remove its t-butyl group in the same manner as described in Example 36(c). The title compound (6.6 g) was obtained as powder, melting at 196°–200° C.

39(e) 2-(2-Naphthyl)-5-oxo-6-phthalimidoperhydro-1,4-thiazepine 6.5 g of S-[2-amino-1-(2-naphthyl)ethyl]-N-phthaloylcysteine [prepared as described in step (d) above] were subjected to condensation and cyclization with diphenylphosphoryl azide in the same manner as described in Example 36(e), to give 4.25 g of the title compound, softening from 270° C. and melting at 283°–285° C.

Nuclear Magnetic Resonance Spectrum [(CD$_3$)$_2$SO] δ ppm: 3.1–4.6 (5H, multiplet, CH$_2$—S, N—CH$_2$—CH—S); 5.43 (1H, multiplet, N—CH—CO); 7.5–8.4 (11H, multiplet, naphthyl protons, phthaloyl protons).

39(f) t-Butyl α-[2-(2-naphthyl)-5-oxo-6-phthalimidoperhydro-1,4-thiazepin-4-yl]acetate 4.15 g of 2-(2-naphthyl)-5-oxo-6-phthalimidoperhydro-1,4-thiazepine [prepared as described in step (e) above] were treated with t-butyl bromoacetate in same manner as described in Example 36(f), to give 3.35 g of the title compound as a crystalline solid, melting at 208°–209.5° C.

Nuclear Magnetic Resonance Spectrum (CDCl$_3$) δ ppm: 1.47 (9H, singlet, t-butyl); 2.9–4.85 [7H, multiplet, N—CH$_2$—CH(naphthyl)—S—CH$_2$, N—CH$_2$—CO]; 5.72 (1H, doublet of doublets, J=2 & 10 Hz, N—CH—CO); 7.3–8.0 (11H, multiplet, naphthyl protons, phthaloyl protons).

39(g) t-Butyl α-[6-amino-2-(2-naphthyl)-5-oxoperhydro-1,4-thiazepin-4-yl]acetate 3.25 g of t-butyl α-[2-(2-naphthyl)-5-oxo-6-phthalimidoperhydro-1,4-thiazepin-4-yl]acetate [prepared as described in step (f) above] were subjected to dephthaloylization with methylhydrazine in the same manner as described in Example 36(g), to give 2.6 g of the title compound as an amorphous powder.

Nuclear Magnetic Resonance Spectrum (CDCl$_3$) δ ppm: 1.46 (9H, singlet t-butyl); 2.26 (2H, singlet, NH$_2$); 2.45–4.75 (8H, multiplet, protons of the thiazepine ring, —N—CH$_2$—CO); 7.2–7.9 (11H, multiplet, naphthyl protons, phthaloyl protons).

39(h) t-Butyl α-[6-(1-ethoxycarbonyl-3-phenylpropylamino)-2-(2-naphthyl)-5-oxoperhydro-1,4-thiazepin-4-yl]acetate (Compound No. 164)

0.85 g of t-butyl α-[6-amino-2-(2-naphthyl)-5-oxoperhydro-1,4-thiazepin-4-yl]acetate [prepared as described in step (g) above] was subjected to N-alkylation with 1.08 g of ethyl 2-bromo-4-phenylbutyrate in the same manner as described in Example 36(h). The reaction product was subjected to silica gel column chromatography, using a 1:30 by volume mixture of ethyl acetate and methylene chloride, to separate it into two isomers, A and B (ascribed to the asymmetric carbon atom to which the phenethyl group is attached).

Isomer A was eluted first: an oily substance in a yield of 0.47 g.

Nuclear Magnetic Resonance Spectrum (CDCl$_3$) δ ppm: 1.25 (3H, triplet, J=7.5 Hz, CO$_2$CH$_2$CH$_3$); 1.47 (9H, singlet, t-butyl); 1.7–2.2 (2H, multiplet, PhCH$_2$CH$_2$); 2.4–4.6 (12H, multiplet, PhCH$_2$CH$_2$—CH—NH, protons of the thiazepine ring, N—CH- 2—CO); 4.14 (2H, quartet, J=7.5 Hz, CO$_2$CH$_2$CH$_3$); 7.20 (5H, singlet, phenyl protons); 7.1–7.9 (7H, multiplet, naphthyl protons).

Isomer B was eluted next: an oily substance in a yield of 0.50 g.

Nuclear Magnetic Resonance Spectrum (CDCl$_3$) δ ppm: 1.27 (3H, triplet, J=7.5 Hz, CO$_2$CH$_2$CH$_3$); 1.47 (9H, singlet, t-butyl); 1.8–2.25 (2H, multiplet, PhCH$_2$CH$_2$); 2.5–4.6 (12H, PhCH$_2$CH$_2$—CH—NH; protons of the thiazepine ring, N—CH$_2$—CO); 4.16 (2H, quartet, J=7.5 Hz, CO$_2$CH$_2$CH$_3$); 7.20 (5H, singlet, phenyl protons); 7.1–7.9 (7H, multiplet, naphthyl protons).

EXAMPLE 40

α-[6-(1-Ethoxycarbonyl-B 3-phenylpropylamino)-2-(2-naphthyl)-5-oxoperhydro-1,4-thiazepin-4-yl]acetic acid (Compound No. 139)

0.47 g of isomer B of t-butyl α-[6-(1-ethoxycarbonyl-3-phenylpropylamino)-2-(2-naphthyl)-5-oxo-perhydro-1,4-thiazepin-4-yl]acetate [prepared as described in Example 39(h)] was subjected to de-t-butylation with trifluoroacetic acid in the same manner as described in Example 37, to give 0.42 g of the title compound as a crystalline powder softening from 115° C. and melting at 175°–180° C.

Nuclear Magnetic Resonance Spectrum [(CD$_3$)$_2$SO] δ ppm: 1.30 (3H, triplet, J=7.5 Hz, CO$_2$CH$_2$CH$_3$); 2.0–2.35 (2H, multiplet, PhCH$_2$CH$_2$); 2.55–5.2 (13H, multiplet, PhCH$_2$CH$_2$—CH—N, protons of the thiazepine ring, N—CH$_2$—CO, CO$_2$CH$_2$CH$_3$); 7.33 (5H, singlet, phenyl protons); 7.2–8.1 (7H, multiplet, naphthyl protons).

EXAMPLE 41

α-[6-(1-Carboxy-3-phenylpropylamino)-2-(2-naphthyl)-5-oxoperhydro-1,4-thiazepin-4-yl]acetic acid (Compound No. 138)

200 mg of α-[6-(1-ethoxycarbonyl-3-phenylpropylamino)-2-(2-naphthyl)-5-oxoperhydro-1,4-thiazepin-4-yl]acetic acid (prepared as described in Example 40 above) were hydrolyzed with aqueous sodium hydroxide in the same manner as described in Example 38, to give 133 mg of the title compound as a powder.

Nuclear Magnetic Resonance Spectrum [(CD$_3$)$_2$SO] δ ppm: 1.7–2.1 (2H, multiplet, PhCH$_2$CH$_2$); 2.5–4.8 (11H, multiplet, PhCH$_2$CH$_2$—CH—N, protons of the thiazepine ring, N—CH$_2$—CO); 7.30 (5H, singlet, phenyl protons); 7.2–8.1 (7H, multiplet, naphthyl protons).

EXAMPLE 42 t-Butyl α-8α-(1-ethoxycarbonyl-3-phenylpropylamino)-5-oxo-2-(3-thienyl)perhydro-1,4-thiazepin-4-yl]acetate (Compound No. 120)

42(a) 2-t-Butoxycarbonylamino-1-(3-thienyl)ethanol

Crude 2-amino-1-(3-thienyl)ethanol (which was obtained by the reduction of 28 g of 3-thiophenecarboxaldehyde cyanohydrin with lithium aluminum hydride) was stirred with 30 ml of triethylamine and 44 g of di-t-butyl pyrocarbonate in 200 ml of methanol for 1.5 hours at room temperature. The reaction mixture was then concentrated by evaporation under reduced pressure, and the residue was dissolved in ethyl acetate and water. The organic layer was separated, washed with water and dried over anhydrous magnesium sulfate, and the solvent was evaporated off. The residue was subjected to silica gel column chromatography using a 1:4 by volume mixture of ethyl acetate and methylene chloride as eluent, to yield 13.2 g of the title compound as crystals, melting at 103°–105° C.

Nuclear Magnetic Resonance Spectrum (CDCl$_3$) δ ppm: 1.42 (9H, singlet, t-butyl); 2.9–3.7 (3H, multiplet, —CH$_2$—, OH); 4.83 (1H, doublet of triplets, J=4 & 8 Hz, —CH—OH); 5.0 (1H, broad, NH); 6.95–7.32 (3H, multiplet, protons on thiophene ring).

42(b) 2-t-Butoxycarbonylamino-1-chloro-1-(3-thienyl)ethane

To a solution of 12.2 g of 2-t-butoxycarbonylamino-1-(3-thienyl)ethanol [prepared as described in step (a) above] in 100 ml of absolute methylene chloride was added a solution of 10.4 g of phosphorus pentachloride in 200 ml of absolute methylene chloride at 0° to −5° C. After the addition, the reaction mixture was stirred for 10 minutes. To the reaction mixture was added a 4N aqueous solution of sodium hydroxide, and the mixture was stirred for 5 minutes. The methylene chloride layer was separated, washed with large amount of water and dried over anhydrous magnesium sulfate, and the solvent was evaporated off. The residue was subjected to silica gel column chromatography using a 1:4 by volume mixture of ethyl acetate and cyclohexane as eluent, to yield 7.3 g of the title compound melting at 63°–65° C.

Nuclear Magnetic Resonance Spectrum (CDCl$_3$) δ ppm: 1.43 (9H, singlet, t-butyl); 3.43–3.81 (2H, multiplet, —CH$_2$—); 4.7–5.3 (2H, multiplet, —CH—Cl, NH); 7.0–7.5 (3H, multiplet, protons of the thiophene ring).

42(c) Benzhydryl ester of S-[2-t-butoxycarbonylamino-1-(3-thienyl)ethyl]-N-phthaloylcysteine To a solution of 10 g of L-cysteine p-toluenesulfonate and 7.5 g of N-ethoxycarbonylphthalimide in 68 ml of dimethylformamide were added 6.2 g of sodium bicarbonate under a nitrogen atmosphere. The reaction mixture was then stirred at 90°–100° C. for 3.5 hours. The reaction mixture was cooled and poured into ethyl acetate and potassium hydrogen sulfate, to acidify it. The organic layer was separated, washed with an aqueous solution of sodium chloride and dried over anhydrous magnesium sulfate. To the resulting solution were added 7.4 g of diphenyldiazomethane under a nitrogen atmosphere and the reaction mixture was stirred for 1 hour. The solvent was then evaporated off and the residue was dissolved in 60 ml of dimethylformamide. To this solution were added 8.0 g of 2-t-butoxycarbonylamino-1-chloro-1-(3-thienyl)ethane [prepared as described in step (b) above] and 8.6 g of sodium carbonate under a stream of nitrogen, and the reaction mixture was stirred at 70° C. for 16 hours. The reaction mixture was poured into a mixture of ethyl acetate and water. The organic layer was separated, washed with an aqueous solution of sodium chloride and dried over anhydrous magnesium sulfate, and the solvent was evaporated off. The residue was subjected to silica gel column chromatography using a 1:4 by volume mixture of ethyl acetate and cyclohexane as eluent, to yield 10.9 g of the title compound as an amorphous solid.

Nuclear Magnetic Resonance Spectrum (CDCl$_3$) δ ppm: 1.36 (9H, singlet, t-butyl); 3.1–3.6 (4H, multiplet, CH$_2$S, S—CH$_2$—N); 4.12 (1H, broad triplet, J=7 Hz, S—CH-thienyl); 4.5–5.05 (2H, multiplet, NH, N—CH—CO); 6.76 (1H, singlet, CHPh$_2$); 6.85–7.3 [13H, multiplet, CH(C$_6$H$_5$)$_2$, protons of the thiophene ring]; 7.4–7.85 (4H, multiplet, phthaloyl protons).

42(d)
S-[2-Amino-1-(3-thienyl)ethyl]-N-phthaloylcysteine

To a solution of 10.9 g of the benzhydryl ester of S-[2-t-butoxycarbonylamino-1-(3-thienyl)ethyl]-N-phthaloylcysteine [prepared as described in step (c) above] in 40 ml of anisole were added 50 ml of trifluoroacetic acid, and the reaction mixture was allowed to stand for 2 hours at room temperature. The solvent was evaporated off, and 40 ml of ethyl acetate, 30 ml of water and 2.4 g of sodium bicarbonate were added to the residue, with stirring, and the reaction mixture was adjusted to a pH value of 5.8 with 3N hydrochloric acid. The reaction mixture was stirred, whilst ice-cooling, and the precipitate of the title compound was collected by filtration and washed with a 1:1 by volume mixture of acetone and diethyl ether, to yield 5.9 g of the title compound softening at 165° C.

42(e)
5-Oxo-6-phthalimido-2-(3-thienyl)perhydro-1,4-thiazepine

To a solution of 5.8 g of S-[2-amino-1-(3-thienyl)ethyl]-N-phthaloylcysteine [prepared as described in step (d) above] in 100 ml of dimethylformamide were added 7.7 g of diphenylphophoryl azide and 3.1 ml of N-methylmorpholine. The mixture was stirred for 15 hours at room temperature, and then 200 ml of water and 500 ml of ethyl acetate were added to the reaction mixture, with stirring, to give the desired compound as a solid, in a yield of 2.7 g. Furthermore, the organic layer of the filtrate was separated and evaporated to give more of the title compound. This compound was collected by filtration using a small amount of ethyl acetate and diethyl ether, to yield 1.4 g. The total yield was 4.1 g of the compound melting at 274° C.

Nuclear Magnetic Resonance Spectrum [(CD$_3$)$_2$SO] δ ppm: 2.95–4.35 [5H, multiplet, CH$_2$—S—CH(thienyl)CH$_2$—N]; 5.31 (1H, doublet of doublets, J=4.5 & 8 Hz, N—CH—CO); 7.05–7.15 (1H, multiplet, proton at the 4-position of the thiophene ring); 7.4–7.5 (2H, multiplet, protons at the 2 and 5-positions of the thiophene ring); 7.82 (4H, singlet, phthaloyl protons); 8.02 (1H, broad, NH).

42(f) t-Butyl
α-[5-oxo-6-phthalimido-2-(3-thienyl)perhydro-1,4-thiazepin-4-yl]acetate To a suspension of 4.1 g of 5-oxo-6-phthalimido-2-(3-thienyl)perhydro-1,4-thiazepine [prepared as described in step (e) above] in 60 ml of dimethylformamide were added dropwise 2.2 g of t-butyl bromoacetate, followed by 593 mg of a 55% w/w suspension of sodium hydride in oil at 0° to −5° C. under a stream of nitrogen. The reaction mixture was stirred at 0° C. for 20 minutes and then poured into a mixture of ethyl acetate and water. The ethyl acetate layer was separated, washed with water and dried over anhydrous magnesium sulfate, and the solvent was evaporated off. The semi-solid residue was collected by filtration using ethyl acetate and diisopropyl ether, to yield 3.7 g of the title compound, melting at 157°–160° C. (with decomposition).

Nuclear Magnetic Resonance Spectrum [(CD$_3$)$_2$SO] δ ppm: 1.46 (9H, s, t-butyl); 2.8–4.6 (7H, multiplet, CH$_2$—S—CH(thienyl)—CH$_2$ N, N—CH$_2$—CO); 5.60 (1H, doublet of doublets, J=3 & 8 Hz, N—CH—CO); 7.05–7.42 (3H, multiplet, protons of the thiophene ring); 7.7–7.85 (4H, multiplet, phthaloyl protons).

42(g) t-Butyl
α-[6-amino-5-oxo-2-(3-thienyl)perhydro-1,4-thiazepin-4-yl]acetate To a solution of 3.6 g of t-butyl α-[5-oxo-6-phthalimio-2-(3-thienyl)perhydro-1,4-thiazepin-4-yl]acetate [prepared as described in step (f) above] in 40 ml of methylene chloride and 10 ml of methanol were added 1.8 ml of methylhydrazine, and the reaction mixture was allowed to stand for 16 hours at room temperature. The reaction mixture was then concentrated by evaporation under reduced pressure, and methylene chloride added to the residue whilst stirring. The resulting precipitate was filtered off and the filtrate was concentrated. The residue was subjected to silica gel column chromatography using a 1:4:5 by volume mixture of methanol, cyclohexane and ethyl acetate as the eluent, to yield 2.33 g of the title compound as a solid, melting at 115°–117° C.

Nuclear Magnetic Resonance Spectrum (CDCl$_3$) δ ppm: 1.48 (9H, singlet, t-butyl); 2.10 (2H, broad singlet, NH$_2$); 2.4–4.6 (8H, multiplet, thiazepine ring protons, —N—CH$_2$CO); 6.9–7.35 (3H, multiplet, protons of the thiophene ring).

42(h) t-Butyl
α-[6-(1-ethoxycarbonyl-3-phenylpropylamino)-5-oxo-2-(3-thienyl)perhydro-1,4-thiazepin-4-yl]acetate
(Compound No. 120)

To a solution of 0.47 g of t-butyl α-[6-amino-5-oxo-2-(3-thienyl)perhydro-1,4-thiazepin-4-yl]acetate [prepared as described in step (d) above] and 0.8 g of ethyl 2-bromo-4-phenylbutyrate in 7 ml of dimethylformamide was added 1.0 g of sodium carbonate. The reaction mixture was stirred at 70° C. for 18 hours and then dissolved in ethyl acetate and an aqueous solution of sodium chloride. The ethyl acetate layer was separated, washed with water and dried over anhydrous magnesium sulfate, and the solvent was evaporated off. The residue was subjected to silica gel column chromatography using a 1:20 by volume mixture of ethyl acetate and methylene chloride to give two isomers, A and B (ascribed to the asymmetric carbon atom to which the phenethyl group is attached). The first eluted isomer A was an oily compound in a yield of 0.27 g.

Nuclear Magnetic Resonance Spectrum (CDCl$_3$) δ ppm: 1.23 (3H, triplet, J=7.5 Hz, CO$_2$CH$_2$CH$_3$); 1.46 (9H, singlet, t-butyl); 1.7–2.2 (2H, multiplet, PhCH$_2$CH$_2$); 2.3–4.6 (14H, multiplet, PhCH$_2$CH$_2$CH—NH, protons of the thiazepine ring, N—CH$_2$—CO, CO$_2$CH$_2$CH$_3$); 6.9–7.4 (3H, multiplet, thiophene ring protons); 7.19 (5H, singlet, phenyl protons).

The second eluted isomer B was an oily compound in a yield of 0.30 g.

Nuclear Magnetic Resonance Spectrum (CDCl$_3$) δ ppm: 1.25 (3H, triplet, J=7.5 Hz, CO$_2$CH$_2$CH$_3$); 1.47 (9H, singlet, t-butyl); 1.8–2.2 (2H, multiplet, PhCH$_2$CH$_2$); 2.5–4.55 (14H, multiplet, PhCH$_2$CH$_2$—CH—NH, protons of the thiazepine ring, N—CH$_2$—CO, CO$_2$CH$_2$CH$_3$); 6.9–7.35 (3H, multiplet, protons of the thiophene ring); 7.19 (5H, singlet, phenyl protons).

EXAMPLE 43

α-[6-(1-Ethoxycarbonyl-3-phenylpropylamino)-5-oxo-2-(3-thienyl)perhydro-1,4-thiazepin-4-yl]acetic acid
(Compound No. 83)

300 mg of isomer B of t-butyl α-[6-(1-ethoxycarbonyl-3-phenylpropylamino)-5-oxo-2-(3-thienyl)perhydro-1,4-thiazepin-4-yl]acetate [prepared as described in Example 42(h)] were dissolved in 1.8 ml of anisole and 2 ml of trifluoroacetic acid. The reaction mixture was then allowed to stand for 3 hours at room temperature, after which it was concentrated by evaporation under reduced pressure. Diisopropyl ether was added to the residue, with stirring, and the resulting powdery insoluble matter was collected by filtration, to yield 258 mg of a powder.

To a suspension of this power in 4 ml of water were added 0.3 g of sodium bicarbonate and 10 ml of ethyl acetate. The mixture was stirred for 10 minutes and then adjusted to a pH value of 2.5 by adding 3N hydrochloric acid. The ethyl acetate layer was separated, and the aqueous layer was extracted with ethyl acetate. The resulting ethyl acetate solutions were combined and dried over anhydrous magnesium sulphate, and the solvent was evaporated off, to give the title compound as a crystalline powder. This powder was collected by filtration and washed with a mixture of diisopropyl ether and cyclohexane, to yield 205 mg of the title compound, softening at around 140° C. and melting at 165° C.

Nuclear Magnetic Resonance Spectrum (CDCl$_3$) δ ppm: 1.26 (3H, triplet, J=7.5 Hz, CO$_2$CH$_2$CH$_3$); 1.9–2.5 (2H, multiplet, PhCH$_2$CH$_2$); 2.5–4.7 (13H, multiplet, PhCH$_2$CH$_2$CH—N, protons of the thiazepine ring, N—CH$_2$—CO, CO$_2$CH$_2$CH$_3$CH); 6.75–7.3 (3H, multiplet, protons of the thiophene ring); 7.19 (5H, singlet, phenyl protons).

EXAMPLE 44

α-[6-(1-Carboxy-3-phenylpropylamino)-5-oxo-2-(3-thienyl)perhydro-1,4-thiazepin-4-yl]acetic acid
(Compound No. 82)

150 mg of α-[6-(1-ethoxycarbonyl-3-phenylpropylamino)-5-oxo-2-(3-thienyl)perhydro-1,4-thiazepin-4-yl]acetic acid (prepared as described in Example 43) were mixed with 2 ml of a 1N aqueous solution of sodium hydroxide, and the mixture was stirred for 16 hours. The reaction mixture was then adjusted to a pH value of 2.0 with 1N hydrochloric acid and the resulting solid, which was the title compound, was collected by filtration and washed with small amount of water and diisopropyl ether, to yield 120 mg.

Nuclear Magnetic Resonance Spectrum [(CD$_3$)$_2$SO] δ ppm: 1.7–2.1 (2H, multiplet, PhCH$_2$CH$_2$); 2.5–4.6 (11H, multiplet, PhCH$_2$CH$_2$CH—N, protons of the thiazepine ring, N—CH$_2$CO); 7.1–7.65 (3H, multiplet, protons of the thiophene ring); 7.27 (5H, singlet, phenyl protons).

EXAMPLE 45 t-Butyl α-[6-(1-butoxycarbonyl-3-phenylpropylamino)-5-oxo-2-(3-thienyl)perhydro-1,4-thiazepin-4-yl]acetate
(Compound No. 197)

0.66 g of t-butyl α-[6-amino-5-oxo-2-(3-thienyl)perhydro-1,4-thiazepin-4-yl]acetate [synthesized as described in Example 42(g)] was N-alkylated using 0.86 g of butyl 2-bromo-4-phenylbutyrate by the same procedure as is described in Example 42(h). The reaction product was subjected to silica gel column chromatography using a 1:20 by volume mixture of ethyl acetate and methylene chloride, to give two isomers, A and B (ascribed to the asymmetric carbon atom to which the phenethyl group is attached).

The first eluted isomer A was an oily compound in a yield of 140 mg.

Nuclear Magnetic Resonance Spectrum (CDCl$_3$) δ ppm: 0.7–1.1 (3H, multiplet, CH$_3$ of n-butyl); 1.46 (9H, singlet, t-butyl); 1.1–2.3 (7H, multiplet, CO$_2$CH$_2$(CH$_2$)$_2$CH$_3$, PhCH$_2$CH$_2$, NH]; 2.3–4.5 [13H, multiplet, PhCH$_2$CH$_2$—CH—N, thiazepine ring protons, N—CH$_2$—CO, CO$_2$CH$_2$(CH$_2$)$_2$CH$_3$]; 6.85–7.3 (8H, multiplet, phenyl protons, protons of the thiophene ring).

The second eluted isomer B was an oily compound in a yield of 140 mg.

Nuclear Magnetic Resonance Spectrum (CDCl$_3$) δ ppm: 0.8–1.1 (3H, multiplet, CH$_3$ of n-butyl); 1.47 (9H, singlet, t-butyl); 1.1–2.3 [7H, multiplet, CO$_2$CH$_2$(CH$_2$)$_2$CH$_3$, PhCH$_2$CH$_2$,NH]; 2.4–4.5 [13H, multiplet, PhCH$_2$CH$_2$—CH—N, thiazepine ring protons, N—CH$_2$—CO, CO$_2$CH$_2$(CH$_2$)$_2$CH$_3$]; 6.85–7.5 (8H, multiplet, phenyl protons, protons of the thiophene ring).

EXAMPLE 46

α-[6-(1-Butoxycarbonyl-3-phenylpropylamino)-5-oxo-2-(3-thienyl)perhydro-1,4-thiazepin-4-yl]acetic acid
(Compound No. 84)

130 mg of isomer B of t-butyl α-[6-(1-butoxycarbonyl-3-phenylpropylamino)-5-oxo-2-(3-thienyl)perhydro-1,4-thiazepin-4-yl]acetate (prepared as described in Example 45 above) were treated with trifluoroacetic acid by the same procedure as is described in Example 43 to remove the t-butyl group and give the title compound as a crystalline powder, melting at 156° C., in a yield of 70 mg.

Nuclear Magnetic Resonance Spectrum (CDCl$_3$) δ ppm: 0.7–1.1 (3H, multiplet, CH$_3$ of n-butyl); 1.1–1.9 [4H, multiplet, CO$_2$CH$_2$(CH$_2$)$_2$CH$_3$]; 2.0–2.6 (2H, multiplet, PhCH$_2$CH$_2$); 2.6–4.9 [13H, multiplet, PhCH$_2$CH$_2$CH—N, thiazepine ring protons, N—CH$_2$—CO, CO$_2$CH$_2$(CH$_2$)$_2$CH$_3$]; 6.75–7.3 (3H, multiplet, protons of the thiophene ring); 7.21 (5H, singlet, phenyl protons).

EXAMPLE 47 t-Butyl α-[6-(1-benzyloxycarbonyl-3-phenylpropylamino)-5-oxo-2-(3-thienyl)perhydro-1,4-thiazepin-4-yl]-acetate
(Compound No. 209)

0.3 g of t-butyl α-[6-amino-5-oxo-2-(3-thienyl)perhydro-1,4-thiazepin-4-yl]acetate [synthesized as described in Example 42(g)], was N-alkylated using 0.6 g of benzyl 2-bromo-4-phenylbutyrate by the procedure described in Example 42(h). The reaction product was chromatographed on a silica gel column eluted with a 1:40 by volume mixture of ethyl acetate and methylene chloride, to give two isomers, A and B (ascribed to the asymmetric carbon atom to which the phenethyl group is attached).

The first eluted isomer A was an oily compound in a yield of 0.10 g.

Nuclear Magnetic Resonance Spectrum (CDCl$_3$) δ ppm: 1.46 (9H, singlet, t-butyl); 1.72–2.2 (2H, multiplet, PhCH$_2$CH$_2$); 2.3–4.6 (12H, multiplet, PhCH$_2$CH$_2$CH—NH, thiazepine ring protons, N—CH$_2$—C̄Ō); 5.06 (2H, AB quartet, Δδ=0.21 ppm, J=13 Hz, CH$_2$Ph); 6.8–7.3 (3H, multiplet, protons of the thiophene ring); 7.10, 7.26 (together 10H, each singlet, protons of the 2 phenyl groups).

The second eluted isomer B was an oily compound in a yield of 0.21 g.

Nuclear Magnetic Resonance Spectrum (CDCl$_3$) δ ppm: 1.46 (9H, singlet, t-butyl); 1.75–2.2 (2H, multiplet, PhCH$_2$CH$_2$); 2.4–4.5 (12H, multiplet, PhCH$_2$CH$_2$CH—NH, thiazepine ring protons, N—CH$_2$—C̄Ō); 5.08 (2H, singlet, CH$_2$Ph); 6.8–7.3 (3H, multiplet, protons of the thiophene ring); 7.10, 7.27 (together 10H, each singlet, protons of the 2 phenyl groups).

EXAMPLE 48

α-[6-(1-Benzyloxycarbonyl-3-phenylpropylamino)-5-oxo-2-(3-thienyl)perhydro-1,4-thiazepin-4-yl]acetic acid (Compound No. 86)

180 mg of isomer B of t-butyl α-[6-(1-benzyloxycarbonyl-3-phenylpropylamino)-5-oxo-2-(3-thienyl)perhydro-1,4-thiazepin-4-yl]acetate were treated with trifluoroacetic acid by the procedure described in Example 43, to remove the t-butyl group and give 140 mg of the title compound as a powder.

Nuclear Magnetic Resonance Spectrum (CDCl$_3$) δ ppm: 1.9–2.45 (2H, multiplet, PhCH$_2$CH$_2$); 2.5–4.7 (11H, multiplet, PhCH$_2$CH$_2$CH—N, thiazepine ring protons, N—CH$_2$—C̄Ō); 5.16 (2H, singlet, CH$_2$Ph); 6.7–7.3 (3H, multiplet, protons of the thiophene ring); 7.13, 7.32 (together 10H, each singlet, protons of the 2 phenyl groups).

EXAMPLE 49 t-Butyl α-[6-(1-ethoxycarbonyl-3-phenylpropylamino)-5-oxo-2-(2-thienyl)perhydro-1,4-thiazepin-4-yl]acetate (Compound No. 119)

49(a) 2-t-Butoxycarbonylamino-1-(2-thienyl)ethanol

Crude 2-amino-1-(2-thienyl)ethanol (obtained by the reduction of 62 g of 2-thiophenecarboxaldehyde cyanohydrin with lithium aluminum hydride) was t-butoxycarbonylated by the procedure described in Example 42(a) and 45 g of the title compound were obtained as a crystalline solid, melting at 101°–102° C.

Nuclear Magnetic Resonance Spectrum (CDCl$_3$) δ ppm: 1.43 (9H, singlet, t-butyl); 3.0–3.6 (3H, multiplet, —CH$_2$—, OH); 5.00 (1H, doublet of doublets, J=4 & 7.5 Hz, CH—CH); 4.8–5.2 (1H, broad triplet, NH); 6.94 (2H, multiplet, protons at the 3- and 4-positions of the thiophene ring); 7.18 (1H, multiplet, proton at the 5-position of the thiophene ring).

49(b) 2-t-Butoxycarbonylamino-1-chloro-1-(2-thienyl)ethane

Following the procedure described in Example 42(b), 15 g of 2-t-butoxycarbonylamino-1-(2-thienyl)ethanol were chlorinated using phosphorus pentachloride to afford 13.6 g of the title product as crystals melting at 40°–43° C. This substance was used for next step without purification because it was decomposed by silica gel column chromatography.

Nuclear Magnetic Resonance Spectrum (CDCl$_3$) δ ppm: 1.43 (9H, singlet, t-butyl); 3.5–3.8 (2H, multiplet, —CH$_2$—); 4.90 (1H, broad multiplet, NH); 5.21 (1H, doublet of doublets, J=6 & 7 Hz, —CH—Cl); 6.75–7.3 (3H, multiplet, protons of the thiophene ring).

49(c) Benzhydryl ester of S-[2-t-Butoxycarbonylamino-1-(2-thienyl)ethyl]-N-phthaloylcysteine Following the procedure described in Example 42(c), the benzhydryl ester of N-phthaloyl-L-cysteine (prepared from 10 g of L-cysteine p-toluenesulfonate, 7.5 g of N-ethoxycarbonylphthalimide, 6.2 g of sodium bicarbonate and 7.4 g of diphenyldiazomethane) and 10 g of 2-t-butoxycarbonylamino-1-chloro-1-(2-thienyl)ethane [prepared as described in step (b) above] were dissolved in 60 ml of dimethylformamide. To the solution were added 8.6 g of sodium carbonate and the mixture was stirred for 16 hours at 60° C. under a stream of nitrogen. Treatment of the reaction mixture was then conducted in the same manner as in Example 42(c), to give the title product as an amorphous solid in a yield of 7.3 g.

Nuclear Magnetic Resonance Spectrum (CDCl$_3$) δ ppm: 1.38 (9H, singlet, t-butyl); 3.0–3.7 (4H, multiplet, CH$_2$S, C—CH$_2$—N); 4.31 (1H, broad triplet, J=7 Hz, S—CH—thienyl); 4.75 (1H, broad multiplet, NH); 4.92 (1H, doublet of doublets, J=6.5 & 7.5 Hz, N—CH—CO); 6.7–7.3 [14H, multiplet, CH(C$_6$H$_5$)$_2$, protons of the thiophene ring]; 7.5–7.85 (4H, multiplet, phthaloyl protons).

49(d) S-[2-Amino-1-(2-thienyl)ethyl]-N-phthaloylcysteine

Following the procedure described in Example 42(d), 9.3 g of the benzhydryl ester of S-[2-t-butoxycarbonylamino-1-(2-thienyl)ethyl]-N-phthaloylcysteine [prepared as described in step (c) above] were deprotected using trifluoroacetic acid to give 1.7 g of the title compound as a pale yellow powder.

49(e) 5-Oxo-6-phthalimido-2-(2-thienyl)perhydro-1,4-thiazepine

Following the procedure described in Example 42(e), 1.7 g of S-[2-amino-1-(2-thienyl)ethyl]-N-phthaloylcysteine [prepared as described in step (d) above] was cyclized by condensation using 1.75 ml of diphenylphosphoryl azide to afford 1.15 g of the title compound melting at 183°–184° C.

Nuclear Magnetic Resonance Spectrum [(CD$_3$)$_2$SO] δ ppm: 2.95–3.95 (4H, multiplet, CH$_2$—S, N—CH$_2$—C); 4.46 (1H, doublet of doublets, J=4 & 8 Hz, S—CH-thienyl); 5.33 (1H, doublet of doublets, J=5 & 8 Hz, N—CH—CO); 6.9–7.5 (3H, multiplet, protons of the thiophene ring); 7.87 (4H, singlet, phthaloyl protons); 8.12 (1H, broad triplet, J=7 Hz, NH).

49(f) t-Butyl α-[5-oxo-6-phthalimido-2-(2-thienyl)perhydro-1,4-thiazepin-4-yl]acetate Following the procedure described in Example 42(f), 1.6 g of 5-oxo-6-phthalimido-2-(2-thienyl)perhydro-1,4-thiazepine [prepared as described in step (e) above] was treated with t-butyl bromoacetate to give 1.15 g of the title compound as crystals, melting at 183°–184° C.

Nuclear Magnetic Resonance Spectrum (CDCl$_3$) δ ppm: 1.47 (9H, singlet, t-butyl); 2.9–4.9 [7H, multiplet, N—CH$_2$—CH(thienyl)—S—CH$_2$, N—CH$_2$—CO]; 5.67 (1H, doublet of doublets, J=3 & 10 Hz, N—CH—CO);

6.95–7.35 (3H, multiplet, protons of the thiophene ring); 7.65–8.0 (4H, multiplet, phthaloyl protons).

49(g) t-Butyl α-[6-amino-5-oxo-2-(2-thienyl)perhydro-1,4-thiazepin-4-yl]acetate Following the procedure described in Example 42(g), 1.1 g of t-butyl α-[5-oxo-6-phthalimido-2-(2-thienyl)perhydro-1,4-thiazepin-4-yl]acetate [prepared as described in step (f) above] was dephthaloylized with methylhydrazine, to afford 0.52 g of the title compound as a crystalline powder, melting at 84°–86.5° C.

Nuclear Magnetic Resonance Spectrum (CDCl$_3$) δ ppm: 1.47 (9H, singlet, t-butyl); 2.29 (2H, broad singlet, NH$_2$); 2.6–4.7 (8H, multiplet, thiazepine ring protons —N—CH$_2$—CO; 6.75–7.2 (3H, multiplet, protons of the thiopene ring).

49(h) t-Butyl α-[6-(1-ethoxycarbonyl-3-phenylpropylamino)-5-oxo-2-(2-thienyl)perhydro-1,4-thiazepin-4-yl]acetate (Compound No. 119)

Following the procedure described in Example 42(h), 0.40 g of t-butyl α-[6-amino-5-oxo-2-(2-thienyl)perhydro-1,4-thiazepin-4-yl]acetate [prepared as described in step (g) above] was N-alkylated using 0.64 g of ethyl 2-bromo-4-phenylbutyrate. The resulting product was subjected to silica gel column chromatography eluted with a 1:20 by volume mixture of ethyl acetate and methylene chloride, to separate it into two isomers, A and B, (ascribed to the asymmetric carbon atom to which the phenethyl group is attached).

From the fraction initially eluted was obtained 0.21 g of isomer A as an oily substance.

Nuclear Magnetic Resonance Spectrum (CDCl$_3$) δ ppm: 1.24 (3H, triplet, J=7.5 Hz, CO$_2$CH$_2$CH$_3$); 1.48 (9H, singlet, t-butyl); 1.7–2.3 (2H, multiplet, PhCH$_2$CH$_2$); 2.4–4.8 (14H, multiplet, PhCH$_2$CH—CH—NH, thiazepine ring protons, N—CH$_2$—CO, CO$_2$CH$_2$CH$_3$); 6.85–7.35 (3H, multiplet, protons of the thiophene ring); 7.20 (5H, singlet, phenyl protons).

From the fraction eluted subsequently was obtained 0.30 g of isomer B as an oily substance.

Nuclear Magnetic Resonance Spectrum (CDCl$_3$) δ ppm: 1.26 (3H, triplet, J=7.5 Hz, CO$_2$CH$_2$CH$_3$); 1.48 (9H, singlet, t-butyl); 1.8–2.5 (2H, multiplet, PhCH$_2$CH$_2$); 2.55–4.8 (12H, multiplet, PhCH$_2$CH$_2$—CH—NH, thiazepine ring protons, N—CH$_2$—CO); 4.15 (12H, quartet, J=7.5 Hz, CO$_2$CH$_2$CH$_3$); 6.85–7.35 (3H, multiplet, protons of the thiophene ring); 7.20 (5H, singlet, phenyl protons).

EXAMPLE 50

α-[6-(1-Ethoxycarbonyl-3-phenylpropylamino)-5-oxo-2-(2-thienyl)perhydro-1,4-thiazepin-4-yl]acetic acid (Compound No. 78)

Following the procedure described in Example 43, 0.3 g of isomer B of t-butyl α-[6-(1-ethoxycarbonyl-3-phenylpropylamino)-5-oxo-2-(2-thienyl)perhydro-1,4-thiazepin-4-yl]acetate [obtained as described in Example 49(h)], was de-t-butyrated using trifluoroacetic acid to afford the desired product as a crystalline powder in a yield of 83 mg. The product softened at about 135° C. and melted at 168° C.

Nuclear Magnetic Resonance Spectrum [(CD$_3$)$_2$SO] δ ppm: 1.26 (3H, triplet, J=7.5 Hz, CO$_2$CH$_2$CH$_3$); 1.9–2.3 (2H, multiplet, PhCH$_2$CH$_2$); 2.5–5.1 (13H, multiplet, PhCH$_2$CH$_2$—CHN, thiazepine ring protons, N—CH$_2$CO, CO$_2$CH$_2$CH$_3$); 7.0–7.6 (3H, multiplet, protons of the thiophene ring); 7.30 (5H, singlet, phenyl protons).

EXAMPLE 51

α-[6-(1-Carboxy-3-phenylpropylamino)-5-oxo-2-thienyl)perhydro-1,4-thiazepin-4-yl]acetic acid (Compound No. 77)

Following the procedure described in Example 44, 70 mg of α-[6-(1-ethoxycarbonyl-3-phenylpropylamino)-5-oxo-2-(2-thienyl)perhydro-1,4-thiazepin-4-yl]acetic acid (prepared as described in Example 50 above) were hydrolyzed with sodium hydroxide to afford 52 mg of the title compound as a powder.

Nuclear Magnetic Resonance Spectrum [(CD$_3$)$_2$SO] δ ppm: 1.7–2.05 (2H, multiplet, PhCH$_2$CH$_2$); 2.5–4.8 (11H, multiplet, PhCH$_2$CH$_2$CH—N, thiazepine ring protons, N—CH$_2$CO); 7.0–7.55 (3H, multiplet, protons of the thiophene ring); 7.28 (5H, singlet, phenyl protons).

EXAMPLE 52 t-Butyl α-[6-(1-butoxycarbonyl-3-phenylpropylamino)-5-oxo-2-(2-thienyl)perhydro-1,4-thiazepin-4-yl]acetate (Compound No. 196)

Following the procedure described in Example 42(h), 0.40 g of t-butyl α-[6-amino-5-oxo-2-(2thienyl)perhydro-1,4-thiazepin-4-yl]acetate [prepared as described in Example 49(g)] was N-alkylated using 0.52 g of butyl 2-bromo-4-phenylbutyrate. The resulting product was subjected to silica gel column chromatography eluted with a 1:20 by volume mixture of ethyl acetate and methylene chloride, to separate it into two isomers, A and B, (ascribed to the asymmetric carbon atom to which the phenethyl group is attached).

From the fraction initially eluted were obtained 125 mg of isomer A as an oily substance.

Nuclear Magnetic Resonance Spectrum (CDCl$_3$) δ ppm: 0.7–1.1 (3H, multiplet, CH$_3$ of n-butyl); 1.46 (9H, singlet, t-butyl); 1.1–2.3 (6H, multiplet, CO$_2$CH$_2$(CH$_2$)$_2$CH$_3$, PhCH$_2$CH$_2$); 2.3–4.7 [14H, multiplet, PhCH$_2$CH$_2$CH—NH, thiazepine ring protons, N—CH$_2$CO, CO$_2$CH$_2$(CH$_2$)$_2$CH$_3$]; 6.85–7.35 (3H, multiplet, protons of the thiophene ring), 7.18 (5H, multiplet, phenyl protons).

From the fraction eluted subsequently were obtained 120 mg of isomer B as an oily substance.

Nuclear Magnetic Resonance Spectrum (CDCl$_3$) δ ppm: 0.7–1.1 (3H, multiplet, CH$_3$ of n-butyl); 1.47 (9H, singlet, t-butyl); 1.1–2.3 (6H, multiplet, CO$_2$CH$_2$(CH$_2$)$_2$CH$_3$, PhCH$_2$CH$_2$); 2.3–4.8 [14H, multiplet, PhCH$_2$CH$_2$CH—NH, thiazepine ring protons, N—CH$_2$—CO, CO$_2$CH$_2$(CH$_2$)$_2$CH$_3$]; 6.85–7.35 (3H, multiplet, protons of the thiophene ring); 7.18 (5H, singlet, phenyl protons).

EXAMPLE 53

α-[6-(1-Butoxycarbonyl-3-phenylpropylamino)-5-oxo-2-(2-thienyl)perhydro-1,4-thiazepin-4-yl]acetic acid (Compound No. 79)

Following the procedure described in Example 43, 120 mg of isomer B of t-butyl α-[6-(1-butoxycarbonyl-3-phenylpropylamino)-5-oxo-2-(2-thienyl)perhydro-1,4-thiazepin-4-yl]acetate (prepared as described in Example 52) were de-t-butylated using trifluoroacetic acid, to afford 75 mg of the title compound as a powder.

Nuclear Magnetic Resonance Spectrum (CDCl$_3$) δ ppm: 0.7–1.1 (3H, multiplet, CH$_3$ of n-butyl); 1.1–1.9 [4H, multiplet, CO$_2$CH$_2$(CH$_2$)$_2$CH$_3$]; 1.9–2.5 (2H, multiplet, PhCH$_2$CH$_2$); 2.5–4.9 [13H, multiplet, PhCH$_2$CH$_2$CH—N, thiazepine ring protons, N—CH$_2$—CO, CO$_2$CH$_2$(CH$_2$)$_2$CH$_3$]; 6.8–7.35 (3H, multiplet, protons of the thiophene ring); 7.20 (5H, singlet, phenyl protons).

EXAMPLE 54 t-Butyl α-[6-(1-benzyloxycarbonyl-3-phenylpropylamino)-5-oxo-2-(2-thienyl)perhydro-1,4-thiazepin-4-yl]acetate (Compound No. 210)

Following the same procedure described in Example 42(h), 0.4 g of t-butyl α-[6-amino-5-oxo-2-(2-thienyl)-perhydro-1,4-thiazepin-4-yl]acetate [prepared as described in Example 49(g)] was N-alkylated using 0.80 g of benzyl 2-bromo-4-phenylbutyrate. The resulting product was subjected to silica gel column chromatography eluted with a 1:40 by volume mixture of ethyl acetate and methylene chloride to separate it into two isomers, A and B, (ascribed to the asymmetric carbon atom to which the phenethyl group is attached).

From the fraction eluted initially was obtained 0.15 g of isomer A as an oily substance.

Nuclear Magnetic Resonance Spectrum (CDCl$_3$) δ ppm: 1.46 (9H, singlet, t-butyl); 1.7–2.2 (2H, multiplet, PhCH$_2$CH$_2$); 2.3–4.6 (12H, multiplet, PhCH$_2$CH$_2$CH—NH, thiazepine ring protons, N—CH$_2$—CO); 5.05 (2H, AB quartet, Δδ=0.21 ppm, J=13 Hz, CH$_2$Ph); 6.8–7.35 (3H, multiplet, protons of the thiophene ring); 7.10, 7.25 (together 10H, each singlet, protons of the 2 phenyl groups).

From the fraction eluted subsequently was obtained 0.20 g of isomer B as an oily substance.

Nuclear Magnetic Resonance Spectrum (CDCl$_3$) δ ppm: 1.46 (9H, singlet, t-butyl); 1.75–2.2 (2H, multiplet, PhCH$_2$CH$_2$); 2.35–4.55 (12H, multiplet, PhCH$_2$CH$_2$CH—NH, thiazepine ring protons, N—CH$_2$—CO); 5.06 (2H, singlet, CH$_2$Ph); 6.8–7.3 (3H, multiplet, protons of the thiophene ring); 7.10, 7.26 (together 10H, each singlet protons of the 2 phenyl groups).

EXAMPLE 55

α-[6-(1-Benzyloxycarbonyl-3-phenylpropylamino)-5-oxo-2-(2-thienyl)perhydro-1,4-thiazepin-4-yl]acetic acid (Compound No. 81)

Following the procedure described in Example 43, 180 mg of isomer B of t-butyl α-[6-(1-benzyloxycarbonyl-3-phenylpropylamino)-5-oxo-2-(2-thienyl)perhydro-1,4-thiazepin-4-yl]acetate (prepared as described in Example 54) was de-t-butylated using trifluoroacetic acid, to afford 135 mg of the title compound as a powder.

Nuclear Magnetic Resonance Spectrum (CDCl$_3$) δ ppm: 1.9–2.4 (2H, multiplet, PhCH$_2$CH$_2$); 2.45–4.7 (11H, multiplet, PhCH$_2$CH$_2$CH—N, thiazepine ring protons, N—CH$_2$—CO); 5.15 (2H, singlet, CH$_2$Ph); 6.85–7.35 (3H, multiplet, protons of the thiophene ring); 7.13, 7.32 (together 10H, each singlet, protons of the 2 phenyl groups).

EXAMPLE 56 t-Butyl α-[6-(1-ethoxycarbonyl-3-phenylpropylamino)-2-(2-furyl)-5-oxoperhydro-1,4-thiazepin-4-yl]acetate (Compound No. 211)

56(a) 2-t-Butoxycarbonylamino-1-(2-furyl)ethanol

Following the procedure described in Example 42(a), crude 2-amino-1-(2-furyl)ethanol (obtained by the reduction of 63 g of furfural cyanohydrin with lithium aluminum hydride) was t-butoxycarbonylated to afford 36.7 g of the title compound as crystals, melting at 89°–90° C.

Nuclear Magnetic Resonance Spectrum (CDCl$_3$) δ ppm: 1.43 (9H, singlet, t-butyl); 3.3–3.65 (3H, multiplet, —CH$_2$—, OH); 4.74 (1H, doublet of triplets, J=5 & 6.5 Hz, —CH—OH); 5.07 (1H, broad triplet, J=5 Hz, NH); 6.28 (2H, multiplet, protons at the 3- and 4-positions of the furan ring); 7.33 (1H, multiplet, protons at the 5-position of the furan ring).

56(b) 2-t-Butoxycarbonylamino-1-chloro-1-(2-furyl)ethane

Following the procedure described in Example 42(b), 14 g of 2-t-butoxycarbonylamino-1-(2-furyl)ethanol [prepared as described in step (a) above] was treated with phosphorus pentachloride to afford 15 g of the title compound as crystals, melting at 75°–77° C. This substance was used for the next step without purification because it was decomposed by silica gel column chromatography.

Nuclear Magnetic Resonance Spectrum (CDCl$_3$) δ ppm: 1.43 (9H, singlet, t-butyl); 3.55–3.85 (2H, multiplet, —CH$_2$—); 5.00 (1H, broad, NH); 5.05 (1H, doublet of doublets, J=5.5 & 6.5 Hz, —CH—Cl); 6.33 (2H, multiplet, protons at the 3- and 4-positions of the furan ring); 7.39 (1H, multiplet, protons at the 5-position of the furan ring).

56(c) Benzhydryl ester of S-[2-t-butoxycarbonylamino-1-(2-furyl)ethyl]-N-phthaloylcysteine Following the procedure described in Example 42(c), the benzhydryl ester of N-phthaloyl-L-cysteine (prepared from 15 g of L-cysteine p-toluenesulfonate, 11.3 g of N-ethoxycarbonylphthalimide, 9.3 g of sodium bicarbonate and 11 g of diphenyldiazomethane) and 15 g of 2-t-butoxycarbonylamino-1-chloro-1-(2-furyl)ethane [prepared as described in step (b) above] were dissolved in 90 ml of dimethylformamide. To this solution were added 12.9 g of sodium carbonate, and the mixture was stirred for 16 hours at 60° C. under a stream of nitrogen. Treatment of the reaction mixture was then conducted in the same manner as in Example 42(c), to give the title compound as an amorphous solid in a yield of 7.6 g.

Nuclear Magnetic Resonance Spectrum (CDCl$_3$) δ ppm: 1.39 (9H, singlet, t-butyl); 3.2–3.7 (4H, multiplet, CH$_2$S, C—CH$_2$—N); 4.13 (1H, broad triplet, J=7.5 Hz, —S—CH—furyl); 4.7–5.1 (2H, multiplet, NH, N—CH—CO); 6.22 (2H, multiplet, protons at the 3- and 4-positions of the furan ring); 6.84 [1H, singlet, CH(C$_6$H$_5$)$_2$]; 7.20, 7.27 [together 10H, each singlet, CH(C$_6$H$_5$)$_2$]; about 7.25 (1H, multiplet, proton at the 5-position of the furan ring); 7.55–7.95 (4H, multiplet, phthaloyl protons).

56(d)
2-(2-Furyl)-5-oxo-6-phthalimidoperhydro-1,4-thiazepine

To a solution of 7.6 g of the benzhydryl ester of S-[2-t-butoxycarbonylamino-1-(2-furyl)ethyl]-N-phthaloylcysteine [prepared as described in step (c) above] in 30 ml of anisole were added 30 ml of trifluoroacetic acid, whilst ice-cooling. The reaction mixture was changed to a brown color immediately, and was then stirred for 1.5 hours at room temperature. The reaction solution was then concentrated by evaporation under reduced pressure. The residue was dissolved in ethyl acetate, and 2 g of sodium bicarbonate and water were added to the solution and the mixture was stirred. The aqueous layer (at pH 7) was separated from the brownish ethyl acetate layer. The aqueous layer was adjusted to a pH value of 5.5 by adding 3N hydrochloric acid, and the solution was evaporated to dryness. The residue, containing S-[2-amino-1-(2-furyl)ethyl]-N-phthaloylcysteine, was suspended in 60 ml of dimethylformamide. To the suspension were added 2 ml of N-methylmorpholine and 5 g of diphenylphosphoryl azide. The mixture was stirred for 24 hours at room temperature. Water and ethyl acetate were added to the reaction mixture. The ethyl acetate layer was separated and dried over anhydrous magnesium sulfate, and the solvent was evaporated off to isolate the desired product as a crystalline powder. The product thus obtained was collected by filtration using a small amount of ethyl acetate and diethyl ether, to give the title compound, melting at 235° C., in a yield of 1.18 g.

Nuclear Magnetic Resonance Spectrum [(CD$_3$)$_2$SO] δ ppm: 3.26 (2H, broad doublet, J=6 Hz, N—CH$_2$—C); 3.5–4.35 (3H, multiplet, S—CH—furyl, N—CH—CH$_2$—S); 5.33 (1H, triplet, J=6 Hz, N—CH—CO); 6.33 (2H, multiplet, protons at the 3- and 4-positions of the furan ring); 7.50 (1H, multiplet, proton at the 5-position of the furan ring); 7.78 (4H, singlet, phthaloyl protons).

56(e) t-Butyl α-[2-(2-furyl)-5-oxo-6-phthalimidoperhydro-1,4-thiazepin-4-yl]acetate Following the procedure described in Example 42(f), 1.15 g of 2-(2-furyl)-5-oxo-6-phthalimidoperhydro-1,4-thiazepine [prepared as described in step (d) above] was treated with t-butyl bromoacetate, to give 0.86 g of the title compound as crystals, melting at 158°–161° C.

Nuclear Magnetic Resonance Spectrum (CDCl$_3$) δ ppm: 1.44 (9H, singlet, t-butyl); 2.9–4.6 (7H, multiplet, N—CH$_2$—CH(furyl)—S—CH$_2$, N—CH$_2$—CO); 5.58 (1H, doublet of doublets, J=4.5 & 8 Hz, —N—CH—CO); 6.33 (2H, multiplet, protons at the 3- and 4-positions of the furan ring); 7.37 (1H, multiplet, proton at the 5-position of the furan ring); 7.58–7.95 (4H, multiplet, phthaloyl protons).

56(f) t-Butyl α-[6-amino-2-(2-furyl)-5-oxoperhydro-1,4-thiazepin-4-yl]acetate Following the procedure described in Example 42(g), 0.85 g of t-butyl α-[2-(2-furyl)-5-oxo-6-phthalimidoperhydro-1,4-thiazepin-4-yl]acetate [prepared as described in step (e) above] was dephthaloylized by treatment with methylhydrazine, to afford a crude product, which was purified by silica gel column chromatography. From the fraction eluted with a 1:1:8 by volume mixture of methanol, cyclohexane and ethyl acetate was obtained 0.45 g of the title compound as crystals, melting at 90°–92° C.

Nuclear Magnetic Resonance Spectrum (CDCl$_3$) δ ppm: 1.48 (9H, singlet, t-butyl); 2.20 (2H, broad singlet, NH$_2$); 2.81 (2H, doublet, J=6 Hz, N—CH$_2$—C); 3.56–4.50 (6H, multiplet, —N—CH—CH$_2$—S—CH—furyl, N—CH$_2$—CO); 6.18–6.35 (2H, multiplet, protons at the 3- and 4-positions of the furan ring); 7.35 (1H, multiplet, proton at the 5-position of the furan ring).

56(g) t-Butyl α-[6-(1-ethoxycarbonyl-3-phenylpropylamino)-2-(2-furyl)-5-oxoperhydro-1,4-thiazepin-4-yl]acetate
(Compound No. 211)

Following the procedure described in Example 42(h), 0.40 g of t-butyl α-[6-amino-2-(2-furyl)-5-oxoperhydro-1,4-thiazepin-4-yl]acetate [prepared as described in step (f) above] was N-alkylated using 0.68 g of ethyl 2-bromo-4-phenylbutyrate. The resulting product was subjected to silica gel column chromatography eluted with a 1:20 by volume mixture of ethyl acetate and methylene chloride, to separate it into two isomers, A and B, (ascribed to the asymmetric carbon atom to which the phenethyl group is attached).

From the fraction initially eluted was obtained 0.30 g of isomer A as an oily substance.

Nuclear Magnetic Resonance Spectrum (CDCl$_3$) δ ppm: 1.22 (3H, triplet, J=7.5 Hz, CO$_2$CH$_2$CH$_3$); 1.46 (9H, singlet, t-butyl); 1.7–2.2 (2H, multiplet, PhCH$_2$CH$_2$); 2.4–4.5 (14H, multiplet, PhCH$_2$CH$_2$CH—NH—thiazepine ring protons, N—CH$_2$—CO, CO$_2$CH$_2$CH$_3$); 6.05–6.3 (2H, multiplet, protons at the 3- and 4-positions of furan ring); 7.13 (5H, singlet, phenyl protons); 7.25 (1H, multiplet, proton at the 5-position of the furan ring).

From the fraction eluted subsequently was obtained 0.30 g of isomer B as an oily substance.

Nuclear Magnetic Resonance Spectrum (CDCl$_3$) δ ppm: 1.26 (3H, triplet, J=7.5 Hz, CO$_2$CH$_2$CH$_3$); 1.48 (9H, singlet, t-butyl); 1.75–2.3 (2H, multiplet, PhCH$_2$CH$_2$); 2.5–4.5 (14H, multiplet, PhCH$_2$CH$_2$CH—NH—, thiazepine ring protons, N—CH$_2$—CO, CO$_2$CH$_2$CH$_3$); 6.1–6.35 (2H, multiplet, protons at the 3- and 4-positions of the furan ring); 7.15 (5H, singlet, phenyl protons); 7.27 (1H, multiplet, proton at the 5-position of the furan ring).

EXAMPLE 57

α-[6-(1-Ethoxycarbonyl-3-phenylpropylamino)-2-(2-furyl)-5-oxoperhydro-1,4-thiazepin-4-yl]acetic acid
(Compound No. 88)

Following the procedure described in Example 43, 270 mg of isomer B of t-butyl α-[6-(1-ethoxycarbonyl-3-phenylpropylamino)-2-(2-furyl)-5-oxoperhydro-1,4-thiazepin-4-yl]acetate [prepared as described in Example 56(g)] were de-t-butylated using trifluoroacetic acid, to afford 180 mg of the title compound as a powder.

Nuclear Magnetic Resonance Spectrum [(CD$_3$)$_2$SO] δ ppm: 1.26 (3H, triplet, J=7.5 Hz, CO$_2$CH$_2$CH$_3$); 1.9–2.3 (2H, multiplet, PhCH$_2$CH$_2$); 2.5–4.9 (13H, multiplet, PhCH$_2$CH$_2$CH—N, thiazepine ring protons, N—CH$_2$—CO, CO$_2$CH$_2$CH$_3$); 6.48 (2H, multiplet, protons at the 3- and 4-positions of the furan ring); 7.30 (5H, singlet, phenyl protons); 7.67 (1H, multiplet, proton at the 5-position of the furan ring).

EXAMPLE 58

α-[6-(1-Carboxy-3-phenylpropylamino)-2-(2-furyl)-5-oxoperhydro-1,4-thiazepin-4-yl]acetic acid (Compound No. 87)

Following the procedure described in Example 44, 130 mg of α-[6-(1-ethoxycarbonyl-3-phenylpropylamino)-2-(2-furyl)-5-oxoperhydro-1,4-thiazepin-4-yl]acetic acid (prepared as described in Example 57 above) were hydrolyzed with sodium hydroxide, to afford 87 mg of the title compound as a powder.

Nuclear Magnetic Resonance Spectrum [(CD$_3$)$_2$SO] δ ppm: 1.7–2.05 (2H, multiplet, PhCH$_2$CH$_2$); 2.5–4.7 (11H, multiplet, PhCH$_2$—CH$_2$CH—N, thiazepine ring protons, N—CH$_2$—CO); 6.42 (2H, multiplet at the 3- and 4-positions of the furan ring); 7.27 (5H, singlet, phenyl protons); 7.66 (1H, multiplet, proton at the 5-position of the furan ring).

EXAMPLE 59 t-Butyl α-[6-(1-butoxycarbonyl-3-phenylpropylamino)-2-(2-furyl)-5-oxoperhydro-1,4-thiazepin-4-yl]acetate (Compound No. 198)

Following the procedure described in Example 42(h), 0.30 g of t-butyl α-[6-amino-2-(2-furyl)-5-oxoperhydro-1,4-thiazepin-4-yl]acetate [obtained as described in Example 56(f)] was N-alkylated using 0.50 g of butyl 2-bromo-4-phenylbutyrate. The resulting product was subjected to silica gel column chromatography using a 1:40 by volume mixture of ethyl acetate and methylene chloride as eluent, to isolate two isomers, A and B, (ascribed to the asymmetric carbon atom, to which the phenethyl group is attached).

From the fraction initially eluted was obtained 0.15 g of isomer A as an oily substance.

Nuclear Magnetic Resonance Spectrum (CDCl$_3$) δ ppm: 0.7–1.1 (3H, multiplet, CH$_3$ of n-butyl); 1.47 (9H, singlet, t-butyl); 1.1–2.3 [6H, multiplet, CO$_2$CH$_2$(CH$_2$)$_2$CH$_3$, PhCH$_2$CH$_2$]; 2.3–4.5 [14H, multiplet, PhCH$_2$CH$_2$CH—NH, thiazepine ring protons, N—CH$_2$—CO, CO$_2$CH$_2$(CH$_2$)$_2$CH$_3$]; 6.05–6.3 (2H, multiplet, protons at the 3- and 4-positions of the furan ring); 7.14 (5H, singlet, phenyl protons); 7.25 (1H, multiplet, proton at the 5-position of the furan ring).

From the fraction eluted subsequently was obtained 0.15 g of Isomer B as an oily substance.

Nuclear Magnetic Resonance Spectrum (CDCl$_3$) δ ppm: 0.7–1.1 (3H, multiplet, CH$_3$ of n-butyl); 1.46 (9H, singlet, t-butyl); 1.1–2.3 [6H, multiplet, CO$_2$CH$_2$(CH$_2$)$_2$CH$_3$, PhCH$_2$CH$_2$]; 2.3–4.5 [14H, m, PhCH$_2$CH$_2$CH—NH-, thiazepine ring protons, N—CH$_2$—CO, CO$_2$CH$_2$(CH$_2$)$_2$CH$_3$]; 6.05–6.3 (2H, multiplet, protons at the 3- and 4-positions of the furan ring); 7.15 (5H, singlet, phenyl protons); 7.25 (1H, multiplet, proton at the 5-position of the furan ring).

EXAMPLE 60

α-[6-(1-Butoxycarbonyl-3-phenylpropylamino)-2-(2-furyl)-5-oxoperhydro-1,4-thiazepin-4-yl]acetic acid (Compound No. 89)

Following the procedure described in Example 43, 0.15 g of isomer B of t-butyl α-[6-(1-butoxycarbonyl-3-phenylpropylamino)-2-(2-furyl)-5-oxoperhydro-1,4-thiazepin-4-yl]acetate (obtained as described in Example 59) was de-t-butyrated using trifluoroacetic acid, to afford 95 mg of the title compound as a powder.

Nuclear Magnetic Resonance Spectrum (CDCl$_3$) δ ppm: 0.7–1.1 (3H, multiplet, CH$_3$ of n-butyl); 1.1–2.3 [6H, multiplet, CO$_2$CH$_2$(CH$_2$)$_2$CH$_3$, PhCH$_2$CH$_2$]; 2.4–4.6 [13H, multiplet, PhCH$_2$CH$_2$CH—N, thiazepine ring protons, N—CH$_2$—CO, CO$_2$CH$_2$(CH$_2$)$_2$CH$_3$]; 6.05–6.3 (2H, multiplet, protons at the 3- and 4-positions of the furan ring); 7.16 (5H, singlet, phenyl protons); 7.25 (1H, multiplet, proton at the 5-position of the furan ring).

EXAMPLE 61 t-Butyl α-[6-(1-benzyloxycarbonyl-3-phenylpropylamino)-2-(2-furyl)-5-oxoperhydro-1,4-thiazepin-4-yl]acetate (Compound No. 212)

Following the procedure described in Example 42(h), 0.30 g of t-butyl α-[6-amino-2-(2-furyl)-5-oxoperhydro-1,4-thiazepin-4-yl]acetate [obtained as described in Example 56(f)] was N-alkylated using 0.60 g of benzyl 2-bromo-4-phenylbutyrate. The resulting product was subjected to silica gel column chromatography, using a 1:40 by volume mixture of ethyl acetate and methylene chloride as eluent, to separate it into two isomers, A and B, (ascribed to the asymmetric carbon atom to which the phenethyl group is attached).

From the fraction initially eluted was obtained 0.14 g of Isomer A as an oily substance.

Nuclear Magnetic Resonance Spectrum (CDCl$_3$) δ ppm: 1.46 (9H, singlet, t-butyl); 1.7–2.2 (2H, multiplet, PhCH$_2$CH$_2$); 2.3–4.6 (12H, multiplet, PhCH$_2$CH$_2$CH—NH, thiazepine ring protons, N—CH$_2$—CO); 5.06 (2H, AB quartet, Δδ=0.21 ppm, J=13 Hz, CH$_2$Ph); 6.05–6.3 (2H, multiplet, protons at the 3- and 4-positions of the furan ring); 7.10, 7.27 (together 10H, each singlet, protons of the 2 phenyl groups); about 7.25 (1H, multiplet, proton at the 5-position of the furan ring).

From the fraction eluted subsequently was obtained 0.15 g of Isomer B as an oily substance.

Nuclear Magnetic Resonance Spectrum (CDCl$_3$) δ ppm: 1.46 (9H, singlet, t-butyl); 1.75–2.2 (2H, multiplet, PhCH$_2$CH$_2$); 2.4–4.5 (12H, multiplet, PhCH$_2$CH$_2$CH—NH, thiazepine ring protons, N—CH$_2$CO); 5.08 (2H, singlet, CH$_2$Ph); 6.05–6.3 (2H; multiplet, protons at the 3- and 4-positions of furan ring); 7.11, 7.27 (together 10H, each singlet, protons of the 2 phenyl groups); about 7.25 (1H, multiplet, proton at the 5-position of the furan ring).

EXAMPLE 62

α-6-(1-Benzyloxycarbonyl-3-phenylpropylamino)-2-(2-furyl)-5-oxoperhydro-1,4-thiazepin-4-yl]acetic acid (Compound No. 91)

Following the procedure described in Example 43, 0.15 g of isomer B of t-butyl α-[6-(1-benzyloxycarbonyl-3-phenylpropylamino)-2-(2-furyl)-5-oxoperhydro-1,4-thiazepin-4-yl]acetate (obtained as described in Example 61) was de-t-butyrated by treatment with trifluoroacetic acid, to afford 90 mg of the title compound as a powder.

Nuclear Magnetic Resonance Spectrum (CDCl$_3$) δ ppm: 1.8–2.3 (2H, multiplet, PhCH$_2$CH$_2$); 2.4–4.5 (11H, multiplet, PhCH$_2$CH$_2$CH—N, thiazepine ring protons, N—CH$_2$—CO); 5.15 (2H, singlet, CH$_2$Ph$_2$); 6.05–6.3 (2H, multiplet, protons at the 3- and 4-positions of the furan ring); 7.13, 7.32 (together 10H, each singlet, protons of the 2 phenyl groups); about 7.25 (1H, multiplet, proton at the 5-position of furan ring).

EXAMPLE 63 t-Butyl α-{6(R)-[1(S)-ethoxycarbonyl-3-phenylpropylamino]-5-oxo-2-(2-thienyl)perhydro-1,4-thiazepin-4-yl}acetate (Compound No. 119)

63(a)
N-t-butoxycarbonyl-S-[2-nitro-1-(2-thienyl)ethyl]-L-cysteine 100 g of L-cysteine p-toluenesulfonate, 85.3 g of di-t-butyl pyrocarbonate and 85.3 g of sodium bicarbonate were dissolved in a mixture of 683 ml of dimethylformamide and 137 ml of water. The solution was stirred for 2 hours at 60° C. under a stream of nitrogen. The resulting reaction mixture was then cooled to a temperature of 10°–15° C., and 55 g of 1-nitro-2-(2-thienyl)ethylene and 10.2 g of sodium bicarbonate were added, after which the mixture was stirred for 2 hours at room temperature. At the end of this time, 2 liters of water and 0.8 liter of ethyl acetate were added, with stirring, and the aqueous layer was separated and washed with ethyl acetate. To the washed solution were added ethyl acetate and ice, and the pH of this mixture was adjusted to a value of 3 by carefully adding concentrated hydrochloric acid, whilst stirring. The ethyl acetate layer was then separated and washed with an aqueous solution of sodium chloride; active carbon and anhydrous magnesium sulfate were added, with stirring, and then filtered off. The solvent was evaporated from the organic solution to give 129 g of the title compound as a syrup. This compound was used in the reaction of step (b) without further purification.

Nuclear Magnetic Resonance Spectrum (CDCl$_3$) δ ppm: 1.46 (9H, singlet, t-butyl); 2.7–3.1 (2H, multiplet, C—C$\underline{H_2}$—S); 4.2–5.7 (5H, multiplet, NH—C$\underline{H}$—CO, S—C$\underline{H}$—C$\underline{H_2}$—NO$_2$); 6.75–7.05 (2H, multiplet, protons at the 3 and 4-positions on the thiophene ring); 7.1–7.3 (1H, multiplet, proton at the 5-position on the thiophene ring).

63(b)
S-[2-Amino-1-(2-thienyl)ethyl]-N-t-butoxycarbonyl-L-cysteine 129 g of N-t-butoxycarbonyl-S-[2-nitro-1-(2-thienyl)ethyl]-L-cysteine [produced as described in step (a) above] were dissolved in 1 liter of acetic acid. To the solution were added 100 g of 10% w/w palladium-on-carbon, and the mixture was shaken for 5 hours at 70° C. in an atmosphere containing hydrogen at a partial pressure of 3–4 kg/cm$^2$. The palladium-on-carbon catalyst was then filtered off, and the filtrate was condensed by evaporation under reduced pressure. The remaining acetic acid was then distilled off as an azeotrope with toluene. The residue was dissolved in a mixture of 500 ml of ethyl acetate and 100 ml of water, and the pH of the aqueous layer was adjusted to a value of 6.1, by adding sodium bicarbonate powder, whilst stirring. The organic layer was then separated, and the aqueous layer was extracted with a mixture of ethyl acetate and methylene chloride. The separated organic layer and the extract were combined and the mixture was dried over anhydrous magnesium sulfate, after which the solvent was distilled off. The gummy residue was solidified by the addition of diethyl ether and then recovered by filtration, giving 97.1 g of the title compound as a powder. This compound was used in the reaction of step (c) without any further purification.

Nuclear Magnetic Resonance Spectrum [(CD$_3$)$_2$SO] δ ppm: 1.37 (9H, singlet, t-butyl); 2.6–3.5 (4H, multiplet, C—C$\underline{H_2}$—S, C—C$\underline{H_2}$—NH$_2$); 3.9 (1H, multiplet, S—C$\underline{H}$—thienyl); 4.5 (1H, multiplet, NH—C$\underline{H}$—CO); 6.2 (1$\underline{H}$, multiplet, N$\underline{H}$); 6.8–7.1 (2H, multiplet, protons at the 3 and 4-positions on the thiophene ring); 7.42 (1H, multiplet, proton at the 5-position on the thiophene ring).

63(c)
6(R)-t-Butoxycarbonylamino-5-oxo-2-(2-thienyl)perhydro-1,4-thiazepine

A solution of 150 g of S-[2-amino-1-(2-thienyl)ethyl]-N-t-butoxycarbonyl-L-cysteine [prepared as described in step (b) above] and 52 ml of N-methylmorpholine in 1 liter of dimethylformamide was added to a solution of 108.4 ml of diphenylphosphoryl azide in 500 ml of dimethylformamide at 10° C., over a period of 4 hours, and the mixture was left to stand at room temperature overnight. At the end of this time, 1.5 liters of ethyl acetate and 1.5 liters of water were added, and the organic layer was separated. The aqueous layer was extracted twice with ethyl acetate, and the resulting extracts were combined with the separated organic layer. The resulting organic mixture was washed twice, each time with an aqueous solution of sodium chloride, and then dried over anhydrous magnesium sulfate, after which the solvent was evaporated off. The residue was subjected to silica gel column chromatography, using a 1:4 by volume mixture of ethyl acetate and methylene chloride as eluent, to give 112.5 g of the title compound as a gummy substance.

Nuclear Magnetic Resonance Spectrum (CDCl$_3$) δ ppm: 1.45 (9H, singlet, t-butyl); 2.9 (2H, multiplet, C—C$\underline{H_2}$—S); 3.6–4.4 (3H, multiplet, S—C$\underline{H}$—CH$_2$—N); 4.85 (1H, multiplet, N—C$\underline{H}$—CO); 5.99 (1$\underline{H}$, doublet, J=5 Hz, butoxycarbonyl-N$\underline{H}$); 6.8–7.3 (3H, multiplet, protons on thiophene ring); 7.3 (1H, multiplet, thiazepine NH).

63(d)
6(R)-Amino-5-oxo-2-(2-thienyl)perhydro-1,4-thiazepine 319 ml of a 4N solution of hydrogen chloride in dioxane were added to 102 g of 6(R)-t-butoxycarbonylamino-5-oxo-2-(2-thienyl)perhydro-1,4-thiazepine [prepared as described in step (c) above], and the mixture was stirred for 1 hour, with ice-cooling. 500 ml of diethyl ether were then added and the resulting crystals (a yield of 82.3 g) were collected. These crystals were suspended in a mixture of 2 liters of methylene chloride and 0.1 liter of methanol, and a solution of 70 g of potassium carbonate in 200 ml of water was added to the suspension, and the mixture was then stirred for 2 hours. The resulting precipitate was filtered off, and the organic layer was separated from the aqueous layer. The precipitate was dissolved in 200 ml of water, and this solution was combined with the aqueous layer; the mixture was extracted twice, each time with 220 ml of 10% v/v methanol in methylene chloride. The organic layer and the extracts were combined and dried over anhydrous magnesium sulfate, after which sufficient solvent was evaporated off to reduce the volume to about 300 ml. 500 ml of ethyl acetate were added to the residue, and then sufficient of the solvent was evaporated off to reduce the volume to about 400 ml. The residue was left standing at room temperature overnight, and then the precipitated crystals were collected by filtration, to give 19.1 of the title compound, melting at 157° C.

$[\alpha]^{23} + 51.5°$ (c=1.36, dimethylformamide).

Nuclear Magnetic Resonance Spectrum [(CD$_3$)$_2$SO] δ ppm: 2.21 (2H, broad singlet, NH$_2$); 2.6–2.9 (2H, multiplet, C—CH$_2$—S); 3.4–4.4 (4H, multiplet, NH$_2$—CH—CO, S—CH—CH$_2$—N); 6.8 (2H, multiplet, protons at the 3 and 4-positions on the thiophene ring); 7.40 (1H, doublet of doublets, J=1.5 & 4.5 Hz, proton at the 5-position of the thiophene ring); 7.83 (1H, broad triplet, J=7 Hz, CONH).

63(e)
5-Oxo-6(R)-phthalimido-2-(2-thienyl)perhydro-1,4-thiazepine 19.1 g of 6(R)-amino-5-oxo-2-(2-thienyl)perhydro-1,4-thiazepine [prepared as described in step (d) above], 18 g of N-ethoxycarbonylphthalimide and 29 g of sodium bicarbonate were suspended in 150 ml of dimethylformamide. The suspension was stirred for 7 hours at 60° C. and then left standing overnight at room temperature. At the end of this time, 500 ml of water, 100 ml of diisopropyl ether and 20 ml of ethyl acetate were added, and the mixture was stirred to precipitate the title compound. This was collected by filtration, and washed with water and with a 5:1 by volume mixture of diisopropyl ether and ethyl acetate, giving 27.4 of the title compound, melting at 246°–247.5° C. (with coloration).

$[\alpha]^{23} + 41°$ (c=1.36, dimethylformamide).

The nuclear magnetic resonance spectrum of this compound was identical with that of the compound produced as described in Example 49(e).

63(f) t-Butyl α-[5-oxo-6(R)-phthalimido-2-(2-thienyl)perhydro-1,4-thiazepin-4-yl]acetate The procedure described in Example 42(f) was repeated, except that 33.8 g of 5-oxo-6(R)-phthalimido-2-(2-thienyl)perhydro-1,4-thiazepine [prepared as described in step (e) above] were used as the starting material and that the compound was purified by silica gel column chromatography using a 1:2 by volume mixture of ethyl acetate and cyclohexane as the eluent, to give 34.8 g of the title compound melting at 151°–152.5° C.

$[\alpha]^{23} + 92°$ (c=1.55, dimethylformamide).

The nuclear magnetic resonance spectrum of this compound was identical to that of the compound synthesized as described in Example 49(f).

63(g) t-Butyl α-[6(R)-amino-5-oxo-2-(2-thienyl)perhydro-1,4-thiazepin-4-yl]acetate 7 ml of hydrazine hydrate were added to a suspension of 34.1 g of t-butyl α-[5-oxo-6(R)-phthalimido-2-(2-thienyl)perhydro-1,4-thiazepin-4-yl]acetate [prepared as described in step (f) above] in 340 ml of methanol, to form a homogeneous solution. This was left standing for 2 days at room temperature, and then the resulting precipitate was filtered off. The filtrate was condensed by evaporation under reduced pressure, and then 200 ml of methylene chloride were added to the residue. The mixture was stirred and insoluble matter was filtered off. The filtrate was washed with water and dried over anhydrous magnesium sulfate, after which the solvent was evaporated off. The residue was crystallized by adding diisopropyl ether containing a small amount of hexane, to yield 22.3 g of the title compound, melting at 81°–82° C.

$[\alpha]^{23} + 68°$ (c=1.2, dimethylformamide).

The nuclear magnetic resonance spectrum of this product was identical with that of the product of Example 49(g).

63(h) t-Butyl α-{6(R)-[1(S)-ethoxycarbonyl-3-phenylpropylamino]-5-oxo-2-(2-thienyl)perhydro-1,4-thiazepin-4-yl}acetate (Compound No. 119)

A solution of 4.0 g of ethyl 4-phenyl-2-(R)-trifluoromethanesulfonyloxybutyrate in 15 ml of methylene chloride was added dropwise to a solution of 4.0 g of t-butyl α-[6(R)-amino-5-oxo-2-(2-thienyl)perhydro-1,4-thiazepin-4-yl]acetate [prepared as described in step (g) above] and 1.62 ml of triethylamine in 50 ml of methylene chloride. The reaction mixture was stirred for 2 hours at room temperature, after which it was washed with water and dried over anhydrous magnesium sulfate; the solvent was then evaporated off under reduced pressure. The residue was purified by silica gel column chromatography, using a 20:1 by volume mixture of methylene chloride and ethyl acetate as the eluent, to give 5.5 g of the title compound in the form of a syrup.

$[\alpha]^{23} + 40°$ (c=1.2, dimethylformamide).

The nuclear magnetic resonance spectrum of this product was identical with that of the product (Isomer B) produced as described in Example 49(h).

EXAMPLE 64
α-{6(R)-[1(S)-Ethoxycarbonyl-3-phenylpropylamino]-5-oxo-2-(2-thienyl)perhydro-1,4-thiazepin-4-yl}acetic acid (Compound No. 78)

The procedure described in Example 43 was repeated, except that 2.81 g of t-butyl α-{6(R)-[1(S)-ethoxycarbonyl-3-phenylpropylamino]-5-oxo-2-(2-thienyl)perhydro-1,4-thiazepin-4-yl}acetate [produced as described in Example 63(h)] were employed as the starting material, to give 2.30 g of the title compound in the form of a powder.

$[\alpha]^{23} + 40°$ (c=1.1, dimethylformamide).

The nuclear magnetic resonance spectrum of this product was identical with that of the product of Example 50.

EXAMPLE 65
α-{6(R)-[1(S)-Ethoxycarbonyl-3-phenylpropylamino]-5-oxo-2-(2-thienyl)perhydro-1,4-thiazepin-4-yl}acetic acid hydrochloride (hydrochloride of Compound No. 78)

0.70 g of α-{6(R)-[1(S)-ethoxycarbonyl-3-phenylpropylamino]-5-oxo-2-(2-thienyl)perhydro-1,4-thiazepin-4-yl}acetic acid (prepared as described in Example 64) was dissolved in 20 ml of ethyl acetate. 0.7 ml of a 4N solution of hydrogen chloride in dioxane was then added, and the mixture was stirred. The mixture was then condensed by evaporation under reduced pressure, and the residue was dissolved in a small amount of ethyl acetate. Diethyl ether was added drop by drop to crystallize the product, and the resulting crystals were collected by filtration, giving 0.62 g of the title compound, melting at 179°–181° C.

$[\alpha]^{23} + 45°$ (c=1.27, dimethylformamide).

EXAMPLE 66

α-{6(R)-[1(S)-Carboxy-3-phenylpropylamino]-5-oxo-2-(2-thienyl)perhydro-1,4-thiazepin-4-yl}acetic acid (Compound No. 77)

The procedure described in Example 44 was repeated, except that 80 mg of α-{6(R)-[1(S)-ethoxycarbonyl-3-phenylpropylamino]-5-oxo-2-(2-thienyl)perhydro-1,4-thiazepin-4-yl}acetic acid (prepared as described in Example 64) were used as the starting material. After hydrolysis of the starting material with sodium hydroxide, 65 mg of the title compound were obtained as a powder.

$[\alpha]^{23} + 56°$ (c = 1.27, dimethylformamide).

The nuclear magnetic resonance spectrum of this compound was identical with that of the compound prepared as described in Example 51.

EXAMPLE 67 t-Butyl α-{6(R)-[1(S)-ethoxycarbonyl-3-phenylpropylamino]-5-oxo-2-(3-thienyl)perhydro-1,4-thiazepin-4-yl}acetate (Compound No. 120)

67(a)

N-t-butoxycarbonyl-S-[2-nitro-1-(3-thienyl)ethyl]-L-cysteine

N-t-butoxycarbonyl-L-cysteine [prepared from 58.6 g of L-cysteine p-toluenesulfonate, 50 g of di-t-butyl pyrocarbonate and 50 g of sodium bicarbonate in the manner described in Example 63(a)] was treated with 32 g of 1-nitro-2-(3-thienyl)ethylene and 6 g of sodium bicarbonate to give 74.8 g of the title compound as a syrup.

Nuclear Magnetic Resonance Spectrum (CDCl$_3$) δ ppm: 1.44 (9H, singlet, t-butyl); 2.9 (2H, broad doublet, J=5 Hz, C—CH$_2$—S); 4.1–5.6 (5H, multiplet, —NH—CH—CO, S—CH—CH$_2$—NO$_2$); 6.9–7.4 (3H, multiplet, protons on thiophene ring).

67(b)

S-[2-Amino-1-(3-thienyl)ethyl]-N-t-butoxycarbonyl-L-cysteine 74.8 g of N-t-butoxycarbonyl-S-[2-nitro-1-(3-thienyl)ethyl]-L-cysteine were reduced with hydrogen in the presence of 10% w/w palladium-on-carbon, as described in Example 63(b), to give 50.4 g of the title compound as a powder.

Nuclear Magnetic Resonance Spectrum [(CD$_3$)$_2$SO] δ ppm: 1.40 (9H, singlet, t-butyl); 2.6–3.5 (4H, multiplet, C—CH$_2$—S, C—CH$_2$—NH$_2$); 3.9 (1H, multiplet, S—CH—thienyl); 4.3 (1H, multiplet, NH—CH—CO); 6.2 (1H, multiplet, NH); 7.0–7.6 (3H, multiplet, protons on thiophene ring).

67(c)

6(R)-t-Butoxycarbonylamino-5-oxo-2-(3-thienyl)perhydro-1,4-thiazepine 69.2 g of S-[2-amino-1-(3-thienyl)ethyl]-N-t-butoxycarbonyl-L-cysteine [prepared as described in step (b) above] were cyclized following the procedure described in Example 63(c), to give 39.9 g of the title compound.

Nuclear Magnetic Resonance Spectrum (CDCl$_3$) δ ppm: 1.46 (9H, singlet, t-butyl); 2.6–3.0 (2H, multiplet, C—CH$_2$—S); 3.5–4.2 (3H, multiplet, S—CH—CH$_2$—N); 4.8 (1H, multiplet, N—CH—CO); 5.95 (1H, broad doublet, J=5 Hz, t-butoxycarbonyl-NH); 6.9–7.35 (3H, multiplet, protons on thiophene ring).

67(d)

6(R)-Amino-5-oxo-2-(3-thienyl)perhydro-1,4-thiazepine 16.4 g of 6(R)-t-butoxycarbonylamino-5-oxo-2-(3-thienyl)perhydro-1,4-thiazepine [prepared as described in step (c) above] were treated as described in Example 63(d), to give 5.4 g of the title compound as crystals melting at 190°–191° C.

$[\alpha]^{23} + 36°$ (c = 1.3, dimethylformamide).

Nuclear Magnetic Resonance Spectrum [CDCl$_3$ + sufficient (CD$_3$)$_2$SO to dissolve the test compound] δ ppm: 2.6–3.1 (4H, multiplet, NH$_2$, C—CH$_2$—S); 3.4–4.3 (4H, multiplet, NH$_2$—CH—CO, S—CH—CH$_2$—N); 7.1 (1H, multiplet, 4-position proton on thiophene ring); 7.35 (2H, multiplet, 2 and 5-position protons on thiophene ring); 7.76 (1H, broad, CONH).

67(e)

5-Oxo-6(R)-phthalimido-2-(3-thienyl)perhydro-1,4-thiazepine 15.6 g or 6(R)-amino-5-oxo-2-(3-thienyl)perhydro-1,4-thiazepine [prepared as described in step (d) above] were treated as described in Example 63(e), to give 16.9 g of the title compound, melting at 243°–245° C. (with coloration).

$[\alpha]^{23} + 55°$ (c = 1.1, dimethylformamide).

The nuclear magnetic resonance spectrum of this product was identical with that of the product produced as described in Example 42(e).

67(f) t-Butyl α-[5-oxo-6(R)-phthalimido-2-(3-thienyl)perhydro-1,4-thiazepin-4-yl]acetate 16 g of 5-oxo-6(R)-phthalimido-2-(3-thienyl)perhydro-1,4-thiazepine [prepared as described in step (e) above] were treated as described in Example 42(f), to give the title compound, which was purified by means of silica gel column chromatography, using a 2:1 by volume mixture of cyclohexane and ethyl acetate as the eluent, to give 15.6 g of an amorphous solid.

$[\alpha]^{23} + 102°$ (c = 1.3, dimethylformamide).

The nuclear magnetic resonance spectrum of this product was identical with that of the product of Example 42(f).

67(g) t-Butyl α-[6(R)-amino-5-oxo-2-(3-thienyl)perhydro-1,4-thiazepin-4-yl]acetate 11.7 g of t-butyl α-[5-oxo-6(R)-phthalimido-2-(3-thienyl)perhydro-1,4-thiazepin-4-yl]acetate [prepared as described in step (f) above] were treated as described in Example 63(g), to give 7.7 g of the title compound as a powder.

$[\alpha]^{23} + 82°$ (c = 1.3, dimethylformamide).

The nuclear magnetic resonance spectrum of this product was identical to that of the product of Example 42(g).

67(h) t-Butyl α-{6(R)-[1(S)-ethoxycarbonyl-3-phenylpropylamino]-5-oxo-2-(3-thienyl)perhydro-1,4-thiazepin-4-yl}acetate (Compound No. 120)

6.7 g of t-butyl α-[6(R)-amino-5-oxo-2-(3-thienyl)perhydro-1,4-thiazepin-4-yl]acetate [prepared as described in step (g) above] were treated as described in Example 63(h), to give 7.6 g of the title compound as a gum.
$[\alpha]^{23} +39°$ (c=1.25, dimethylformamide).

The nuclear magnetic resonance spectrum of this product was identical to that of the product (Isomer B) of Example 42(h).

EXAMPLE 68

α-{6(R)-[1(S)-Ethoxycarbonyl-3-phenylpropylamino]-5-oxo-2-(3-thienyl)perhydro-1,4-thiazepin-4-yl}acetic acid (Compound No. 83)

3.74 g of t-butyl α-{6(R)-[1(S)-ethoxycarbonyl-3-phenylpropylamino]-5-oxo-2-(3-thienyl)perhydro-1,4-thiazepin-4-yl}acetate were treated as described in Example 43, to give 3.24 g of the title compound as a powder.
$[\alpha]^{23} +43°$ (c=1.43, dimethylformamide).

The nuclear magnetic resonance spectrum of this product was identical with that of the product produced as described in Example 43.

EXAMPLE 69

α-{6(R)-[1(S)-Ethoxycarbonyl-3-phenylpropylamino]-5-oxo-2-(3-thienyl)perhydro-1,4-thiazepin-4-yl}acetic acid hydrochloride (hydrochloride of Compound No. 83)

0.8 g of α-{6(R)-[1(S)-ethoxycarbonyl-3-phenylpropylamino]-5-oxo-2-(3-thienyl)perhydro-1,4-thiazepin-4-yl}acetic acid (produced as described in Example 68) was converted to its hydrochloride salt, following the procedure described in Example 65, giving 0.68 g of the title compound, melting at 178°–180° C.
$[\alpha]^{23} +47°$ (c=1.3, dimethylformamide).

EXAMPLE 70

α-{6(R)-[1(S)-Carboxy-3-phenylpropylamino]-5-oxo-2-(3-thienyl)perhydro-1,4-thiazepin-4-yl}acetic acid (Compound No. 82)

70 mg of α-{6(R)-[1(S-ethoxycarbonyl-3-phenylpropylamino]-5-oxo-2-(3-thienyl)perhydro-1,4-thiazepin-4-yl}acetic acid (produced as described in Example 68) were hydrolyzed with aqueous sodium hydroxide, as described in Example 44, to give 60 mg of the title compound as a powder.
$[\alpha]^{23} +61.6°$ (c=1.2, dimethylformamide).

The nuclear magnetic resonance spectrum of this compound was identical with that of the compound produced as described in Example 44.

We claim:

1. A compound of formula (Ia):

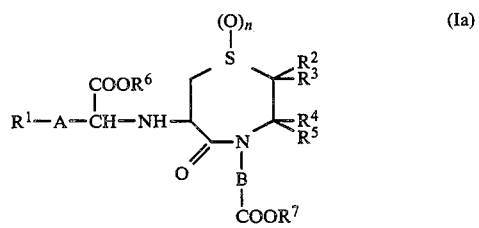

wherein
$R^1$ is selected from the group consisting of $C_1$-$C_{10}$ alkyl groups, $C_3$-$C_8$ cycloalkyl groups, carbocyclic aryl groups having 6 or 10 ring carbon atoms, partially hydrogenated carbocyclic aryl groups having 6 or 10 ring carbon atoms, and heterocyclic groups (i) selected from the group consisting of thiazolyl, imidazolyl, oxazolyl, isoxazolyl, furyl and thienyl, said groups $R^1$ being unsubstituted or having at least one substituent selected from the group consisting of (a) oxo groups, $C_1$-$C_6$ alkyl groups, $C_6$ or $C_{10}$ carbocyclic aryl groups, aralkyl groups wherein the alkyl part is $C_1$-$C_6$ alkyl and the aryl part is $C_6$ or $C_{10}$ carbocyclic aryl, hydroxy groups, $C_1$-$C_6$ alkoxy groups, alkoxyalkoxy groups where each alkoxy part is $C_1$-$C_6$, aralkyloxy groups, wherein the alkoxy part is $C_1$-$C_6$ alkoxy and the aryl part is $C_6$ or $C_{10}$ carbocyclic aryl, aryloxy groups wherein the aryl part is $C_6$ or $C_{10}$ carbocyclic aryl, halogen atoms, nitro groups, cyano groups, carboxy groups, alkoxycarbonyl groups wherein the alkoxy part is $C_1$-$C_6$ alkoxy, amino groups, $C_1$-$C_6$ alkylamino groups, dialkylamino groups wherein each alkyl part is $C_1$-$C_6$ alkyl, $C_1$-$C_7$ aliphatic or carbocyclic $C_6$ or $C_{10}$ aryl carboxylic acylamino groups, carbamoyl groups, alkylcarbamoyl groups where the alkyl part is $C_1$-$C_6$ alkyl, dialkylcarbamoyl groups where each alkyl part is $C_1$-$C_6$ alkyl, $C_1$-$C_6$ alkylthio groups, $C_6$ or $C_{10}$ carbocyclic arylthio groups, $C_1$-$C_6$ alkylsulfonyl groups and $C_6$ or $C_{10}$ carbocyclic arylsulfonyl groups wherein the aryl part is unsubstituted or has from 1 to 3 $C_1$-$C_6$ alkyl substituents;

$R^2$, $R^3$, $R^4$ and $R^5$ are independently selected from the group consisting of hydrogen atoms, $C_1$-$C_{10}$ alkyl groups, $C_3$-$C_8$ cycloalkyl groups, aralkyl groups wherein the alkyl part is $C_1$-$C_6$ alkyl and the aryl part is $C_6$ or $C_{10}$ carbocyclic aryl, $C_6$ or $C_{10}$ carboxylic aryl groups, heterocyclic groups (ii) selected from the group consisting of tetrahydrofuranyl, tetrahydrothienyl, tetrahydropyranyl, morpholinyl, furyl, thienyl, imidazolyl, thiazolyl, oxazolyl, isoxazolyl, 1,3,4-oxadiazolyl, 1,3,4-thiadiazolyl, pyridyl, quinolyl, isoquinolyl and indolyl, and heterocyclic substituted $C_1$-$C_6$ alkyl groups having a heterocyclic substituent selected from said heterocyclic groups (ii); provided that $R^2$, $R^3$, $R^4$ and $R^5$ are not all hydrogen atoms, said groups represented by $R^2$, $R^3$, $R^4$ and $R^5$ being unsubstituted or having at least one substituent selected from the group consisting of the substituents defined in (a) above, or each of $R^2$ and $R^3$, $R^4$ and $R^5$ or $R^2$ and $R^4$ are selected from the group consisting of cyclopropane, cyclopentane, cyclohexane, tetrahydrofuran, tetrahydropyran, tetrahydrothiphene, pyrrolidine, piperidine, indane and 1,2,3,4-tetrahydronaphthalene;

$R^6$ is selected from the group consisting of hydrogen, $C_1$-$C_{10}$ alkyl, and aralkyls which are $C_6$ or $C_{10}$ aryl-$C_1$-$C_6$ alkyl;

$R^7$ is selected from the group consisting of hydrogen, ($C_1$-$C_4$ alkoxy)carbonyloxy($C_1$-$C_4$ alkyl), ($C_2$-$C_5$ alkanoyl)oxy($C_1$-$C_4$ alkyl), (5-alkyl-2-oxo-1,3-dioxolen-4-yl)alkyls in which each alkyl group has from 1 to 4 carbon atoms, (5-phenyl-2-oxo-1,3-dioxolen-4-yl)alkyls in which the alkyl part has from 1 to 4 carbon atoms, and phthalidyl;

A is a direct carbon-carbon bond, a methylene group, an ethylene group, an oxymethyl group or a thiomethyl group;

B is a $C_1$-$C_4$ alkylene or alkylidene group or a $C_3$-$C_6$ cycloalkylene or cycloalkylidene group;

n is 0, 1 or 2; and pharmaceutically acceptable salts thereof.

2. A compound as claimed in claim 1, in which:
$R^1$ represents a phenyl group or a $C_2$–$C_7$ alkyl group;
$R^2$ and $R^4$ are the same or different and each represents a hydrogen atom, a $C_1$–$C_{10}$ alkyl group, a phenyl group, a naphthyl group, a $C_3$–$C_8$ cycloalkyl group or a heterocyclic group (ii);
$R^3$ and $R^5$ both represent hydrogen atoms;
A represents an ethylene group;
B represents a methylene group; and
n is 0.

3. A compound as claimed in claim 2, in which: $R^2$ and $R^4$ are the same or different and each represents a hydrogen atom, a $C_1$–$C_{10}$ alkyl group, a phenyl group, a naphthyl group, a $C_3$–$C_8$ cycloalkyl group or a heterocyclic group having 5 or 6 ring atoms.

4. A compound as claimed in claim 1, in which:
$R^1$ represents a phenyl group or a $C_2$–$C_7$ alkyl group;
$R^2$ represents a $C_1$–$C_{10}$ alkyl group, a phenyl group, a naphthyl group, a $C_3$–$C_8$ cycloalkyl group or a heterocyclic group (ii) having 5 or 6 ring atoms;
$R^3$, $R^4$ and $R^5$ all represent hydrogen atoms;
A represents an ethylene group;
B represents a methylene group; and
n is 0.

5. A compound as claimed in claim 1, in which:
$R^1$ represents a phenyl group or a $C_2$–$C_7$ alkyl groups;
$R^2$ represents a heterocyclic group (ii) having 5 or 6 ring atoms;
$R^3$, $R^4$ and $R^5$ all represent hydrogen atoms;
$R^6$ represents a hydrogen atom, a $C_1$–$C_6$ alkyl group or an aralkyl group of which the aryl part is a $C_6$ or $C_{10}$ carbocyclic aryl group and the alkyl part is a $C_1$–$C_4$ alkyl group;
A represents an ethylene group;
B represents a methylene group; and
n is 0.

6. A compound as claimed in claim 1, in which:
$R^1$ represents a phenyl group or a $C_2$–$C_7$ alkyl group;
$R^2$ represents a heterocyclic group (ii) having 5 ring atoms;
$R^3$, $R^4$ and $R^5$ all represent hydrogen atoms;
$R^6$ represents a hydrogen atom, a $C_1$–$C_6$ alkyl group or an aralkyl group of which the aryl part is a $C_6$ or $C_{10}$ carbocyclic aryl group and the alkyl part is a $C_1$–$C_4$ alkyl group;
A represents an ethylene group;
B represents a methylene group; and
n is 0.

7. A compound as claimed in claim 1, in which:
$R^1$ represents a phenyl group or a $C_2$–$C_7$ alkyl group;
$R^2$ represents a thienyl group or furyl group;
$R^3$, $R^4$ and $R^5$ all represent hydrogen atoms;
$R^6$ represents a hydrogen atom, a $C_1$–$C_4$ alkyl group, a benzyl group or phenylethyl group;
$R^7$ represents a hydrogen atom, a ($C_2$–$C_5$ alkanoyl)oxy($C_1$–$C_3$ alkyl) group, a ($C_1$–$C_4$ alkoxy)carbonyloxy($C_1$–$C_3$ alkyl) group, a (2-oxo-1,3-dioxolen-4-yl)alkyl group in which the alkyl is $C_1$–$C_3$ alkyl and which has a $C_1$–$C_4$ alkyl or phenyl substituent at the 5-position, or a phthalidyl group;
A represents an ethylene group;
B represents a methylene group; and
n is 0.

8. A compound as claimed in claim 1, in which:
$R^1$ represents a phenyl group or a $C_2$–$C_7$ alkyl group;
$R^2$ represents a 2-thienyl group, a 3-thienyl group or a 2-furyl group;
$R^3$, $R^4$ and $R^5$ all represent hydrogen atoms;
$R^6$ represents a hydrogen atom, a $C_1$–$C_4$ alkyl group or a benzyl group;
$R^7$ represents a hydrogen atom, a ($C_2$–$C_5$ alkanoyl)oxy($C_1$–$C_3$ alkyl) group, a ($C_1$–$C_4$ alkoxy)carbonyloxy($C_1$–$C_2$ alkyl) group, a (5-methyl-2-oxo-1,3-dioxolen-4-yl)methyl group or a (5-phenyl-2-oxo-1,3-dioxolen-4-yl)methyl group;
A represents an ethylene group;
B represents a methylene group; and
n is 0.

9. A compound as claimed in claim 1, in which:
$R^1$ represents a phenyl group or a $C_2$–$C_7$ alkyl group;
$R^2$ represents a phenyl group, a naphthyl group, a $C_1$–$C_6$ alkyl group or a $C_3$–$C_8$ cycloalkyl group;
$R^3$, $R^4$ and $R^5$ all represent hydrogen atoms;
$R^6$ represents a hydrogen atom, a $C_1$–$C_6$ alkyl group or an aralkyl group of which the aryl part is a $C_1$–$C_{10}$ carbocyclic aryl group and the alkyl part is a $C_1$–$C_4$ alkyl group;
$R^7$ represents a hydrogen atom, an acyloxyalkyl group, an alkoxycarbonyloxyalkyl group, a (2-oxo-1,3-dioxolen-4-yl)alkyl group where the alkyl group is $C_1$–$C_4$ and which has a $C_1$–$C_4$ alkyl or phenyl substituent at the 5-position, or a phthalidyl group;
A represents an ethylene group;
B represents a methylene group; and
n is 0.

10. A compound as claimed in claim 1, in which:
$R^1$ represents a phenyl group or a $C_2$–$C_7$ alkyl group;
$R^2$ represents a naphthyl group;
$R^3$, $R^4$ and $R^5$ all represent hydrogen atoms;
$R^6$ represents a hydrogen atom, a $C_1$–$C_6$ alkyl group or an aralkyl group of which the aryl part is a $C_6$–$C_{10}$ carbocyclic aryl group and the alkyl part is a $C_1$–$C_{10}$ alkyl group;
$R^7$ represents a hydrogen atom, an acyloxyalkyl group, an alkoxycarbonyloxyalkyl group, a (2-oxo-1,3-dioxolen-4-yl)alkyl group where the alkyl group is $C_1$–$C_4$ and which has a $C_1$–$C_4$ alkyl or phenyl substituent at the 5-position, or a phthalidyl group;
A represents an ethylene group;
B represents a methylene group; and
n is 0.

11. A compound as claimed in claim 1, in which:
$R^1$ represents a phenyl group or a $C_2$–$C_7$ alkyl group;
$R^2$, $R^3$ and $R^5$ all represent hydrogen atoms;
$R^4$ represents a heterocyclic group (ii) having 5 or 6 ring atoms;
$R^6$ represents a hydrogen atom, a $C_1$–$C_4$ alkyl group, a benzyl group or a phenylethyl group;
$R^7$ represents a hydrogen atom, an acyloxyalkyl group, an alkoxycarbonyloxyalkyl group, a (5-alkyl-2-oxo-1,3-dioxolen-4-yl)alkyl group in which each alkyl group is $C_1$–$C_4$, a (5-phenyl-2-oxo-1,3-dioxolen-4-yl)alkyl group in which the alkyl part is $C_1$–$C_4$ or a phthalidyl group;
A represents an ethylene group;
B represents a methylene group; and
n is 0.

12. A compound as claimed in claim 1, in which:
$R^1$ represents a phenyl group or a $C_2$–$C_7$ alkyl group;
$R^2$, $R^3$ and $R^5$ all represent hydrogen atoms;
$R^4$ represents a $C_1$–$C_6$ alkyl group, a phenyl group, a naphthyl group or a $C_3$–$C_8$ cycloalkyl group;

R⁶ represents a hydrogen atom, a $C_1$–$C_4$ alkyl group, a benzyl group or a phenylethyl group;

R⁷ represents a hydrogen atom, a ($C_2$–$C_5$ alkanoyl)oxy($C_1$–$C_3$ alkyl) group, a ($C_1$–$C_4$ alkoxy)carbonyloxy($C_1$–$C_3$ alkyl) group, a (5-alkyl-2-oxo-1,3-dioxolen-4-yl)alkyl group in which each alkyl part is $C_1$–$C_3$, a (5-phenyl-2-oxo-1,3-dioxolen-4-yl)alkyl group in which the alkyl part is $C_1$–$C_3$ or a phthalidyl group;

A represents an ethylene group;

B represents a methylene group; and n is 0.

13. The compound of claim 1 which is α-[6-(1-carboxy-3-phenylpropylamino)-2-(3-furyl)-5-oxoperhydro-1,4-thiazepin-4-yl]acetic acid.

14. The compound of claim 1 which is α-[6-(1-ethoxycarbonyl-3-phenylpropylamino)-2-(3-furyl)-5-oxoperhydro-1,4-thiazepin-4-yl]acetic acid.

15. The compound of claim 1 which is α-[6-(1-butoxycarbonyl-3-phenylpropylamino)-2-(3-furyl)-5-oxoperhydro-1,4-thiazepin-4-yl]acetic acid.

16. The compound of claim 1 which is α-[6-(1-carboxy-3-phenylpropylamino)-5-oxo-2-(1,3-thiazol-4-yl)perhydro-1,4-thiazepin-4-yl]acetic acid.

17. The compound of claim 1 which is α-[6-(1-ethoxycarbonyl-3-phenylpropylamino)-5-oxo-2-(1,3-thiazol-4-yl)perhydro-1,4-thiazepin-4-yl]acetic acid.

18. The compound of claim 1 which is α-[6-(1-butoxycarbonyl-3-phenylpropylamino)-5-oxo-2-(1,3-thiazol-4-yl)perhydro-1,4-thiazepin-4-yl]acetic acid.

19. The compound of claim 1 which is α-[6-(1-carboxynonylamino)-5-oxo-2-(2-thienyl)perhydro-1,4-thiazepin-4-yl]acetic acid.

20. The compound of claim 1 which is α-[6-(1-ethoxycarbonylnonylamino)-5-oxo-2-(2-thienyl)perhydro-1,4-thiazepin-4-yl]acetic acid.

21. The compound of claim 1 which is α-[6-(1-carboxy-3-phenylpropylamino)-5-oxo-2-(2-thienyl)perhydro-1,4-thiazepin-4-yl]acetic acid.

22. The compound of claim 1 which is α-[6-(1-ethoxycarbonyl-3-phenylpropylamino)-5-oxo-2-(2-thienyl)-perhydro-1,4-thiazepin-4-yl]acetic acid.

23. The compound of claim 1 which is α-[6-(1-butoxycarbonyl-3-phenylpropylamino)-5-oxo-2-(2-thienyl)-perhydro-1,4-thiazepin-4-yl]acetic acid.

24. The compound of claim 1 which is α-[6-(1-carboxy-3-phenylpropylamino)-5-oxo-2-(3-thienyl)perhydro-1,4-thiazepin-4-yl]acetic acid.

25. The compound of claim 1 which is α-[6-(1-ethoxycarbonyl-3-phenylpropylamino)-5-oxo-2-(3-thienyl)-perhydro-1,4-thiazepin-4-yl]acetic acid.

26. The compound of claim 1 which is α-[6-(1-butoxycarbonyl-3-phenylpropylamino)-5-oxo-2-(3-thienyl)-perhydro-1,4-thiazepin-4-yl]acetic acid.

27. The compound of claim 1 which is α-[6-(1-carboxy-3-phenylpropylamino)-2-(2-furyl)-5-oxoperhydro-1,4-thiazepin-4-yl]acetic acid.

28. The compound of claim 1 which is α-[6-(1-ethoxycarbonyl-3-phenylpropylamino)-2-(2-furyl)-5-oxoperhydro-1,4-thiazepin-4-yl]acetic acid.

29. The compound of claim 1 which is α-[6-(1-butoxycarbonyl-3-phenylpropylamino)-2-(2-furyl)-5-oxoperhydro-1,4-thiazepin-4-yl]acetic acid.

30. The compound of claim 1 which is α-[6-(1-ethoxycarbonylnonylamino)-5-oxo-2-(3-thienyl)perhydro-1,4-thiazepin-4-yl]acetic acid.

31. The compound of claim 1 which is α-[6-(1-ethoxycarbonyl-3-phenylpropylamino)-2-(3-methyl-2-thienyl)-5-oxoperhydro-1,4-thiazepin-4-yl]acetic acid.

32. The compound of claim 1 which is α-[6-(1-ethoxycarbonyl-3-phenylpropylamino)-2-(5-methyl-2-thienyl)-5-oxoperhydro-1,4-thiazepin-4-yl]acetic acid.

33. A pharmaceutical composition for the treatment of angiotensin-induced hypertension, which composition comprises a hypotensive agent in admixture with a pharmaceutically acceptable carrier or diluent, wherein said hypotensive agent is selected from the group consisting of compounds of formula (Ia)

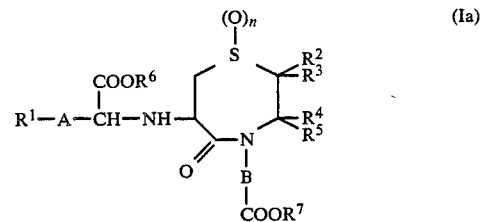

wherein

R¹ is selected from the group consisting of $C_1$–$C_{10}$ alkyl groups, $C_3$–$C_8$ cycloalkyl groups, carbocyclic aryl groups having 6 or 10 ring carbon atoms, partially hydrogenated carbocyclic aryl groups having 6 or 10 ring carbon atoms, and heterocyclic groups (i) selected from the group consisting of thiazolyl, imidazolyl, oxazolyl, isoxazolyl, furyl and thienyl, said groups R¹ being unsubstituted or having at least one substituent selected from the group consisting of a oxo groups, $C_1$–$C_6$ alkyl groups, $C_6$ or $C_{10}$ carbocyclic aryl groups, aralkyl groups wherein the alkyl part is $C_1$–$C_6$ alkyl and the aryl part is $C_6$ or $C_{10}$ carbocyclic aryl, hydroxy groups, $C_1$–$C_6$ alkoxy groups, alkoxyalkoxy groups where each alkoxy part is $C_1$–$C_6$, aralkyloxy groups, wherein the alkoxy part is $C_1$–$C_6$ alkoxy and the aryl part is $C_6$ or $C_{10}$ carbocyclic aryl, aryloxy groups wherein the aryl part is $C_6$ or $C_{10}$ carbocyclic aryl, halogen atoms, nitro groups, cyano groups, carboxy groups, alkoxycarbonyl groups wherein the alkoxy part is $C_1$–$C_6$ alkoxy, amino groups, $C_1$–$C_6$ alkylamino groups, dialkylamino groups wherein each alkyl part is $C_1$–$C_6$ alkyl, $C_1$–$C_7$ aliphatic or carbocyclic $C_6$ or $C_{10}$ aryl carboxylic acylamino groups, carbamoyl groups, alkylcarbamoyl groups where the alkyl part is $C_1$–$C_6$ alkyl, dialkylcarbamoyl groups where each alkyl part is $C_1$–$C_6$ alkyl, $C_1$–$C_6$ alkylthio groups, $C_6$ and $C_{10}$ carbocyclic arylthio groups, $C_1$–$C_6$ alkylsulfonyl groups and $C_6$ or $C_{10}$ carbocyclic arylsulfonyl groups wherein the aryl part is unsubstituted or has from 1 to 3 $C_1$–$C_6$ alkyl substituents;

R², R³, R⁴ and R⁵ are independently selected from the group consisting of hydrogen atoms, $C_1$–$C_{10}$ alkyl groups, $C_3$–$C_8$ cycloalkyl groups, aralkyl groups wherein the alkyl part is $C_1$–$C_6$ alkyl and the aryl part is $C_6$ or $C_{10}$ carbocyclic aryl, $C_6$ or $C_{10}$ carboxylic aryl groups, heterocyclic groups (ii) selected from the group consisting of tetrahydrofuranyl, tetrahydrothienyl, tetrahydropyranyl, morpholinyl, furyl, thienyl, imidazolyl, thiazolyl, oxazolyl, isoxazolyl, 1,3,4-oxadiazolyl, 1,3,4-thiadiazolyl, pyridyl, quinolyl, isoquinolyl and indolyl, and heterocyclic substituted $C_1$–$C_6$ alkyl groups having a heterocyclic substituent selected from said heterocyclic groups (ii); provided that $R^2$, $R^3$, $R^4$ and $R^5$ are not all hydrogen atoms, said groups represented by $R^2$, $R^3$, $R^4$ and $R^5$ being unsubstituted or having at least one substituent selected from the group consisting of the substituents defined in (a) above, or each of $R^2$ and $R^3$, $R^4$ and $R^5$ or $R^2$ and $R^4$ are selected from the group consisting of cyclopropane, cyclopentane, cyclohexane, tetrahydrofuran, tetrahydropyran, tetrahydrothiphene, pyrrolidine, piperidine, indane and 1,2,3,4-tetrahydronaphthalene;

$R^6$ is selected from the group consisting of hydrogen, $C_1$–$C_{10}$ alkyl, and aralkyls which are $C_6$ or $C_{10}$ aryl-$C_1$–$C_6$ alkyl;

$R^7$ is selected from the group consisting of hydrogen, ($C_1$–$C_4$ alkoxy)carbonyloxy($C_1$–$C_4$ alkyl), ($C_2$–$C_5$ alkanoyl)oxy($C_1$–$C_4$ alkyl), (5-alkyl-2-oxo-1,3-dioxolen-4-yl)alkyls in which each alkyl group has from 1 to 4 carbon atoms, (5-phenyl-2-oxo-1,3-dioxolen-4-yl)alkyls in which the alkyl part has from 1 to 4 carbon atoms, and phthalidyl;

A is a direct carbon-carbon bond, a methylene group, an ethylene group, an oxymethyl group or a thiomethyl group;

B is a $C_1$–$C_4$ alkylene or alkylidene group or a $C_3$–$C_6$ cycloalkylene or cycloalkylidene group;

n is 0, 1 or 2; and pharmaceutically acceptable salts thereof.

34. A composition as claimed in claim 33 in which:
$R^1$ represents a phenyl group or a $C_2$–$C_7$ alkyl
$R^2$ and $R^4$ are the same or different and each represents a hydrogen atom, a $C_1$–$C_{10}$ alkyl group, a phenyl group, a naphthyl group, a $C_3$–$C_8$ cycloalkyl group or a heterocyclic group (ii);
$R^3$ and $R^5$ both represent hydrogen atoms;
A represents an ethylene group;
B represents a methylene group; and
n is 0.

35. A composition as claimed in claim 34, in which:
$R^2$ and $R^4$ are the same or different and each represents a hydrogen atom, a $C_1$–$C_{10}$ alkyl group, a phenyl group, a naphthyl group, a $C_3$–$C_8$ cycloalkyl group or a heterocyclic group having 5 or 6 ring atoms.

36. A composition as claimed in claim 33, in which:
$R^1$ represents a phenyl group or a $C_2$–$C_7$ alkyl group;
$R^2$ represents a $C_1$–$C_{10}$ alkyl group, a phenyl group, a naphthyl group, a $C_3$–$C_8$ cycloalkyl group or a heterocyclic group (ii) having 5 or 6 ring atoms;
$R^3$, $R^4$ and $R^5$ all represent hydrogen atoms;
A represents an ethylene group;
B represents a methylene group; and
n is 0.

37. A composition as claimed in claim 33, in which:
$R^1$ represents a phenyl group or a $C_2$–$C_7$ alkyl groups;
$R^2$ represents a heterocyclic group (ii) having 5 or 6 ring atoms;
$R^3$, $R^4$ and $R^5$ all represent hydrogen atoms;
$R^6$ represents a hydrogen atom, a $C_1$–$C_6$ alkyl group or an aralkyl group of which the aryl part is a $C_6$ or $C_{10}$ carbocyclic aryl group and the alkyl part is a $C_1$–$C_4$ alkyl group;
A represents an ethylene group;
B represents a methylene group; and
n is 0.

38. A composition as claimed in claim 33, in which:
$R^1$ represents a phenyl group or a $C_2$–$C_7$ alkyl group;
$R^2$ represents a heterocyclic group (ii) having 5 ring atoms;
$R^3$, $R^4$ and $R^5$ all represent hydrogen atoms;
$R^6$ represents a hydrogen atom, a $C_1$–$C_6$ alkyl group or an aralkyl group of which the aryl part is a $C_6$ or $C_{10}$ carbocyclic aryl group and the alkyl part is a $C_1$–$C_4$ alkyl group;
A represents an ethylene group;
B represents a methylene group; and
n is 0.

39. A composition as claimed in claim 33, in which:
$R^1$ represents a phenyl group or a $C_2$–$C_7$ alkyl group;
$R^2$ represents a thienyl group or furyl group;
$R^3$, $R^4$ and $R^5$ all represent hydrogen atoms;
$R^6$ represents a hydrogen atom, a $C_1$–$C_4$ alkyl group, a benzyl group or phenylethyl group;
$R^7$ represents a hydrogen atom, a ($C_2$–$C_5$ alkanoyl)oxy($C_1$–$C_3$ alkyl) group, a ($C_1$–$C_4$ alkoxy)carbonyloxy($C_1$–$C_3$ alkyl) group, a (2-oxo-1,3-dioxolen-4-yl)alkyl group in which the alkyl is $C_1$–$C_3$ alkyl and which has a $C_1$–$C_4$ alkyl or phenyl substituent at the 5-position, or a phthalidyl group;
A represents an ethylene group;
B represents a methylene group; and
n is 0.

40. A composition as claimed in claim 33, in which:
$R^1$ represents a phenyl group or a $C_2$–$C_7$ alkyl group;
$R^2$ represents a 2-thienyl group, a 3-thienyl group or a 2-furyl group;
$R^3$, $R^4$ and $R^5$ all represent hydrogen atoms;
$R^6$ represents a hydrogen atom, a $C_1$–$C_4$ alkyl group or a benlyl group;
$R^7$ represents a hydrogen atom, a ($C_2$–$C_5$ alkanoyl)oxy($C_1$–$C_3$ alkyl) group, a ($C_1$–$C_4$ alkoxy)carbonyloxy($C_1$–$C_2$ alkyl) group, a (5-methyl-2-oxo-1,3-dioxolen-4-yl)methyl group or a (5-phenyl-2-oxo-1,3-dioxolen-4-yl)methyl group;
A represents an ethylene group;
B represents a methylene group; and
n is 0.

41. A composition as claimed in claim 33, in which:
$R^1$ represents a phenyl group or a $C_2$–$C_7$ alkyl group;
$R^2$ represents a phenyl group, a naphthyl group, a $C_1$–$C_6$ alkyl group or a $C_3$–$C_8$ cycloalkyl group;
$R^3$, $R^4$ and $R^5$ all represent hydrogen atoms;
$R^6$ represents a hydrogen atom, a $C_1$–$C_6$ alkyl group or an aralkyl group of which the aryl part is a $C_6$–$C_{10}$ carbocyclic aryl group and the alkyl part is a $C_1$–$C_4$ alkyl group;
$R^7$ represents a hydrogen atom, an acyloxyalkyl group, an alkoxycarbonyloxyalkyl group, a (2-oxo-1,3-dioxolen-4-yl)alkyl group where the alkyl group is $C_1$–$C_4$ and which has a $C_1$–$C_4$ alkyl or phenyl substituent at the 5-position, or a phthalidyl group;
A represents an ethylene group;
B represents a methylene group; and
n is 0.

42. A composition as claimed in claim 33, in which:
$R^1$ represents a phenyl group or a $C_2$–$C_7$ alkyl group;
$R^2$ represents a naphthyl group;
$R^3$, $R^4$ and $R^5$ all represent hydrogen atoms;
$R^6$ represents a hydrogen atom, a $C_1$–$C_6$ alkyl group or an aralkyl group of which the aryl part is a $C_6$–$C_{10}$ carbocyclic aryl group and the alkyl part is a $C_1$–$C_4$ alkyl group;

R⁷ represents a hydrogen atom, an acyloxyalkyl group, an alkoxycarbonyloxyalkyl group, a (2-oxo-1,3-dioxolen-4-yl)alkyl group where the alkyl group is $C_1$–$C_4$ and which has a $C_1$–$C_4$ alkyl or phenyl substituent at the 5-position, or a phthalidyl group;

A represents an ethylene group;
B represents a methylene group; and
n is 0.

43. A composition as claimed in claim 33, in which:
$R^1$ represents a phenyl group or a $C_2$–$C_7$ alkyl group;
$R^2$, $R^3$ and $R^5$ all represent hydrogen atoms;
$R^4$ represents a heterocyclic group (ii) having 5 or 6 ring atoms;
$R^6$ represents a hydrogen atom, a $C_1$–$C_4$ alkyl group, a benzyl group or a phenylethyl group;
$R^7$ represents a hydrogen atom, an acyloxyalkyl group, an alkoxycarbonyloxyalkyl group, a (5-alkyl-2-oxo-1,3-dioxolen-4-yl)alkyl group in which each alkyl group is $C_1$–$C_4$, a (5-phenyl-2-oxo-1,3-dioxolen-4-yl)alkyl group in which the alkyl part is $C_1$–$C_4$ or a phthalidyl group;
A represents an ethylene group;
B represents a methylene group; and
n is 0.

44. A composition as claimed in claim 33, in which:
$R^1$ represents a phenyl group or a $C_2$–$C_7$ alkyl group;
$R^2$, $R^3$ and $R^5$ all represent hydrogen atoms;
$R^4$ represents a $C_1$–$C_6$ alkyl group, a phenyl group, a naphthyl group or a $C_3$–$C_8$ cycloalkyl group;
$R^6$ represents a hydrogen atom, a $C_1$–$C_4$ alkyl group, a benzyl group or a phenylethyl group;
$R^7$ represents a hydrogen atom, a ($C_2$–$C_5$ alkanoyl)oxy($C_1$–$C_3$ alkyl) group, a ($C_1$–$C_4$ alkoxy)carbonyloxy($C_1$–$C_3$ alkyl) group, a (5-alkyl-2-oxo-1,3-dioxolen-4-yl)alkyl group in which each alkyl part is $C_1$–$C_3$, a (5-phenyl-2-oxo-1,3-dioxolen-4-yl)alkyl group in which the alkyl part is $C_1$–$C_3$ or a phthalidyl group;
A represents an ethylene group;
B represents a methylene group; and
n is 0.

45. A composition as claimed in claim 33, wherein said hypotensive agent is selected from the group consisting of:

α-[6-(1-carboxy-3-phenylpropylamino)-5-oxo-2-(2-thienyl)perhydro-1,4-thiazepin-4-yl]acetic acid
α-[6-(1-ethoxycarbonyl-3-phenylpropylamino)-5-oxo-2-(2-thienyl)perhydro-1,4-thiazepin-4-yl]acetic acid
α-[6-(1-butoxycarbonyl-3-phenylpropylamino)-5-oxo-2-(2-thienyl)perhydro-1,4-thiazepin-4-yl]acetic acid
α-[6-(1-carboxy-3-phenylpropylamino)-5-oxo-2-(3-thienyl)perhydro-1,4-thiazepin-4-yl]acetic acid
α-[6-(1-ethoxycarbonyl-3-phenylpropylamino)-5-oxo-2-(3-thienyl)perhydro-1,4-thiazepin-4-yl]acetic acid
α-[6-(1-butoxycarbonyl-3-phenylpropylamino)-5-oxo-2-(3-thienyl)perhydro-1,4-thiazepin-4-yl]acetic acid
α-[6-(1-carboxy-3-phenylpropylamino)-2-(2-furyl)-5-oxoperhydro-1,4-thiazepin-4-yl]acetic acid
α-[6-(1-ethoxycarbonyl-3-phenylpropylamino)-2-(2-furyl)-5-oxoperhydro-1,4-thiazepin-4-yl]acetic acid
α-[6-(1-butoxycarbonyl-3-phenylpropylamino)-2-(2-furyl)-5-oxoperhydro-1,4-thiazepin-4-yl]acetic acid
α-[6-(1-carboxy-3-phenylpropylamino)-2-(3-furyl)-5-oxoperhydro-1,4-thiazepin-4-yl]acetic acid
α-[6-(1-ethoxycarbonyl-3-phenylpropylamino)-2-(3-furyl)-5-oxoperhydro-1,4-thiazepin-4-yl]acetic acid
α-[6-(1-butoxycarbonyl-3-phenylpropylamino)-2-(3-furyl)-5-oxoperhydro-1,4-thiazepin-4-yl]acetic acid
α-[6-(1-carboxy-3-phenylpylamino)-5-oxo-2(1,3-thiazol-4-yl)perhydro-1,4-thiazepin-4-yl]acetic acid
α-[6-(1-ethoxycarbonyl-3-phenylpropylamino)-5-oxo-2-(1,3-thiazol-4-yl)perhydro-1,4-thiazepin-4-yl]acetic acid
α-[6-(1-butoxycarbonyl-3-phenylpropylamino)-5-oxo-2-(1,3-thiazol-4-yl)perhydro-1,4-thiazepin-4-yl]acetic acid
α-[6-(1-carboxynonylamino)-5-oxo-2-(2-thienyl)perhydro-1,4-thiazepin-4-yl]acetic acid
α-[6-(1-ethoxycarbonylnonylamino)-5-oxo-2-(2-thienyl)perhydro-1,4-thiazepin-4-yl]acetic acid
α-[6-(1-ethoxycarbonylnonylamino)-5-oxo-2-(3-thienyl)perhydro-1,4-thiazepin-4-yl]acetic acid
α-[6-(1-ethoxycarbonyl-3-phenylpropylamino)-2-(3-methyl-2-thienyl)-5-oxoperhydro-1,4-thiazepin-4-yl]acetic acid
α-[6-(1-ethoxycarbonyl-3-phenylpropylamino)-2-(5-methyl-2-thienyl)-5-oxoperhydro-1,4-thiazepin-4-yl]acetic acid.

46. A composition as claimed in claim 33, formulated for oral administration.

47. A composition as claimed in claim 33, formulated for parenteral administration.

48. A method of treating angiotensin-induced hypertension in a mammal by administring to said mammal an effective amount of a hypotensive agent, wherein said hypotensive agent is selected from the group consisting of compounds of formula (Ia)

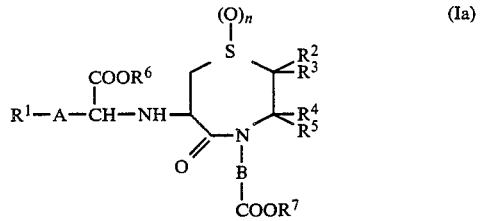

(Ia)

wherein
$R^1$ is selected from the group consisting of $C_1$–$C_{10}$ alkyl groups, $C_3$–$C_8$ cycloalkyl groups, carbocyclic aryl groups having 6 or 10 ring carbon atoms, partially hydrogenated carbocyclic aryl groups having 6 or 10 ring carbon atoms, and heterocyclic groups (i) selected from the group consisting of thiazolyl, imidazolyl, oxazolyl, isoxazolyl, furyl and thienyl, said groups $R^1$ being unsubstituted or having at least one substituent selected from the group consisting of (a) oxo groups, $C_1$–$C_6$ alkyl groups, $C_6$ or $C_{10}$ carbocyclic aryl groups, aralkyl groups wherein the alkyl part is $C_1$–$C_6$ alkyl and the aryl part is $C_6$ or $C_{10}$ carbocyclic aryl, hydroxy groups, $C_1$–$C_6$ alkoxy groups, alkoxyalkoxy groups where each alkoxy part is $C_1$–$C_6$, aralkyloxy groups, wherein the alkoxy part is $C_1$–$C_6$ alkoxy and the aryl part is $C_6$ or $C_{10}$ carbocyclic aryl, aryloxy groups wherein the aryl part is $C_6$ or $C_{10}$ carbocyclic aryl, halogen atoms, nitro groups, cyano groups, carboxy groups, alkoxycarbonyl groups wherein the alkoxy part is $C_1$–$C_6$ alkoxy, amino groups, $C_1$–$C_6$ alkylamino groups, dialkylamino groups wherein each alkyl part is $C_1$–$C_6$ alkyl, $C_1$–$C_7$ aliphatic or carbocyclic $C_6$ or $C_{10}$ aryl carboxylic acylamino groups, carbamoyl groups, alkylcarbamoyl groups where the alkyl part is $C_1$–$C_6$ alkyl, dialkylcarbamoyl groups where each alkyl part is $C_1$–$C_6$ alkyl, $C_1$–$C_6$ alkylthio groups, $C_6$ or $C_{10}$ carbocyclic arylthio groups, $C_1$–$C_6$ alkylsulfonyl groups and $C_6$ or $C_{10}$ carbocyclic arylsulfonyl groups wherein the aryl part is unsubstituted or has from 1 to 3 $C_1$–$C_6$ alkyl substituents;

$R^2$, $R^3$, $R^4$ and $R^5$ are independently selected from the group consisting of hydrogen atoms, $C_1$–$C_{10}$ alkyl groups, $C_3$–$C_8$ cycloalkyl groups, aralkyl groups wherein the alkyl part is $C_1$–$C_6$ alkyl and the aryl part is $C_6$ or $C_{10}$ carbocyclic aryl, $C_6$ or $C_{10}$ carboxylic aryl groups, heterocyclic groups (ii) selected from the group consisting of tetrahydrofuranyl, tetrahydrothienyl, tetrahydropyranyl, morpholinyl, furyl, thienyl, imidazolyl, thiazolyl, oxazolyl, isoxazolyl, 1,3,4-oxadiazolyl, 1,3,4-thiadiazolyl, pyridyl, quinolyl, isoquinolyl and indolyl, and heterocyclic substituted $C_1$–$C_6$ alkyl groups having a heterocyclic substituent selected from said heterocyclic groups (ii); provided that $R^2$, $R^3$, $R^4$ and $R^5$ are not all hydrogen atoms, said group represented by $R^2$, $R^3$, $R^4$ and $R^5$ being unsubstituted or having at least one substituent selected from the group consisting of the substituents defined in (a) above, or each of $R^2$ and $R^3$, $R^4$ and $R^5$ or $R^2$ and $R^4$ are selected from the group consisting of cyclopropane, cyclopentane, cyclohexane, tetrahydrofuran, tetrahydropyran, tetrahydrothiphene, pyrrolidine, piperidine, indane and 1,2,3,4-tetrahydronaphthalene;

$R^6$ is selected from the group consisting of hydrogen, $C_1$–$C_{10}$ alkyl, and aralkyls which are $C_6$ or $C_{10}$ aryl-$C_1$–$C_6$ alkyl;

$R^7$ is selected from the group consisting of hydrogen, ($C_1$–$C_4$ alkoxy)carbonyloxy($C_1$–$C_4$ alkyl), ($C_2$–$C_5$ alkanoyl)oxy($C_1$–$C_4$ alkyl), (5-alkyl-2-oxo-1,3-dioxolen-4-yl)alkyls in which each alkyl group has from 1 to 4 carbon atoms, (5-phenyl-2-oxo-1,3-dioxolen-4-yl)alkyls in which the alkyl part has from 1 to 4 carbon atoms, and phthalidyl;

A is a direct carbon-carbon bond, a methylene group, an ethylene group, an oxymethyl group or a thiomethyl group;

B is a $C_1$–$C_4$ alkylene or alkylidene group or a $C_3$–$C_6$ cycloalkylene or cycloalkylidene group;

n is 0, 1 or 2; and pharmaceutically acceptable salts thereof.

49. A method as claimed in claim 48, in which:

$R^1$ represents a phenyl group or a $C_2$–$C_7$ alkyl group;

$R^2$ and $R^4$ are the same or different and each represents a hydrogen atom, a $C_1$–$C_{10}$ alkyl group, a phenyl group, a naphthyl group, a $C_3$–$C_8$ cycloalkyl group or a heterocyclic group (ii) group or a heterocyclic group;

$R^3$ and $R^5$ both represent hydrogen atoms;

A represents an ethylene group;

B represents a methylene group; and n is 0.

50. A method as claimed in claim 48, in which: $R^2$ and $R^4$ are the same or different and each represents a hydrogen atom, a $C_1$–$C_{10}$ alkyl group, a phenyl group, a naphthyl group, a $C_3$–$C_8$ cycloalkyl group or a heterocyclic group having 5 or 6 ring atoms.

51. A method as claimed in claim 48, in which:

$R^1$ represents a phenyl group or a $C_2$–$C_7$ alkyl group;

$R^2$ represents a $C_1$–$C_{10}$ alkyl group, a phenyl group, a naphthyl group, a $C_3$–$C_8$ cycloalkyl group or a heterocyclic group (ii) having 5 or 6 ring atoms;

$R^3$, $R^4$ and $R^5$ all represent hydrogen atoms;

A represents an ethylene group;

B represents a methylene group; and n is 0.

52. A method as claimed in claim 48, in which:

$R^1$ represents a phenyl group or a $C_2$–$C_7$ alkyl groups;

$R^2$ represents a heterocyclic group (ii) having 5 or 6 ring atoms;

$R^3$, $R^4$ and $R^5$ all represent hydrogen atoms;

$R^6$ represents a hydrogen atom, a $C_1$–$C_6$ alkyl group or an aralkyl group of which the aryl part is a $C_6$ or $C_{10}$ carbocyclic aryl group and the alkyl part is a $C_1$–$C_4$ alkyl group;

A represents an ethylene group;

B represents a methylene group; and n is 0.

53. A method as claimed in claim 48, in which:

$R^1$ represents a phenyl group or a $C_2$–$C_7$ alkyl group;

$R^2$ represents a heterocyclic group (ii) having 5 ring atoms;

$R^3$, $R^4$ and $R^5$ all represent hydrogen atoms;

$R^6$ represents a hydrogen atom, a $C_1$–$C_6$ alkyl group or an aralkyl group of which the aryl part is a $C_6$ or $C_{10}$ carbocyclic aryl group and the alkyl part is a $C_1$–$C_4$ alkyl group;

A represents an ethylene group;

B represents a methylene group; and n is 0.

54. A method as claimed in claim 48, in which:

$R^1$ represents a phenyl group or a $C_2$–$C_7$ alkyl group;

$R^2$ represents a thienyl group or furyl group;

$R^3$, $R^4$ and $R^5$ all represent hydrogen atoms;

$R^6$ represents a hydrogen atom, a $C_1$–$C_4$ alkyl group, a benzyl group or phenylethyl group;

$R^7$ represents a hydrogen atom, a ($C_2$–$C_5$ alkanoyl)oxy($C_1$–$C_3$ alkyl) group, a ($C_1$–$C_4$ alkoxy)carbonyloxy($C_1$–$C_3$ alkyl) group, a (2-oxo-1,3-dioxolen-4-yl)alkyl group in which the alkyl is $C_1$–$C_3$ alkyl and which has a $C_1$–$C_4$ alkyl or phenyl substituent at the 5-position, or a phthalidyl group;

A represents an ethylene group;

B represents a methylene group; and n is 0.

55. A method as claimed in claim 48, in which:

$R^1$ represents a phenyl group or a $C_2$–$C_7$ alkyl group;

$R^2$ represents a 2-thienyl group, a 3-thienyl group or a 2-furyl group;

$R^3$, $R^4$ and $R^5$ all represent hydrogen atoms;

$R^6$ represents a hydrogen atom, a $C_1$–$C_4$ alkyl group or a benzyl group;

$R^7$ represents a hydrogen atom, a ($C_2$–$C_5$ alkanoyl)oxy($C_1$–$C_3$ alkyl) group, a ($C_1$–$C_4$ alkoxy)carbonyloxy($C_1$–$C_2$ alkyl) group, a (5-methyl-2-oxo-1,3-dioxolen-4-yl)methyl group or a (5-phenyl-2-oxo-1,3-dioxolen-4-yl)methyl group;

A represents an ethylene group;

B represents a methylene group; and n is 0.

56. A method as claimed in claim 48, in which:

$R^1$ represents a phenyl group or a $C_2$–$C_7$ alkyl group;

$R^2$ represents a phenyl group, a naphthyl group, a $C_1$–$C_6$ alkyl group or a $C_3$–$C_8$ cycloalkyl group;

$R^3$, $R^4$ and $R^5$ all represent hydrogen atoms;

$R^6$ represents a hydrogen atom, a $C_1$–$C_6$ alkyl group or an aralkyl group of which the aryl part is a $C_6$–$C_{10}$ carbocyclic aryl group and the alkyl part is a $C_1$–$C_4$ alkyl group;

$R^7$ represents a hydrogen atom, an acyloxyalkyl group, an alkoxycarbonyloxyalkyl group, a (2-oxo-1,3-dioxolen-4-yl)alkyl group where the alkyl group is $C_1$–$C_4$ and which has a $C_1$–$C_4$ alkyl or phenyl substituent at the 5-position, or a phthalidyl group;

A represents an ethylene group;

B represents a methylene group; and n is 0.

57. A method as claimed in claim 48, in which:

$R^1$ represents a phenyl group or a $C_2$–$C_7$ alkyl group;

$R^2$ represents a naphthyl group;

$R^3$, $R^4$ and $R^5$ all represent hydrogen atoms;

$R^6$ represents a hydrogen atom, a $C_1$–$C_6$ alkyl group or an aralkyl group of which the aryl part is a $C_6$–$C_{10}$ carbocyclic aryl group and the alkyl part is a $C_1$–$C_4$ alkyl group;

$R^7$ represents a hydrogen atom, an acyloxyalkyl group, an alkoxycarbonyloxyalkyl group, a (2-oxo-1,3-dioxolen-4-yl)alkyl group where the alkyl group is $C_1$–$C_4$ and which has a $C_1$–$C_4$ alkyl or phenyl substituent at the 5-position, or a phthalidyl group;

A represents an ethylene group;

B represents a methylene group; and n is 0.

58. A method as claimed in claim 48, in which:

$R^1$ represents a phenyl group or a $C_2$–$C_7$ alkyl group;

$R^2$, $R^3$ and $R^5$ all represent hydrogen atoms;

$R^4$ represents a heterocyclic group (ii) having 5 or 6 ring atoms;

$R^6$ represents a hydrogen atom, a $C_1$–$C_4$ alkyl group, a benzyl group or a phenylethyl group;

$R^7$ represents a hydrogen atom, an acyloxyalkyl group, an alkoxycarbonyloxyalkyl group, a (5-alkyl-2-oxo-1,3-dioxolen-4-yl)alkyl group in which each alkyl group is $C_1$–$C_4$, a (5-phenyl-2-oxo-1,3-dioxolen-4-yl)alkyl group in which the alkyl part is $C_1$–$C_4$ or a phthalidyl group;

A represents an ethylene group;

B represents a methylene group; and n is 0.

59. A method as claimed in claim 48, in which:

$R^1$ represents a phenyl group or a $C_2$–$C_7$ alkyl group;

$R^2$, $R^3$ and $R^5$ all represent hydrogen atoms;

$R^4$ represents a $C_1$–$C_6$ alkyl group, a phenyl group, a naphthyl group or a $C_3$–$C_8$ cycloalkyl group;

$R^6$ represents a hydrogen atom, a $C_1$–$C_4$ alkyl group, a benzyl group or a phenylethyl group;

$R^7$ represents a hydrogen atom, a ($C_2$–$C_5$ alkanoyl)oxy($C_1$–$C_3$ alkyl) group, a ($C_1$–$C_4$ alkoxy)carbonyloxy($C_1$–$C_3$ alkyl) group, a (5-alkyl-2-oxo-1,3-dioxolen-4-yl)alkyl group in which each alkyl part is $C_1$–$C_3$, a (5-phenyl-2-oxo-1,3-dioxolen-4-yl)alkyl group in which the alkyl part is $C_1$–$C_3$ or a phthalidyl group;

A represents an ethylene group;

B represents a methylene group; and n is 0.

60. A method as claimed in claim 48, wherein said hypotensive agent is selected from the group consisting of:

α-[6-(1-carboxy-3-phenylpropylamino)-5-oxo-2-(2-thienyl)perhydro-1,4-thiazepin-4-yl]acetic acid α-[6-(1-ethoxycarbonyl-3-phenylpropylamino)-5-oxo-2-(2-thienyl)perhydro-1,4-thiazepin-4-yl]acetic acid α-[6-(1-butoxycarbonyl-3-phenylpropylamino)-5-oxo-2-(2-thienyl)perhydro-1,4-thiazepin-4-yl]acetic acid α-[6-(1-carboxy-3-phenylpropylamino)-5-oxo-2-(3-thienyl)perhydro-1,4-thiazepin-4-yl]acetic acid α-[6-(1-ethoxycarbonyl-3-phenylpropylamino)-5-oxo-2-(3-thienyl)perhydro-1,4-thiazepin-4-yl]acetic acid α-[6-(1-butoxycarbonyl-3-phenylpropylamino)-5-oxo-2-(3-thienyl)perhydro-1,4-thiazepin-4-yl]acetic acid α-[6-(1-carboxy-3-phenylpropylamino)-2-(2-furyl)-5-oxoperhydro-1,4-thiazepin-4-yl]acetic acid α-[6-(1-ethoxycarbonyl-3-phenylpropylamino)-2-(2-furyl)-5-oxoperhydro-1,4-thiazepin-4-yl]acetic acid α-[6-(1-butoxycarbonyl-3-phenylpropylamino)-2-(2-furyl)-5-oxoperhydro-1,4-thiazepin-4-yl]acetic acid α-[6-(1-carboxy-3-phenylpropylamino)-2-(3-furyl)-5-oxoperhydro-1,4-thiazepin-4-yl]acetic acid α-[6-(1-ethoxycarbonyl-3-phenylpropylamino)-2-(3-furyl)-5-oxoperhydro-1,4-thiazepin-4-yl]acetic acid α-[6-(1-butoxycarbonyl-3-phenylpropylamino)-2-(3-furyl)-5-oxoperhydro-1,4-thiazepin-4-yl]acetic acid α-[6-(1-carboxy-3-phenylpropylamino)-5-oxo-2(1,3-thiazol-4-yl)perhydro-1,4-thiazepin-4-yl]acetic acid α-[6-(1-ethoxycarbonyl-3-phenylpropylamino)-5-oxo-2-(1,3-thiazol-4-yl)perhydro-1,4-thiazepin-4-yl]acetic acid α-[6-(1-butoxycarbonyl-3-phenylpropylamino)-5-oxo-2-(1,3-thiazol-4-yl)perhydro-1,4-thiazepin-4-yl]acetic acid α-[6-(1-carboxynonylamino)-5-oxo-2-(2-thienyl)perhydro-1,4-thiazepin-4-yl]acetic acid α-[6-(1-ethoxycarbonylnonylamino)-5-oxo-2-(2-thienyl)perhydro-1,4-thiazepin-4-yl]acetic acid α-[6-(1-ethoxycarbonylnonylamino)-5-oxo-2-(3-thienyl)perhydro-1,4-thiazepin-4-yl]acetic acid α-[6-(1-ethoxycarbonyl-3-phenylpropylamino)-2-(3-methyl-2-thienyl)-5-oxoperhydro-1,4-thiazepin-4-yl]acetic acid α-[6-(1-ethoxycarbonyl-3-phenylpropylamino)-2-(5-methyl-2-thienyl)-5-oxoperhydro-1,4-thiazepin-4-yl]acetic acid.

61. A method as claimed in claim 48, in which the agent is administered orally.

62. A method as claimed in claim 48, in which the agent is administered parenterally.

* * * * *

UNITED STATES PATENT AND TRADEMARK OFFICE
CERTIFICATE OF CORRECTION

PATENT NO. : 4,699,905
DATED : October 13, 1987
INVENTOR(S) : YANAGISAWA et al

It is certified that error appears in the above-identified patent and that said Letters Patent is hereby corrected as shown below:

Column 86, line 20 (Claim 9): delete "$C_1-C_{10}$" and insert --$C_6-C_{10}$--.

Column 86, line 38 (Claim 10): delete "$C_1-C_{10}$" and insert --$C_1-C_4$--.

Column 93, line 56 (Claim 49): delete "group or a".

Column 93, line 57 (Claim 49): delete "heterocyclic group".

Column 93, line 62 (Claim 50): delete "48" and insert --49--.

Signed and Sealed this

Twenty-eighth Day of April, 1998

Attest:

BRUCE LEHMAN

*Attesting Officer*  *Commissioner of Patents and Trademarks*